(12) United States Patent
Merchant

(10) Patent No.: US 6,713,062 B1
(45) Date of Patent: Mar. 30, 2004

(54) ACINETOBACTER OUTER MEMBRANE PROTEIN AND GENE SEQUENCE COMPOSITIONS AND METHODS

(75) Inventor: Juanita L. Merchant, Ann Arbor, MI (US)

(73) Assignee: The Regents of The University of Michigan, Ann Arbor, MI (US)

( * ) Notice: Subject to any disclaimer, the term of this patent is extended or adjusted under 35 U.S.C. 154(b) by 0 days.

(21) Appl. No.: 09/573,630

(22) Filed: May 17, 2000

Related U.S. Application Data

(60) Provisional application No. 60/134,399, filed on May 17, 1999.

(51) Int. Cl.[7] ................ A61K 39/00; A61K 39/02; G01N 33/53; C07K 14/00; C07K 1/00
(52) U.S. Cl. ................ 424/185.1; 424/190.1; 424/234.1; 435/975; 530/300; 530/324; 530/326; 530/327; 530/328; 530/350
(58) Field of Search .............. 435/6, 7.1; 536/23.7; 424/184.1, 185.1, 190.1, 234.1; 530/300, 324, 326, 327, 328, 350

(56) References Cited

FOREIGN PATENT DOCUMENTS

WO     WO 9509025    *   4/1995

OTHER PUBLICATIONS

Ellis, RW "Vaccines" Chapter 29 Plotkin, SA et al (ed) p. 571, 1988.*
Ofori–Darko, et al., "An OmpA–Like Protein from Acinetobter spp. Stimulates Gastrin and Interleukin–8 Promoters," *Infection and Immunity*, 68(6):3657–3666, Jun., 2000.

Ofori–Darko, et al., Genbank Sequence Accession No. AF132598; submitted to Genbank Mar. 2, 1999, but not released to public until May 25, 2000.

Ofori–Darko, et al., "Isolation and Cloning of an *H. Pylori* Protein That Stimulates Gastrin Promoter Activity," *Gastroenterology*, 116 (4 part 2), A631, Apr., 1999.

Tarle, et al., "*Helicobacter Pylori* Adherence to Human Gastric Cells Stimulates Gastrin Promoter Activity," *Gastroenterology*, 116 (4 part 2): A830, Apr., 1999.

Zavros, et al. "*H. pylori* OMP A Stimulates Proliferation and IL–8 Production in Gastric Cell Line," presented at the 10th International Workshop on CHRO, Sep. 12–16, 1999 (not published in journal form).

* cited by examiner

*Primary Examiner*—Mark Navarro
(74) *Attorney, Agent, or Firm*—Williams, Morgan and Amerson

(57) ABSTRACT

Disclosed are new outer membrane proteins and nucleic acids from Acinetobacter and related biological compositions and methods. The biological materials provided are useful in diagnostic, immunological and therapeutic applications, particularly those connected with peptic ulcers and cancers, respiratory diseases, sepsis and a variety of other conditions.

41 Claims, 12 Drawing Sheets

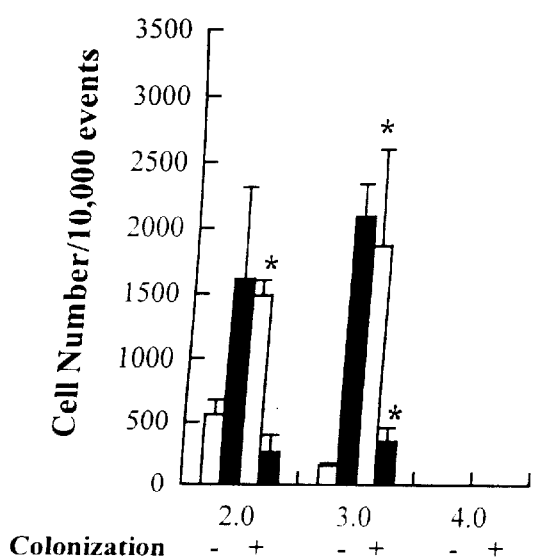
FIG. 9A
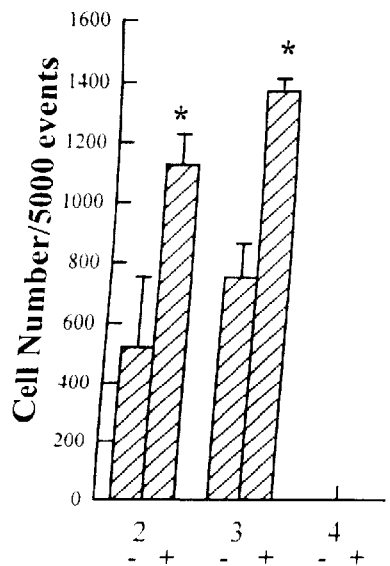
FIG. 9C
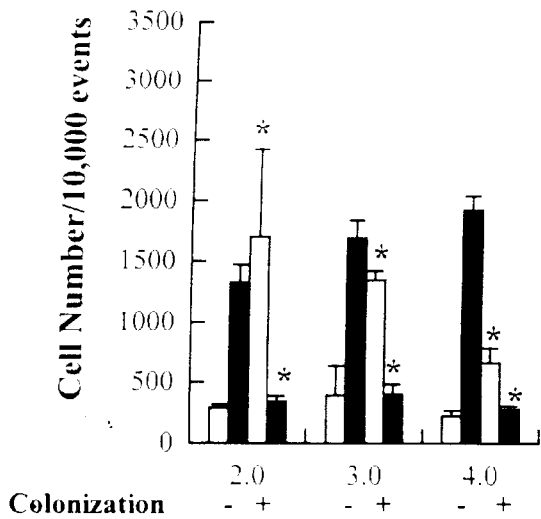
FIG. 9B
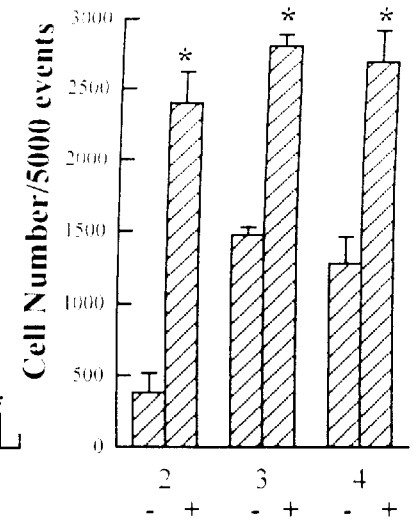
FIG. 9D
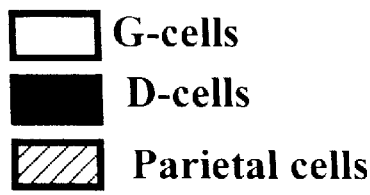
*$P<0.05$ vs -colonization
n=3-6 animals

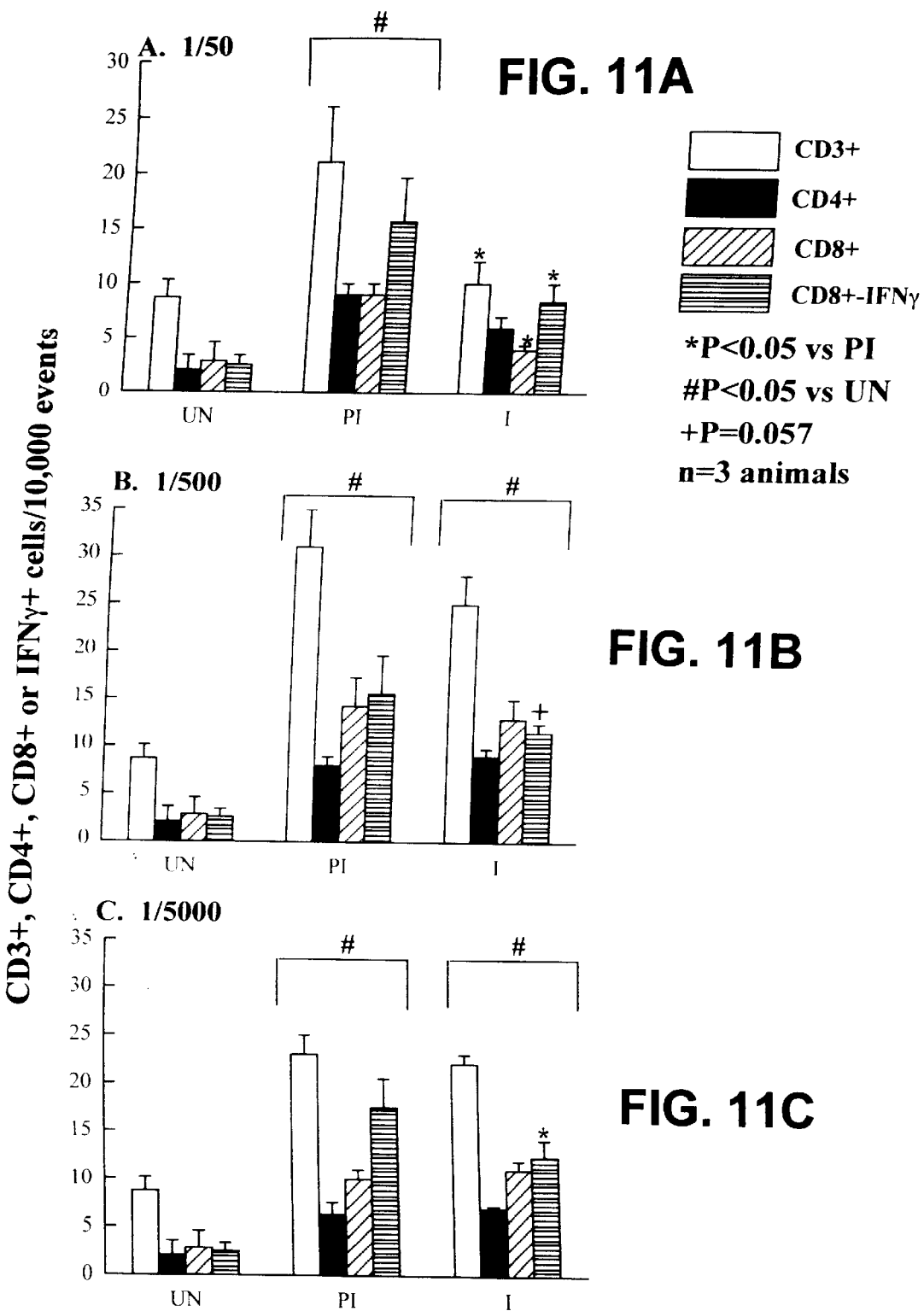

ACINETOBACTER OUTER MEMBRANE PROTEIN AND GENE SEQUENCE COMPOSITIONS AND METHODS

The present application claims priority to co-pending U.S. provisional patent application Serial No. 60/134,399, filed May 17, 1999, the entire text, drawings and sequences of which application are specifically incorporated by reference herein without disclaimer.

The U.S. Government owns rights in the present invention pursuant to Public Health Services grant DK-45729.

BACKGROUND OF THE INVENTION

1. Field of the Invention

The present invention relates generally to the field of genes and proteins derived from pathogenic bacteria. More particularly, the invention provides Acinetobacter outer membrane protein and gene compositions and methods for making and using a range of biological components related thereto. The invention thus provides nucleic acids, proteins, peptides and antibodies for use in various diagnostic and therapeutic applications, including those connected with peptic ulcers and cancers, respiratory diseases, sepsis and other conditions.

2. Description of Related Art

Helicobacter pylori (H. pylori) causes chronic gastritis and is correlated with the development of peptic ulcer disease and gastric carcinoma (Marshall et al, 1994; Graham, 1998; Nomura et al., 1991). However, there is also a potential association between colonization of the stomach by non-Helicobacter organisms and gastric atrophy and gastritis (Elliott et al., 1998; Haruma et al., 1995; Saunders et al., 1998).

Studies in the human and monkey have clearly shown that bacteria are important in triggering mucosal damage and inflammation in the stomach (Khanolkar-Gaitonde et al., 2000; Stockbruegger et al., 1984). It is not currently known whether colonization by non-Helicobacter organisms triggers perturbations in the neuroendocrine and epithelial cell populations. The implications being that the pathology observed may not be specific for H. pylori, but instead is the general response of the gastric mucosa to bacteria.

H. pylori is characterized by its ability to survive in the low-pH environment of the stomach by generating an alkaline microenvironment. However, with reduced levels of acid (hypochlorhydria or achlorhydria), the competitive niche established by H. pylori dissipates and the human stomach is colonized by other organisms (Haruma et al., 1995; Lehy et al., 2000). The colonization with aerobic and anaerobic flora that occurs in the stomach with increasing pH (Torres et al., 1996) may be the result of increasing age, malnutrition or iatrogenically induced achlorhydria, e.g., H2-receptor blockade or proton-pump inhibitor administration. Importantly, chronic achlorhydria is a risk factor for gastric cancer (Seery, 1991). With the exception of "stress ulcer" treatment, the bacterial flora present under conditions of hypochlorhydria has been poorly studied.

Patients in intensive care units often have a gastric pH of >3 due to the routine use of antacids, proton pump inhibitors or H2-receptor antagonists to prevent "stress ulcers". An increase in gastric pH permits colonization of the stomach with opportunistic pathogens that contribute to the development of nosocomial pneumonia (Garrouste-Orgeas et al., 1997). Bacteria cultured from the relatively alkaline stomachs of ventilated patients (Garrouste-Orgeas et al, 1997) have been implicated in nosocomial respiratory infections (Craven et al., 1990). In a study examining oropharyngeal and gastric colonization using DNA genomic analysis, gastric colonization occurred regardless of the pH, which ranged from 2.8 to 5.7. Antacids were not used and H2-receptor antagonists were used occasionally. A notable incidence if nosocomial pneumonias was reported in ventilated patients, despite the use of broad-spectrum antibiotics, e.g., amoxicillin and aminoglycosides.

As pathogenic organisms evidently exist that are able to evade or counteract currently available antibiotics, there is a need in the art to identify organisms and virulence factors from gastric bacterial flora that cause or contribute to gastric and systemic diseases. The identification of a surface accessible molecule from such a pathogenic organism would be a significant advance, leading long sought after diagnostics and therapeutics.

SUMMARY OF THE INVENTION

The present invention overcomes these and other drawbacks inherent in the prior art by linking Acinetobacter with various diseases and disorders and by providing Acinetobacter outer membrane protein A (OMP A) protein and gene compositions for therapeutics and diagnostics. The OMP A nucleic acid, protein, peptide and antibody compositions thus provided are useful in a variety of embodiments, including the diagnosis and therapy of peptic ulcers and cancers, respiratory diseases, sepsis and other conditions. Uses of the invention as part of a battery of diagnostic agents and in combination therapies are also provided.

The invention thus provides isolated nucleic acid molecules or segments comprising at least a first isolated coding region of at least about 800, 850, 900, 910, 920, 930, 940, 950, 960, 970 or 980 nucleotides or so in length that specifically hybridizes, preferably under conditions of stringency, and more preferably under conditions of high stringency, to the coding region of the nucleotide sequence set forth in SEQ ID NO:1 or to the coding region of the nucleotide sequence set forth in SEQ ID NO:6.

The at least a first isolated coding regions are those wherein:

(a) the coding sequence is a coding sequence of a DNA molecule present in a bacterial gene library, wherein the DNA molecule hybridizes with a probe having the sequence of the complement of SEQ ID NO:1 under conditions of high stringency; or (b) the coding sequence has a nucleotide sequence degenerate with a sequence according to (a), above.

The invention also provides isolated nucleic acid molecules or segments comprising at least a first isolated coding region that encodes a protein or polypeptide comprising an amino acid sequence that is at least about 85%, 86%, 87%, 88%, 89%, 90%, 91% 92% 93% 94% 95% 96% 97% 98% or 99% or so identical to amino acids 22–349 of the amino acid sequence of SEQ ID NO:2. The encoded proteins and polypeptides are Acinetobacter outer membrane proteins and polypeptides or are able to generate antibodies that cross-react therewith.

Co-owned U.S. Pat. No. 6,074,840 is specifically incorporated herein by reference for purposes of supplementing the present description and enabling teaching concerning isolated nucleic acid molecules that comprise sequences encoding contiguous amino acids sequences; that encode proteins or polypeptides that exhibit at least 90% identity to a given amino acid sequence, wherein the proteins or polypeptides maintain the function of the protein or polypeptide of the given amino acid sequence; and that encode nucleic acid molecules that comprise the nucleotide sequence of a coding sequence of a DNA molecule present in a gene library, wherein the DNA molecule hybridizes with a probe having a given sequence under conditions of high stringency or nucleotide sequences degenerate with such hybridizing sequences.

Exemplary nucleic acid segments of the invention comprise at least a first isolated coding region of at least about 980 nucleotides in length that specifically hybridizes to the nucleotide sequence between nucleotide 1 and about 1050 of SEQ ID NO:1 or an isolated coding region that encodes a protein that comprises at least amino acids 22–349 of the amino acid sequence of SEQ ID NO:2.

Further nucleic acid segments comprise at least a first isolated coding region of at least about 980 nucleotides in length that specifically hybridizes to the nucleotide sequence between nucleotide 63 and about 1050 of SEQ ID NO:1 or an isolated coding region that encodes a protein that comprises at least amino acids 22–349 of the amino acid sequence of SEQ ID NO:2.

Other nucleic acid segments comprise at least a first isolated coding region of at least about 1050 nucleotides in length that specifically hybridizes to the coding region within the nucleotide sequence of SEQ ID NO:1 or to the coding region of the nucleotide sequence set forth in SEQ ID NO:6 or an isolated coding region that encodes a protein comprising an amino acid sequence that is at least about 90% identical to the amino acid sequence of SEQ ID NO:2.

Still further nucleic acid segments comprise at least a first isolated coding region of at least about 1050 nucleotides in length that specifically hybridizes to the nucleotide sequence between nucleotide 1 and about 1050 of SEQ ID NO:1 or an isolated coding region that encodes a protein having the amino acid sequence of SEQ ID NO:2.

Yet other nucleic acid segments comprise at least a first isolated coding region that encodes an Acinetobacter outer membrane protein, wherein the isolated coding region specifically hybridizes to the coding region set forth in the nucleotide sequence of SEQ ID NO:1 or encodes a protein having an amino acid sequence that is at least about 90% identical to the amino acid sequence of SEQ ID NO:2.

The nucleic acid segments also comprise at least a first isolated coding region that encodes an Acinetobacter outer membrane protein, wherein the isolated coding region specifically hybridizes to the nucleotide sequence between nucleotide 1 and about 1050 of the nucleotide sequence of SEQ ID NO:1 or to the coding region of the nucleotide sequence set forth in SEQ ID NO:6 or that encodes a protein having an amino acid sequence that is at least about 95% identical to the amino acid sequence of SEQ ID NO:2.

Certain nucleic acid segments comprise at least a first isolated coding region that encodes an Acinetobacter outer membrane protein, wherein the isolated coding region specifically hybridizes to the nucleotide sequence before the stop codon of SEQ ID NO:1 or encodes a protein comprising the amino acid sequence of SEQ ID NO:2.

Other nucleic acid segments comprise at least a first isolated coding region that encodes an Acinetobacter outer membrane protein A (OMP A), wherein the isolated coding region specifically hybridizes to the nucleotide coding sequence within SEQ ID NO:1 under stringent hybridization conditions or encodes a protein having the amino acid sequence of SEQ ID NO:2.

Certain preferred first isolated coding regions specifically hybridize to the nucleotide sequence of SEQ ID NO:1 under stringent hybridization conditions. Other preferred first isolated coding regions encode a polypeptide or protein having the amino acid sequence of SEQ ID NO:2. The isolated coding regions may have the nucleotide sequence of SEQ ID NO:1 or SEQ ID NO:6. The nucleic acid segments may be RNA or DNA segments.

The nucleic acid segments may further comprise at least a second isolated coding region that encodes a second peptide or protein, such as a second Acinetobacter peptide or protein. Such first isolated coding regions are operatively attached, in frame, to a second coding region that encodes a selected peptide or protein sequence, the nucleic acid segment encoding a fusion protein in which the Acinetobacter outer membrane protein is linked to the selected peptide or protein.

Acinetobacter bacteria that lack a functional endogenous nucleic acid that encodes an outer membrane protein having the amino acid sequence of SEQ ID NO:2 are also provided. Such bacteria include gene knockouts and other forms of genetic inactivation.

The first isolated coding regions are preferably positioned under the control of a promoter. This includes wherein the first isolated coding region is positioned, in reverse orientation, under the control of a promoter that directs the expression of an antisense product.

Thus, the present invention further provides recombinant vectors and recombinant host cells. Exemplary expression vectors comprise at least a first expression unit that comprises a promoter that expresses at least a first isolated coding region that encodes an Acinetobacter outer membrane protein, wherein the isolated coding region specifically hybridizes to the nucleotide sequence of SEQ ID NO:1 or encodes a protein comprising an amino acid sequence that is at least about 85%, 86%, 87%, 88%, 89%, 90%, 91% 92% 93% 94% 95% 96% 97% 98% or 99% or so identical to amino acids 22–349 of the amino acid sequence of SEQ ID NO:2.

The recombinant host cells comprising at least a first exogenous nucleic acid segment that comprises at least a first isolated coding region that encodes an Acinetobacter outer membrane protein, wherein the isolated coding region specifically hybridizes to the nucleotide sequence of SEQ ID NO:1 or encodes a protein comprising an amino acid sequence that is at least about 85%, 86%, 87%, 88%, 89%, 90%, 91% 92% 93% 94% 95% 96% 97% 98% or 99% or so identical to amino acids 22–349 of SEQ ID NO:2. Prokaryotic, eukaryotic and mammalian host cells are included.

The exogenous nucleic acid segment is preferably introduced into the cell by means of a recombinant vector and the host cell preferably expresses the exogenous nucleic acid segment to produce the encoded Acinetobacter outer membrane protein. In certain cases, the at least a first isolated coding region encodes an Acinetobacter outer membrane protein that further comprises sufficient amino acids from amino acids 1–22 of SEQ ID NO:2 to function as a signal peptide.

Method of using a nucleic acid segment that encodes an Acinetobacter outer membrane protein are provided, comprising expressing the nucleic acid segment in a recombinant host cell; wherein the nucleic acid segment comprises at least a first isolated coding region that specifically hybridizes to the nucleotide sequence of SEQ ID NO:1 or that encodes a protein comprising an amino acid sequence that is at least about 85%, 86%, 87%, 88%, 89%, 90%, 91% 92% 93% 94% 95% 96% 97% 98% or 99% or so identical to amino acids 22–349 of SEQ ID NO:2. Met producing an Acinetobacter outer membrane proteins comprise similar process steps.

The methods may further comprise collecting the expressed Acinetobacter outer membrane protein from the host cell. The isolated coding region may encode a protein that is at least about 90% identical to amino acids 1–349 of SEQ ID NO:2 and that is expressed in the outer membrane of the host cell.

Compositions comprising isolated Acinetobacter outer membrane proteins are also provided and comprise an amino acid sequence that is at least about 85%, 86%, 87%, 88%, 89%, 90%, 91% 92% 93% 94% 95% 96% 97% 98% or 99% or so identical to amino acids 22–349 of the amino acid sequence of SEQ ID NO:2. Proteins comprising the amino acid sequence from amino acid 22 to amino acid 349 of SEQ ID NO:2 or the amino acid sequence of SEQ ID NO:2 are preferred. All such proteins may comprise at least a first labeled amino acid or is linked to a detectable labels.

Antigenic peptides of Acinetobacter outer membrane proteins are provided, as exemplified by those comprising the amino acid sequence of GSRTVLAEQPVAQ (amino acids 337–349 of SEQ ID NO:2), DTQHNNNGND (amino acids 36–45 of SEQ ID NO:2), TGNYDSKVKP (amino acids 111–120 of SEQ ID NO:2) or YKYEFEGVPRGTRGNEEEG (amino acids 129–147 of SEQ ID NO:2).

Purified antisera and antibodies are preferred aspects of the present invention. These compositions and components have immunospecificity for an Acinetobacter outer membrane protein that has an amino acid sequence of at least about 85%, 86%, 87%, 88%, 89%, 90%, 91% 92% 93% 94% 95% 96% 97% 98% or 99% or so identity to amino acids 22–349 of SEQ ID NO:2. Polyclonal and monoclonal antibodies are provided, as are and antibodies linked to detectable labels.

First and second nucleic acid primers are also encompassed by the invention, e.g., wherein the primers hybridize to spatially distant sequences from the nucleic acid sequence of SEQ ID NO:1 and are capable of specifically amplifying an Acinetobacter outer membrane protein nucleic acid sequence when used in conjunction with a polymerase chain reaction.

Diagnostic kits of the invention generally comprise a detection reagent in operative association with:

(a) at least a first Acinetobacter outer membrane protein-encoding nucleic acid sequence that specifically hybridizes to the nucleotide sequence of SEQ ID NO:1;

(b) a pair of nucleic acid primers that hybridize to spatially distant sequences from the nucleic acid sequence of SEQ ID NO:1, the primers being capable of specifically amplifying an Acinetobacter outer membrane protein nucleic acid sequence when used in conjunction with a polymerase chain reaction;

(c) a plurality of oligonucleotides that each have a sequence from SEQ ID NO:1, the plurality of oligonucleotides being attached to a solid support and available for hybridization;

(d) at least a first antibody that has immunospecificity for an Acinetobacter outer membrane protein having an amino acid sequence of at least about 85%, 86%, 87%, 88%, 89%, 90%, 91% 92% 93% 94% 95% 96% 97% 98% or 99% or so identity to amino acids 22–349 of SEQ ID NO:2; or (e) an isolated Acinetobacter outer membrane protein comprising an amino acid. sequence of at least about 85%, 86%, 87%, 88%, 89%, 90%, 91% 92% 93% 94% 95% 96% 97% 98% or 99% or so identity to amino acids 22–349 of SEQ ID NO:2.

Nucleic acid detection kits comprise a detection reagent in operative association with at least a first Acinetobacter outer membrane protein-encoding nucleic acid sequence that specifically hybridizes to the nucleotide sequence of SEQ ID NO:1.

The at least a first nucleic acid sequence may be substantially the same length as the coding region within the nucleotide sequence of SEQ ID NO:1. Primers that hybridize to spatially distant sequences from the nucleic acid sequence of SEQ ID NO:1 and that specifically amplify an Acinetobacter outer membrane protein nucleic acid sequence when used in conjunction with a polymerase chain reaction may also be used.

Multiple copies of the at least a first nucleic acid sequence may also be attached to a solid support and available for hybridization. A plurality of oligonucleotides that each have a sequence from SEQ ID NO:1 may also be attached to a solid support and available for hybridization.

As such, the present invention provides sequence detection chips, comprising at least a first Acinetobacter outer membrane protein-encoding nucleic acid sequence from SEQ ID NO:1 attached to a solid support and available for hybridization. The multiple copies of a nucleic acid molecule having the nucleotide sequence from nucleotide 1 to about 1050 of SEQ ID NO:1 are preferably arrayed on the solid support. The plurality of oligonucleotides arrayed on the solid support preferably each have a substantially distinct sequence from SEQ ID NO:1. The plurality of oligonucleotides arrayed on the solid support may also have substantially distinct sequences from SEQ ID NO:1 that overlap by one nucleotide residue per oligonucleotide, such that an overlapping array of SEQ ID NO:1-derived sequences are presented on the solid support.

Immunodetection kits of the invention generally comprise a detection reagent in operative association with an isolated Acinetobacter outer membrane protein that comprises an amino acid sequence of at least about 85%, 86%, 87%, 88%, 89%, 90%, 91% 92% 93% 94% 95% 96% 97% 98% or 99% or so identity to amino acids 22–349 of SEQ ID NO:2 or at least a first antibody that has immunospecificity for the isolated Acinetobacter outer membrane protein. The detection reagent may be operatively associated with or operatively attached to the first antibody; or it may be operatively attached to a second antibody that has immunospecificity for the first antibody.

Antigen compositions comprising biologically effective amounts of at least an isolated Acinetobacter outer membrane protein are provided. The proteins generally comprises an amino acid sequence of at least about 85%, 86%, 87%, 88%, 89%, 90%, 91% 92% 93% 94% 95% 96% 97% 98% or 99% or so identity to amino acids 22–349 of SEQ ID NO:2. Antigenic peptides derived from the Acinetobacter outer membrane protein are also included.

Antigenic cocktails comprise a combined immunogenic amount of an isolated Acinetobacter outer membrane protein that comprises an amino acid sequence of at least about 85%, 86%, 87%, 88%, 89%, 90%, 91% 92% 93% 94% 95% 96% 97% 98% of 99% or so identity to amino acids 22–349 of SEQ ID NO:2, or an antigenic peptide from the Acinetobacter outer membrane protein, and at least a second antigenic component.

The at least a second antigenic component may be an Acinetobacter antigenic component or an *H. pylori* antigenic component, such as an *H. pylori* CagA antigenic component or an *H. pylori* VacA antigenic component. At least one adjuvant may be included.

Vaccine formulations likewise comprise, in a pharmaceutically acceptable form, a therapeutically effective amount of at least an isolated Acinetobacter outer membrane protein that comprises an amino acid sequence of at least about 85%, 86%, 87%, 88%, 89%, 90%, 91% 92% 93% 94% 95% 96% 97% 98% or 99% or so identity to amino acids 22–349 of SEQ ID NO:2, an antigenic peptide from the Acinetobacter outer membrane protein; or an isolated nucleic acid that encodes the Acinetobacter outer membrane protein or an antigenic peptide therefrom.

In terms of methods, the present invention provides methods for detecting a nucleic acid that encodes an Acinetobacter outer membrane protein, comprising contacting sample nucleic acids suspected of containing a nucleic acid that encodes an Acinetobacter outer membrane protein with at least a first isolated nucleic acid that specifically hybridizes to at least a first portion of the nucleotide sequence of SEQ ID NO:1, under conditions effective to allow hybridization of substantially complementary nucleic acids, and detecting the hybridized complementary nucleic acids thus formed.

Methods for detecting an Acinetobacter outer membrane protein comprise contacting a sample suspected of containing an Acinetobacter outer membrane protein with an antibody that has immunospecificity for an Acinetobacter outer membrane protein having an amino acid sequence of at least about 85%, 86%, 87%, 88%, 89%, 90%, 91% 92% 93% 94% 95% 96% 97% 98% or 99% or so identity to amino acids 22–349 of SEQ ID NO:2, under conditions effective to allow the formation of immune complexes, and detecting the immune complexes thus formed.

Methods for identifying the presence of Acinetobacter in a biological sample comprise testing a biological sample suspected of containing Acinetobacter for the presence of a protein with 85%, 86%, 87%, 88%, 89%, 90%, 91% 92% 93% 94% 95% 96% 97% 98% or 99% or so sequence identity to SEQ ID NO:2, wherein the presence of the protein is indicative of a sample that contains Acinetobacter. The presence of the protein may be identified by a molecular biological assay to identify a nucleic acid that encodes the protein; by an immunoassay to identify the protein.

The methods include those for diagnosing a medical or veterinary condition associated with Acinetobacter and comprise testing a biological sample from an animal or human for the presence of a nucleic acid that specifically hybridizes to SEQ ID NO:1, for the presence of a protein with 85%, 86%, 87%, 88%, 89%, 90%, 91% 92% 93% 94% 95% 96% 97% 98% or 99% or so sequence identity to amino acids 22–349 of SEQ ID NO:2, or for the presence of an antibody that has immunospecificity for the protein, wherein the presence of the nucleic acid, protein or antibody is indicative of a medical or veterinary condition associated with Acinetobacter.

In testing for the presence of the nucleic acid segment, the method may comprise the steps of:
(a) contacting nucleic acids of the biological sample with at least a first isolated nucleic acid that specifically hybridizes to at least a first portion of the nucleotide sequence of SEQ ID NO:1, under conditions effective to allow hybridization of substantially complementary nucleic acids; and
(b) detecting the hybridized complementary nucleic acids thus formed.

The nucleic acids may be maintained within the biological sample during contact with the at least a first isolated nucleic acid or separated from the biological sample prior to contact with the at least a first isolated nucleic acid. The nucleic acids of the biological sample may be DNA or RNA.

The at least a first isolated nucleic acid may comprise a radio, enzymatic or fluorescent detectable label and the hybridized complementary nucleic acids may be detected by detecting the label.

Equally, the method may comprise the steps of:
(a) contacting nucleic acids of the biological sample with a pair of nucleic acid primers that specifically hybridize to spatially distant sequences from SEQ ID NO:1, the primers capable of amplifying a nucleic acid segment from SEQ ID NO:1 when used in conjunction with a polymerase chain reaction;
(b) conducting a polymerase chain reaction to create amplification products; and
(c) detecting the amplification products thus formed.

Further methods comprise the steps of:
(a) applying the nucleic acids of the biological sample to a solid support that presents an array of isolated nucleic acids from SEQ ID NO:1, under conditions effective to allow hybridization of substantially complementary nucleic acids; and
(b) detecting the hybridized substantially complementary nucleic acids thus formed.

The solid support may present a repeated array of the nucleic acid sequence of SEQ ID NO:1; or a plurality of oligonucleotides that each have a substantially distinct sequence so that the plurality covers the entire coding region of SEQ ID NO:1.

Where the biological sample is tested for the presence of the protein, the method may comprise the steps of:
(a) contacting the biological sample with at least a first antibody that specifically binds to a protein having at least about 85%, 86%, 87%, 88%, 89%, 90%, 91% 92% 93% 94% 95% 96% 97% 98% or 99% or so identity to SEQ ID NO:2, under conditions effective to allow the formation of immune complexes; and
(b) detecting the immune complexes so formed.

The immune complexes may be detected by a detectable label linked to the first antibody or by a detectable label linked to a second antibody that specifically binds to the first antibody.

Where the biological sample is tested for the presence of the antibody, the methods may comprise the steps of:
(a) contacting the biological sample with a labeled protein having at least about 85%, 86%, 87%, 88%, 89%, 90%, 91% 92% 93% 94% 95% 96% 97% 98% or 99% or so identity to SEQ ID NO:2, under conditions effective to allow the formation of labeled immune complexes; and
(b) detecting the immune complexes so formed by immunoprecipitating the labeled immune complexes.

The biological sample may be a blood, serum, sputum, stool, biopsy or endoscopy sample; e.g., an endoscopic gastric biopsy sample or a sputum or lung biopsy sample.

The biological sample may be obtained from an animal or patient suspected of having a gastrointestinal ulcer, a peptic ulcer; gastrointestinal cancer, such as gastric lymphoma or adenocarcinoma; a more alkaline gastric pH than normal; gastric atrophy or non-*H. pylori* chronic gastritis; a respiratory disorder; pneumonia; meningitis; pernicious anemia or sepsis. The biological sample could be obtained from an immunocompromised patient, such as an immunocompromised patient in preparation for, during or subsequent to a bone marrow or organ transplant, or from a hospitalized patient in ICU.

Methods for diagnosing veterinary or medical conditions associated with Acinetobacter thus comprise determining the amount of an Acinetobacter OMP A component present within a biological sample from an animal or patient suspected of having an Acinetobacter-associated veterinary or medical condition, wherein an increased amount of the OMP A component, in comparison to the amount within a sample from a healthy animal or subject, is indicative of an animal or patient with a veterinary or medical condition associated with Acinetobacter; wherein the Acinetobacter OMP A component is a nucleic acid that specifically hybridizes to the nucleotide sequence of SEQ ID NO:1 or a protein comprising an amino acid sequence of at least about 85%, 86%, 87%, 88%, 89%, 90%, 91% 92% 93% 94% 95% 96% 97% 98% or 99% or so identity to amino acids 22–349 of SEQ ID NO:2.

Treatment methods include those for generating an immune response, comprising administering to an animal a pharmaceutically acceptable composition comprising an immunologically effective amount of an isolated Acinetobacter outer membrane protein of at least about 85%, 86%, 87%, 88%, 89%, 90%, 91% 92% 93% 94% 95% 96% 97% 98% or 99% or so identity to amino acids 22–349 of SEQ ID NO:2; an antigenic peptide from the Acinetobacter outer membrane protein; or an isolated nucleic acid that encodes the Acinetobacter outer membrane protein or an antigenic peptide thereof. Methods wherein the pharmaceutically acceptable composition is administered intravenously are preferred, and adjuvants may be included.

The animal or patient may have, be suspected of having, or be at risk for developing,: a gastrointestinal ulcer, a peptic ulcer; gastrointestinal cancer, such as gastric lymphoma or adenocarcinoma; a more alkaline gastric pH than normal; gastric atrophy or non-*H pylori* chronic gastritis; a respiratory disorder; pneumonia; meningitis; pernicious anemia or sepsis.

The animal or patient may be an immunocompromised animal or patient, such as an immunocompromised patient in preparation for, during or subsequent to a bone marrow or organ transplant, or from a hospitalized patient that is or is at risk for being in critical condition.

As many OMPs have antimicrobial and antibacterial activities, the present invention further provides methods for killing a microorganism, comprising contacting a microorganism with a toxic amount of a composition comprising an isolated Acinetobacter outer membrane protein that is at least about 85%, 86%, 87%, 88%, 89%, 90%, 91% 92% 93% 94% 95% 96% 97% 98% or 99% or so identical to amino acids 22–349 of SEQ ID NO:2. The microorganism may be one that infects the respiratory or gastrointestinal tract.

Non-biomedical compositions and methods of using this invention also exist. In particular, the present invention provides formulations and uses of Acinetobacter OmpA as at least one of the active ingredients in a bioemulsifier or biosurfactant preparation for combating oil slicks and/or for obtaining residuals from oil wells. Although not suggested in the art, the inventor reasons that these compositions and uses are analogous to those of *Pseudomonas aeruginosa*.

Now that the advantageous compositions of the invention have been provided for such use, various technical skills exist in the art for ready application to stabilizing emulsions of high viscosity hydrocarbons, including crude oil and other commercial oil preparations. For example, U.S. Pat. Nos. 6,060,287 and 5,866,376 are specifically incorporated herein by reference for purposes of supplementing the present description and enabling teaching concerning the use of bacterial compositions as biosurfactants.

Accordingly, the invention provides biosurfactant formulations, preferably storage-stable formulations, that comprise at least a first isolated Acinetobacter outer membrane protein that comprises an amino acid sequence of at least about 85%, 86%, 87%, 88%, 89%, 90%, 91% 92% 93% 94% 95% 96% 97% 98% or 99% or so identity to amino acids 22–349 of SEQ ID NO:2, or bioemulsifying portions, domains or peptides thereof. Recombinant proteins or variants are preferred. Apparatus and kits for the application, and preferably, widespread application of such biosurfactant, Acinetobacter outer membrane protein formulations are also provided.

These formulations may be combined with other agents to combat oil spills in the environment, particularly at sea, but also including within soil samples, aquifers and the like. U.S. Pat. Nos. 5,551,987 and 5,128,262 are also specifically incorporated herein by reference for purposes of supplementing the present description and enabling teaching concerning the use of biological agents as biosurfactants for the treatment of mud and oily residues obtained from the processing or extraction of crude oil and for the microbial decontamination of soils contaminated with hydrocarbons and mineral oils.

Methods of the invention therefore include contacting a composition comprising hydrocarbons, mineral oils, high viscosity hydrocarbons and/or high viscosity crude oil with a biologically or environmentally effective amount of a biosurfactant formulation that comprises at least a first isolated Acinetobacter outer membrane protein that comprises an amino acid sequence of at least about 85%, 86%, 87%, 88%, 89%, 90%, 91% 92% 93% 94% 95% 96% 97% 98% or 99% or so identity to amino acids 22–349 of SEQ ID NO:2, or a bioemulsifying portion, domain or peptide thereof.

The "biologically or environmentally effective amount" is an amount of the biosurfactant formulation or Acinetobacter outer membrane protein composition effective to stabilize hydrocarbons, mineral oils, high viscosity hydrocarbons and/or high viscosity crude oil or emulsions thereof, and/or to disperse or remove an inappropriate sample of such unwanted hydrocarbons and oils from an unintended location(s).

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 8A: Number of T and B cells analyzed by flow cytometry of gastric cells isolated from mice inoculated with *H. pylori*. FIG. 8B: Number of T and B cells analyzed by flow cytometry of gastric cells isolated from mice inoculated with Acinetobacter.

FIG. 9A, FIG. 9B, FIG. 9C and FIG. 9D. Flow cytometric analysis was used to analyze the changes in the gastric epithelial cell population. FIG. 9A: Number of G- and D- cells analyzed by flow cytometry of gastric cells isolated from mice inoculated with *H pylori*. FIG. 9B: Number of parietal cells analyzed by flow cytometry of gastric cells isolated from mice inoculated with *H. pylori*. FIG. 9C: Number of G- and D- cells analyzed by flow cytometry of gastric cells isolated from mice inoculated with Acinetobacter. FIG. 9D: Number of parietal cells analyzed by flow cytometry of gastric cells isolated from mice inoculated with Acinetobacter.

FIG. 11A, FIG. 11B and FIG. 11C. Flow cytometric analysis was used to quantify the changes in T cell populations after immunoneutralization of Acinetobacter. The number of CD3+, CD4+, CD8+ and CD8+ expressing IFN-γ cells in mice inoculated with 1:50 (FIG. 11A), 1:500 (FIG. 11B) and 1:5000 (FIG. 11C) dilutions of the pre-immune (PI) and immune (I) serum are compared to uninoculated (UN) mice.

DESCRIPTION OF ILLUSTRATIVE EMBODIMENTS

Figure 1:
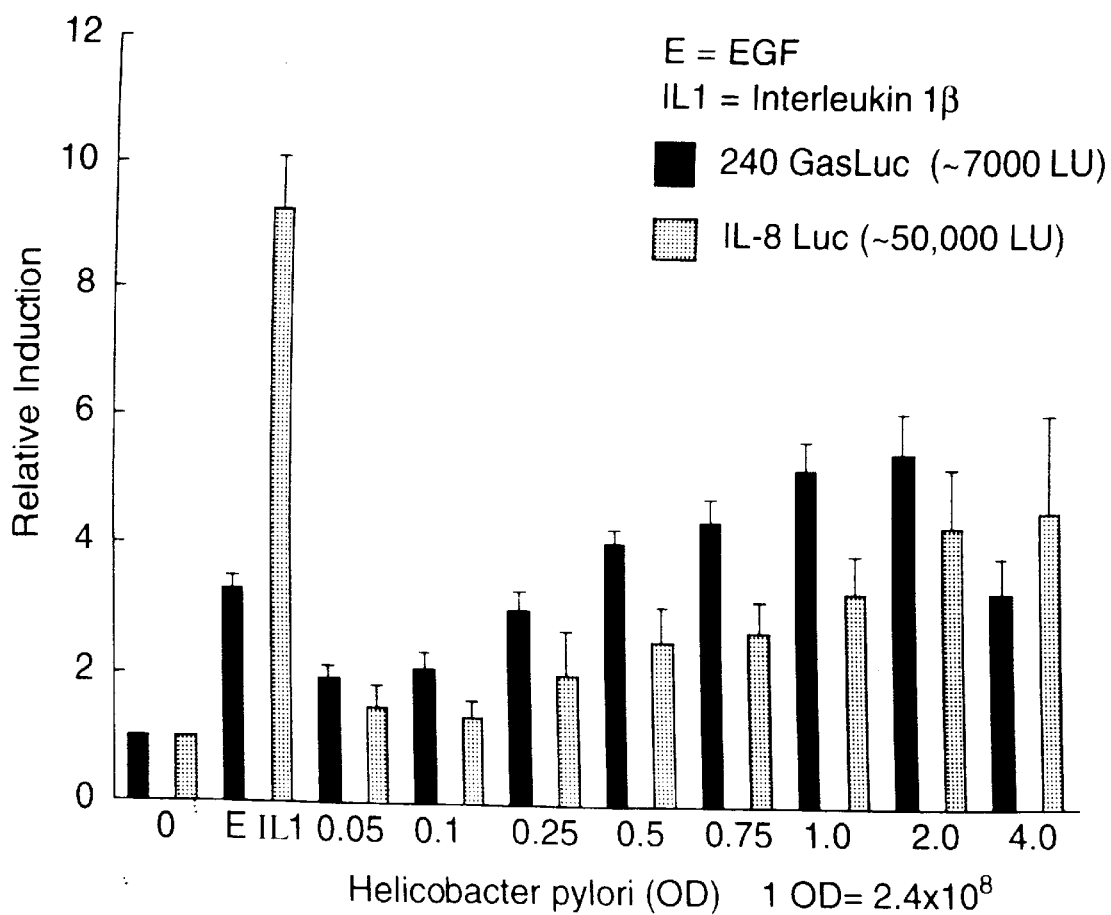
FIG. 1. Co-culture of the bacterial culture with AGS transformants stimulates gastrin and IL-8 promoters. Increasing amounts of the organisms were co-cultured with stable transformants of AGS cells expressing gastrin (solid bars) or IL-8 (stippled bars) promoter constructs. 1 optical density (OD) unit equals $2.4 \times 10^8$ organisms. EGF (E) and IL-1β were used as positive inducers of the gastrin and IL-8 promoters, respectively. The basal luciferase activity for these constructs was ~7,000 light units per µg protein constructs for the gastrin promoter and ~50,000 light units per µg protein for the IL-8 promoter. The mean of the relative induction±standard error (S.E.) for at least 4 studies is shown.

Bacterial overgrowth in the stomach may occur under conditions of diminished or absent acid secretion. Under these conditions, secretion of the hormone gastrin is elevated. Bacterial factors may also directly stimulate gastrin. Under such conditions of increased pH, the flora that colonize the stomach may include opportunistic pathogens. An increase in pH in the stomach may result from achlorhydria, which is also a risk factor for gastric cancer (Seery, 1991). *Klebsiella pneumoniae*, Pseudomonas spp. and *Acinetobacter baumannii* have been cultured from the relatively alkaline stomachs of patients in intensive care (Garrouste-Orgeas et al., 1997). *Acinetobacter baumannii* has been reported to be responsible for 30 nosocomial pneumonias in ventilated patients, despite the use of broad-spectrum antibiotics, e.g., amoxicillin and aminoglycosides.

Gastrin regulates acid secretion and is a growth factor for the oxyntic mucosa (Dockray, 1999). Elevated serum gastrin levels stimulate parietal cell proliferation and acid secretion. Due to the normal feedback regulation of gastrin by acid, achlorhydria is a potent activator of gastrin gene expression (Brand and Stone, 1988). Therefore, overexpression of gastrin has also been implicated as a risk factor for gastric cancer (Wang et al., 2000). Since achlorhydria predisposes the stomach to both colonization by a variety of bacteria as well as hypergastrinemia, the present inventor contemplated that the two conditions were likely related. This provided a framework within which to identify virulence factors in gastric bacterial flora that stimulate both gastrin promoter activity and increase serum gastrin levels.

A microaerophilic culture consisting of Acinetobacter, Pseudomonas and Corynebacteria spp. was inoculated into the mouse stomach for 2–6 months, after which an increase in serum gastrin levels was observed within 2 months. In addition to studying the effect on gastrin, the effect of these organisms on IL-8 gene expression was studied in a cell culture model since it has been shown that *H. pylori* colonization stimulates production of CXC cytokines (e.g., IL-8) from the gastric mucosa (Keates et al., 1997). This cytokine class exhibits potent chemotactic effects that contribute to the inflammatory infiltrate (Moss et al., 1992).

Using a human gastric cell line stably transfected with human gastrin or IL-8 promoters, virulence factors produced by organisms that colonize the stomach were identified. Live cultures of the bacteria were able to stimulate gastrin and IL-8 promoter activity in a dose-dependent manner. The activity was maintained in whole cell sonicates and a heat stable fraction, and heat-stable protein(s) prepared from these bacterial sonicates stimulated the promoter significantly greater than the live organism or unheated sonicates. The promoter stimulating activity was correlated with the major protein in the heat-stable fraction, a 38 kDa heat stable protein.

The 38 kDa protein was N-terminally sequenced and the gene cloned, showing it to be a major outer membrane protein (OMP). Immunoblots using an antibody to this protein identified an Acinetobacter spp. as the bacterial species that expressed this protein and colonized the mouse stomach. Importantly, re-intubation of mice with a pure culture of the Acinetobacter spp. caused gastritis. The Acinetobacter OMP was identified as an OmpA or OmpA-like protein, due to homology with OmpA proteins from other gram negative pathogens. Of the organisms cultured from the mouse stomach, the OmpA-like protein was expressed exclusively in the Acinetobacter strain.

These studies show that bacterial colonization of the stomach increases serum gastrin levels in part through their ability to produce OmpA-like proteins that directly stimulate gastrin and IL-8 gene expression. The present results implicate OmpA-secreting bacteria in the activation of gastrin gene expression and suggest that certain organisms contribute to the increase in serum gastrin and subsequent epithelial cell proliferation in the hypochlorhydric stomach. As the present OmpA-like protein was expressed exclusively in Acinetobacter from all the organisms cultured from the mouse stomach, the data show that Acinetobacter OmpA is an important bacterial factor capable of stimulating gastrin and IL-8 gene expression.

In mouse models and humans, H. pylori is associated with an increase in serum gastrin and gastrin-expressing (G)-cells with a concomitant decrease in somatostatin-expressing D cells. This change appears to follow an increase in interferon-γ expressing Th1 lymphocytes cells. Atrophy of the acid-producing parietal cells leads to metaplastic changes in the stomach. The development of atrophic gastritis leads to decreased colonization by H. pylori and increased colonization by non-H. pylori organisms.

The present invention shows that Acinetobacter causes the same histology as H. pylori on the gastric mucosa. Gastric epithelial cells were isolated by mechanical dissociation. All cell populations were analyzed by flow cytometry. Two months after mice were inoculated with H. pylori or Acinetobacter, the gastric T cell numbers doubled; whereas, an increase in the number of B cells was not observed until 3 months after infection. After 4 months of infection, there was a 3-fold increase in the number of G cells and a doubling in the number of parietal cells. A 3-fold decrease in the number of D-cells occurred in H. pylori and Acinetobacter infected mice. Plasma gastrin and IL-8 levels increased after both H. pylori and Acinetobacter infection. Furthermore, CD4+ cells producing IFN-γ were elevated in the infected mice.

Inflammation and atrophy of the gastric mucosa was observed with both Acinetobacter and H. pylori infection. A PAS/alcian blue stain revealed mucous gland metaplasia of the corpus. Collectively, the results demonstrate that atrophic gastritis and hypergastrinemia is not specific for H. pylori, but rather is the result of other Gram negative bacteria capable of colonizing the stomach. The presence of Acinetobacter, in particular, correlates with atrophic gastritis and hypergastrinemia. Therefore, the identification, cloning and characterization of the 38 kDa surface OMP-A protein from Acinetobacter provides important tools for the ready development of diagnostics and therapeutics for use in patients with peptic ulcers and cancers. The invention also has clinical relevance to patients with low gastric acid secretion, e.g., due to disease such as pernicious anemia, or acid suppressant drugs, as Acinetobacter will have a role in the atrophy and inflammation in such patients.

The present invention also shows that immunoneutralizing OmpA antibodies, such as those raised against the extreme C-terminal domain of the OmpA protein, are able to combat the adverse effects of Acinetobacter. This extends the usefulness of the present discoveries to therapeutic and diagnostic embodiments in all patients and animals infected with Acinetobacter, the clinical and veterinary consequences of which include line sepsis, pneumonia, meningitis and effects in immunocompromised hosts, e.g., bone marrow, liver transplant and cancer patients who are susceptible to infection from this organism.

As gastric colonization by Gram negative bacteria other than H. pylori is common in intensive care patients, who often have an alkaline gastric pH due to routine treatment with antacids, proton pump inhibitors and H2 receptor antagonists, the present invention is ideally suited for diagnosing and treating such patients. Patients with pernicious anemia become colonized by organisms other than H. pylori and develop atrophic gastritis and elevated levels of serum gastrin (Haruma et al., 1995; Lehy et al., 2000; Stockbruegger et al., 1984). Anemic patients may thus be treated with therapeutics based upon the 38 kDa OMP-A of the invention.

Anti-ulcer medications that increase the gastric pH may actually increase the risk of colonization by other pathogens, including Acinetobacter, and thus constitute a risk for the development of nosocomial pneumonia (Garrouste-Orgeas et al., 1997; Torres et al., 1996). The present invention thus has application in this area. Moreover, two weeks of proton pump therapy reduces gastric acidity by 75 percent and is sufficient to permit bacterial colonization of the stomach of healthy or relatively healthy subjects (Example I; Ofori-Darko et al., 2000). As the genera isolated from these stomachs include gram positive and Gram negative organisms, e.g. Neisseria and Acinetobacter, the present invention extends to prophylactic as well as therapeutic uses in such subjects.

I. Nucleic Acid Segments

Important aspects of the present invention thus concern isolated nucleic acid segments and recombinant vectors encoding Acinetobacter OMP A (including wild-type, polymorphic, mutant and second generation OMP As), and the creation and use of recombinant host cells through the application of DNA technology, that express any such OMP A. The nucleic acid segments are generally isolated free from total genomic DNA and are capable of expressing an Acinetobacter OMP A protein, polypeptide or peptide.

The nucleic acid segments of the invention are isolatable from any Acinetobacter strain and may now be easily generated in light of the sequences provided herein. Various Acinetobacter strains are known to be important in human disease. The most important are likely to be *Acinetobacter calcoaceticus-baumannii* complex, *Acinetobacter calcoaceticus* and/or *Acinetobacter baumannii*. Acinetobacter lowffii causes meningitis; whereas an unspeciated strain called Acinetobacter genospecies 11 causes pneumonias.

Other Acinetobacter strains of relevance are Acinetobacter johnsonii, Acinetobacter haemolyticus and *Acinetobacter radioresistens*. Although not typically human pathogens, Acinetobacter junii and Acinetobacter phosphodevorans are encompassed within the invention, particularly in the non-human applications.

As used herein, the terms "nucleic acid segment" and "DNA segment" refer to nucleic acid and DNA molecules that have been isolated free from total genomic nucleic acids or DNA of a particular species. Therefore, a DNA segment encoding Acinetobacter OMP A refers to a DNA segment that contains wild-type, polymorphic, variant or mutant OMP A coding sequences isolated away from, or purified free from, total Acinetobacter genomic nucleic acids or DNA. Included within the terms "nucleic acid and DNA segment", are nucleic acids and DNA segments and smaller fragments of such segments, and also recombinant vectors, including, for example, plasmids, cosmids, phage, viruses, and the like.

A nucleic acid or DNA segment comprising an isolated or purified wild-type, polymorphic, variant or mutant OMP A gene refers to a nucleic acid or DNA segment including coding sequences and, in certain aspects, regulatory sequences, isolated substantially away from other naturally occurring genes or protein encoding sequences. In this respect, the term "gene" is used for simplicity to refer to a functional protein, polypeptide or peptide encoding unit. As will be understood by those in the art, this functional term includes both genomic sequences, cDNA sequences and smaller engineered gene segments that express, or may be adapted to express, proteins, polypeptides, domains, peptides, fusion proteins and mutants. Where "gene" is intended to encompass genomic regulatory or non-coding sequences this will be stated.

"Isolated substantially away from other coding sequences" means that the OMP A nucleic acid or DNA segment forms the significant part of the coding region, and that the overall nucleic acid segment does not contain large portions of naturally-occurring nucleic acids or DNA, such as large chromosomal fragments or other functional genes or cDNA coding regions. Of course, this refers to the nucleic acid or DNA segment as originally isolated, and does not exclude genes or coding regions later added to the segment by the hand of man.

In particular embodiments, the invention concerns isolated nucleic acid and DNA segments and recombinant vectors incorporating nucleic acid sequences that encode an OMP A protein or peptide that includes a contiguous amino acid sequence of at least about 7 or 8 amino acids from SEQ ID NO:2. In other particular embodiments, the invention concerns isolated nucleic acid and DNA segments and recombinant vectors that encode a OMP A protein that includes within its amino acid sequence the substantially full length protein sequence of SEQ ID NO:2 or the substantially full length protein sequence of SEQ ID NO:2 without the signal peptide sequence generally within about amino acids 1–21.

In other embodiments, the invention concerns isolated nucleic acid and DNA segments and recombinant vectors incorporating DNA sequences that encode an OMP A protein or peptide that includes an amino acid sequence essentially as set forth in SEQ ID NO:2. The term "a sequence essentially as set forth in SEQ ID NO:2" means that the sequence substantially corresponds to a portion of SEQ ID NO:2 and has relatively few amino acids that are not identical to, or a biologically functional equivalent of, the amino acids of SEQ ID NO:2.

The term "biologically functional equivalent" is well understood in the art and is further defined in detail herein. Accordingly, sequences of at least about 7, 8, 9 or 10 amino acids in length that have between about 70% and about 80%; or more preferably, between about 81% and about 89%; or more preferably, between about 90% and about 94%; or even more preferably, between about 95% and about 99%; of amino acids that are identical or functionally equivalent to the amino acids of SEQ ID NO:2 will be sequences that are "essentially as set forth in SEQ ID NO:2". Substantially full length sequences (or substantially full length sequences without the 1–21 N-terminal signal sequence) of about 90%, 91%, 92%, 93%, 94%, 95%, 96%, 97%, 98% or 99% sequence identity or functionally equivalency to SEQ ID NO:2 will often be preferred.

It is very much preferred that a structural and/or biological activity of a biologically functional equivalent protein be maintained. Such may be readily determined by any one of a number of functional assays or by the ability to generate an antibody that has immunospecificity for a native OMP A protein or peptide.

In certain other embodiments, the invention concerns isolated DNA segments and recombinant vectors that include within their sequence a nucleic acid sequence essentially as set forth in SEQ ID NO:1. The term "essentially as set forth in SEQ ID NO:1" is used in the same sense as described above and means that the nucleic acid sequence substantially corresponds to a portion of SEQ ID NO:1 and has relatively few codons that are not identical, or functionally equivalent, to the codons of SEQ ID NO:1. The term "functionally equivalent codon" is used herein to refer to codons that encode the same amino acid, such as the six codons for arginine or serine, and also refers to codons that encode biologically equivalent amino acids (see Table A).

TABLE A

| Amino Acids | | | DNA Codons | | | | | |
|---|---|---|---|---|---|---|---|---|
| | | | | | Codons | | | |
| Alanine | Ala | A | GCC | GCT | GCA | GCG | | |
| Cysteine | Cys | C | TGC | TGT | | | | |
| Aspartic acid | Asp | D | GAC | GAT | | | | |
| Glutamic acid | Glu | E | GAG | GAA | | | | |
| Phenylalanine | Phe | F | TTC | TTT | | | | |
| Glycine | Gly | G | GGC | GGG | GGA | GGT | | |
| Histidine | His | H | CAC | CAT | | | | |
| Isoleucine | Ile | I | ATC | ATT | ATA | | | |
| Lysine | Lys | K | AAG | AAA | | | | |
| Leucine | Leu | L | CTG | CTC | TTG | CTT | CTA | TTA |
| Methionine | Met | M | ATG | | | | | |
| Asparagine | Asn | N | AAC | AAT | | | | |
| Proline | Pro | P | CCC | CCT | CCA | CCG | | |
| Glutamine | Gln | Q | CAG | CAA | | | | |
| Arginine | Arg | R | CGC | AGG | CGG | AGA | CGA | CGT |
| Serine | Ser | S | AGC | TCC | TCT | AGT | TCA | TCG |
| Threonine | Thr | T | ACC | ACA | ACT | ACG | | |
| Valine | Val | V | GTG | GTC | GTT | GTA | | |
| Tryptophan | Trp | W | TGG | | | | | |
| Tyrosine | Tyr | Y | TAC | TAT | | | | |

It will also be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of structural and/or functional biological activity, where protein expression is concerned. The addition of terminal sequences as applied to nucleic acid sequences includes, for example, the addition of various regulatory or other non-coding or coding sequences flanking either of the 5' or 3' portions of the coding region.

Excepting flanking regions, and allowing for the degeneracy of the genetic code, sequences that have between about 70% and about 79%; or more preferably, between about 80% and about 89%; or more preferably, between about 90% and about 94%; or even more preferably, between about 95% and about 99%; of nucleotides that are identical to the nucleotides of SEQ ID NO:1 will be sequences that are "essentially as set forth in SEQ ID NO:1". Substantially full length coding sequences of about 90%, 91%, 92%, 93%, 94%, 95%, 96%, 97%, 98% or 99% sequence identity to the nucleotide sequence between nucleotides 1 and about 1050 of SEQ ID NO:1 will often be preferred.

Sequences that are essentially the same as those set forth in SEQ ID NO:1 may also be functionally defined as sequences that are capable of hybridizing to a nucleic acid segment of SEQ ID NO:1 or NO:6 (or containing the complement of SEQ ID NO:1 or NO:6) under appropriately (relatively) stringent conditions. Suitable appropriately or relatively stringent hybridization conditions will be well known to those of skill in the art and are further exemplified herein.

Naturally, the present invention also encompasses DNA segments that are complementary, or essentially complementary, to the sequence set forth in SEQ ID NO:1. Nucleic acid sequences that are "complementary" are those that are capable of base-pairing according to the standard Watson-Crick complementarity rules. As used herein, the term "complementary sequences" means nucleic acid sequences that are substantially complementary, as may be assessed by the same nucleotide comparison set forth above, or as defined as being capable of hybridizing to the nucleic acid segment of SEQ ID NO:1 under relatively stringent conditions such as those described herein.

The nucleic acid segments of the present invention, regardless of the length of the coding sequence itself, may be combined with other nucleic acid and DNA sequences, such as promoters, polyadenylation signals, additional restriction enzyme sites, multiple cloning sites, other coding segments, and the like, such that their overall length may vary considerably. It is therefore contemplated that a nucleic acid segment or fragment of almost any length may be employed, with the total length preferably being limited by the ease of preparation and use in the intended recombinant protocol.

For example, nucleic acid segments or fragments may be prepared that include a short contiguous stretch identical to or complementary to SEQ ID NO:1, such as about a 20 or 21 nucleotide stretch, up to about 20,000, about 10,000, about 5,000 or about 3,000 base pairs in length. Nucleic acid and DNA segments with total lengths of about 1,000, about 500, about 200, about 100 and about 50 base pairs in length (including all intermediate lengths) are also contemplated to be useful.

It will be readily understood that "intermediate lengths", in these contexts, means any length between the quoted ranges, such as 21, 22, 23, 24, 25, etc.; 30, 31, 32, etc.; 50, 51, 52, 53, etc.; 100, 101, 102, 103, etc.; 150, 151, 152, 153, etc.; including all integers through the 200–500; 500–1,000; 1,000–2,000; 2,000–3,000; 3,000–5,000; 5,000–10,000 ranges, up to and including sequences of about 12,001, 12,002, 13,001, 13,002, 15,001, 20,001 and the like.

The various probes and primers designed around the disclosed nucleotide sequences of the present invention may be of any length. For use alone, they will generally include a contiguous stretch of about 20 or 21 nucleotides or so from SEQ ID NO:1. For use as pair or triplets of primers, or as a plurality of sequences from SEQ ID NO:1 (e.g., as arrayed on a sequencing chip), the nucleic acid segments or fragments may include even shorter contiguous stretches from SEQ ID NO:1, such as about a 6, 8, 10, 12, 14, 16, 18 or so nucleotide stretch. By assigning numeric values to a sequence, for example, the first residue is 1, the second residue is 2, etc., an algorithm defining all primers can be proposed:

$n$ to $n+y$ where n is an integer from 1 to the last number of the sequence and y is the length of the primer minus one, where n+y does not exceed the last number of the sequence. Thus, for a 10-mer, the probes correspond to bases 1 to 10, 2 to 11, 3 to 12 . . . and so on. For a 15-mer, the probes correspond to bases 1 to 15, 2 to 16, 3 to 17 . . . and so on. For a 20-mer, the probes correspond to bases 1 to 20, 2 to 21, 3 to 22 . . . and so on.

It will also be understood that this invention is not limited to the particular nucleic acid and amino acid sequences of SEQ ID NO:1 and SEQ ID NO:2. Recombinant vectors and isolated DNA segments may therefore variously include the coding region from SEQ ID NO:1, coding regions bearing selected alterations or modifications in the basic coding region, or they may encode larger polypeptides that nevertheless include such coding regions or may encode biologically functional equivalent proteins or peptides that have variant amino acids sequences.

The nucleic acid and DNA segments of the present invention encompass biologically functional equivalent Acinetobacter OMP A proteins and peptides that arise as a consequence of codon redundancy and functional equivalency that are known to occur naturally within nucleic acid sequences and the proteins thus encoded. Equally, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques, e.g., to introduce improvements to the antigenicity of the protein.

One may also prepare fusion proteins and peptides, e.g., where the OMP A coding regions are aligned within the same expression unit with other proteins or peptides having desired functions, such as for purification or immunodetection purposes (e.g., proteins that may be purified by affinity chromatography and enzyme label coding regions, respectively).

Encompassed by the invention are DNA segments encoding relatively small peptides, such as, for example, peptides of from about 7 or 8, about 10 or 12 or about 15 to about 50 amino acids in length, and more preferably, of from about 12 or 15 to about 30 amino acids in length. Larger polypeptides up to and including proteins corresponding to the full-length sequences set forth in SEQ ID NO:2 are also provided, as are proteins encompassing amino acids 22–349 of SEQ ID NO:2.

II. Recombinant Vectors, Host Cells and Expression

Recombinant vectors form important further aspects of the present invention. The term "recombinant vector, expression vector or construct" mean any type of genetic construct containing a nucleic acid coding for an expressed product in which part or all of the nucleic acid encoding sequence is capable of being transcribed. The transcript may be translated into a protein, but it need not be. Thus, in certain embodiments, "expression" includes both transcription of a nucleic acid segment and translation of an RNA into a gene product. In other embodiments, expression only includes transcription of the nucleic acid, for example, to generate antisense constructs.

Particularly useful vectors are contemplated to be those vectors in which the coding portion of the nucleic acid or DNA segment, whether encoding a full length protein or smaller peptide, is positioned under the transcriptional control of a promoter. A "promoter" refers to a DNA sequence recognized by the synthetic machinery of the cell, or introduced synthetic machinery, required to initiate the specific transcription of a gene. The phrases "operatively positioned", "under control" or "under transcriptional control" mean that the promoter is in the correct location and orientation in relation to the nucleic acid segment to control RNA polymerase initiation and expression of the nucleic acid segment.

The promoter may be in the form of the promoter that is naturally associated with OMP A, as may be obtained by isolating the 5' non-coding sequences located upstream of the coding segment, for example, using recombinant cloning and/or PCR™ technology, in connection with the compositions disclosed herein. PCR™ technology is disclosed in U.S. Pat. No. 4,683,202 and U.S. Pat. No. 4,682,195, each incorporated herein by reference.

In other embodiments, certain advantages will be gained by positioning the coding nucleic acid or DNA segment under the control of a recombinant, or heterologous, promoter. As used herein, a recombinant or heterologous promoter refers to a promoter that is not normally associated with OMP A in its natural environment. Such promoters may include promoters normally associated with other nucleic acids and genes, and/or promoters isolated from any other bacterial, viral, eukaryotic, or mammalian cell.

Naturally, it will be important to employ a promoter that effectively directs the expression of the nucleic acid or DNA segment in the cell type or organism chosen for expression. The use of promoter and cell type combinations for protein expression is generally known to those of skill in the art of molecular biology, for example, see Sambrook et al. (1989; incorporated herein by reference). The promoters employed may be constitutive, or inducible, and can be used under the appropriate conditions to direct high level expression of the introduced nucleic acid or DNA segment, such as is advantageous in the large-scale production of recombinant proteins or peptides.

At least one module in a promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30–110 bp upstream of the start site, although a number of promoters have been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

The particular promoter that is employed to control the expression of a nucleic acid of the invention is not believed to be critical, so long as it is capable of expressing the nucleic acid in the targeted cell. Thus, where a mammalian or human cell is targeted, it is preferable to position the nucleic acid coding region adjacent to and under the control of a promoter that is capable of being expressed in a mammalian or human cell. Generally speaking, such a promoter might include either a mammalian, human or viral promoter. Exemplary promoters include those derived from HSV and tetracycline controlled promoters.

In various other embodiments, the human cytomegalovirus (CMV) immediate early gene promoter, the SV40 early promoter and the Rous sarcoma virus long terminal repeat can be used to obtain high-level expression of transgenes. The use of other viral or mammalian cellular or bacterial phage promoters that are well-known in the art to achieve expression of a transgene are contemplated as well, provided that the levels of expression are sufficient for a given purpose. Virtually any element/promoter may be employed in the context of the present invention to regulate the OMP A protein expression.

Enhancers were originally detected as genetic elements that increased transcription from a promoter located at a distant position on the same molecule of DNA. This ability to act over a large distance had little precedent in classic studies of prokaryotic transcriptional regulation. Subsequent work showed that regions of DNA with enhancer activity are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Additionally any promoter/enhancer combination (as per the Eukaryotic Promoter Data Base EPDB) could also be used to drive expression of a transgene of the invention. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as- an additional genetic expression construct.

As indicated, it is contemplated that one may use any regulatory element to express the OMP A of the present invention. However, under certain circumstances it may be desirable to use the innate promoter region associated with the gene of interest to control its expression, such as the native OMP A promoter. As noted above, in most cases, genes are regulated at the level of transcription by regulatory elements that are located upstream, or 5', to the genes.

In general, to identify regulatory elements for OMP A, one would obtain a genomic DNA segment corresponding to the region located between about 5 to 50 nucleotides up to about 2000 nucleotides or more upstream from the transcriptional start site of the gene. A convenient method used to obtain such a sequence is to utilize restriction enzyme(s) to excise an appropriate DNA fragment. Restriction enzyme technology is commonly used in the art and will be generally known to the skilled artisan. For example, one may use a combination of enzymes from the extensive range of known restriction enzymes to digest the genomic DNA. Analysis of the digested fragments would determine which enzyme(s) produce the desired DNA fragment. The desired region may then be excised from the genomic DNA using the enzyme(s). If desired, one may even create a particular restriction site by genetic engineering for subsequent use in ligation strategies.

Alternatively, one may choose to prepare a series of DNA fragments differentiated by size through the use of a deletion assay with linearized DNA. In such an assay, enzymes are also used to digest the genomic DNA; however, in this case, the enzymes do not recognize specific sites within the DNA but instead digest the DNA from the free end(s). In this case, a series of size differentiated DNA fragments can be achieved by stopping the enzyme reaction after specified time intervals. Of course, one may also choose to use a combination of both restriction enzyme digestion and deletion assay to obtain the desired DNA fragment(s).

Once the desired DNA fragment has been isolated, its potential to regulate a gene and determine the basic regulatory unit may be examined using any one of several conventional techniques. It is recognized that once the core regulatory region is identified, one may choose to employ a longer sequence that comprises the identified regulatory unit. This is because although the core region is all that is ultimately required, it is believed that particular advantages may accrue, in terms of regulation and level of induction achieved, where one employs sequences that correspond to the natural control regions over longer regions. The preferred length will be in part determined by the type of expression system used and the results desired.

Numerous methods are known in the art for precisely locating regulatory units within larger DNA sequences. Most conveniently, the desired control sequence is isolated within a DNA fragment(s) that is subsequently modified using DNA synthesis techniques to add restriction site linkers to the fragment(s) termini. This modification readily allows the insertion of the modified DNA fragment into an expression cassette that contains a reporter gene that confers on its recombinant host cell a readily detectable phenotype that is either expressed or inhibited, as may be the case.

Generally reporter genes encode a polypeptide not otherwise produced by the host cell; or a protein or factor produced by the host cell but at much lower levels; or a mutant form of a polypeptide not otherwise produced by the host cell. Preferably the reporter gene encodes an enzyme that produces a calorimetric, fluorometric or other readily detectable change in the host cell, which is detectable by in situ analysis and is a quantitative or semi-quantitative function of transcriptional activation. Exemplary reporter genes encode esterases, phosphatases, proteases and other proteins detected by activity that generates a chromophore or fluorophore, as will be known to the skilled artisan. Two well-known examples of such reporter genes are $E.$ $coli$ beta-galactosidase and chloramphenicol-acetyl-transferase (CAT). Alternatively, a reporter gene may render its host cell resistant to a selection agent. For example, the gene neo renders cells resistant to the antibiotic neomycin. It is contemplated that virtually any host cell system compatible with the reporter gene cassette may be used to determine the regulatory unit. Thus mammalian or other eukaryotic cells, insect, bacterial or plant cells may be used.

Once a DNA fragment containing the putative regulatory region is inserted into an expression cassette, which is in turn inserted into an appropriate host cell system using any of the techniques commonly known to those of skill in the art, the ability of the fragment to regulate the expression of the reporter gene is assessed. By using a quantitative reporter assay and analyzing a series of DNA fragments of decreasing size, for example produced by convenient restriction endonuclease sites, or through the actions of enzymes such as BAL31, $E.$ $coli$ exonuclease III or mung bean nuclease, and which overlap each other a specific number of nucleotides, one may determine both the size and location of the native regulatory unit.

Of course once the core regulatory unit has been determined, one may choose to modify the regulatory unit by mutating certain nucleotides within the core unit. The effects of these modifications may be analyzed using the same reporter assay to determine whether the modifications either enhance or reduce transcription. Thus key nucleotides within the core regulatory sequence can be identified.

It is recognized that regulatory units often contain both elements that either enhance or inhibit transcription. In the case that a regulatory unit is suspected of containing both types of elements, one may use competitive DNA mobility shift assays to separately identify each element. Those of skill in the art will be familiar the use of DNA mobility shift assays.

It may also be desirable to modify the identified regulatory unit by adding additional sequences to the unit. The added sequences may include additional enhancers, promoters or even other genes. Thus one may, for example, prepare a DNA fragment that contains the native regulatory elements positioned to regulate one or more copies of the native gene and/or another gene or prepare a DNA fragment that contains not one but multiple copies of the promoter region such that transcription levels of the desired gene are relatively increased.

Turning to the expression of OMP A proteins and peptides, once a suitable clone or clones have been obtained, one may proceed to prepare an expression system. The engineering of DNA segment(s) for expression in a prokaryotic or eukaryotic system may be performed by techniques known to those of skill in recombinant expression. It is believed that virtually any expression system may be employed in the expression of the proteins of the present invention.

In expression, one will typically include a polyadenylation signal to effect proper polyadenylation of the transcript. The nature of the polyadenylation signal is not believed to be crucial to the successful practice of the invention, and any such sequence may be employed. The SV40 polyadenylation signal is convenient and is known to function well in various target cells. Also contemplated as an element of the expression cassette is a terminator. These elements can serve to enhance message levels and to minimize read through from the cassette into other sequences.

A specific initiation signal also may be required for efficient translation of coding sequences. These signals include the ATG initiation codon and adjacent sequences. Exogenous translational control signals may be used. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

The OMP As of the present invention may be co-expressed with any other protein or peptide, such as another Acinetobacter antigen. Co-expression may be achieved by co-transfecting the cell with two distinct recombinant vectors, each bearing a copy of either the respective DNA. Alternatively, a single recombinant vector may be constructed to include the coding regions for both of the proteins, which could then be expressed in cells transfected with the single vector. In either event, the term "co-expression" herein refers to the expression of OMP A with another protein or peptide in the same recombinant cell.

As used herein, the terms "engineered" and "recombinant" cells refer to a cell into which an exogenous nucleic acid or DNA segment has been introduced. Therefore, engineered cells are distinguishable from naturally occurring cells, which do not contain a recombinantly introduced exogenous nucleic acid or DNA segment. Engineered cells are thus cells having a nucleic acid or DNA segment introduced through the hand of man. Recombinant cells also include those having an introduced nucleic acid or DNA segment positioned adjacent to a promoter not naturally associated with the particular introduced nucleic acid or DNA segment. Recombinant cells of the present invention also include those in which the Acinetobacter OMP A-encoding sequences have been removed, i.e., "knock-outs".

To express a recombinant OMP A in accordance with the invention one would prepare an expression vector that comprises an OMP A-encoding nucleic acid under the control of one or more promoters. To bring a coding sequence "under the control of" a promoter, one positions the 5' end of the transcription initiation site of the transcriptional reading frame generally between about 1 and about 50 nucleotides "downstream" of (i.e., 3' of) the chosen promoter. The "upstream" promoter stimulates transcription of the DNA and promotes expression of the encoded recombinant protein. This is the meaning of "recombinant expression" in this context.

Many standard techniques are available to construct expression vectors containing the appropriate nucleic acids and transcriptional/translational control sequences in order to achieve protein or peptide expression in a variety of host-expression systems. Cell types available for expression include, but are not limited to, bacteria, such as *E. coli*, Acinetobacter, *H. pylori* and *B. subtilis* transformed with recombinant bacteriophage DNA, plasmid DNA or cosmid DNA expression vectors.

Certain examples of prokaryotic hosts are *E. coli* strain RR1, *E. coli* LE392, *E. coli* B, *E. coli* X 1776 (ATCC No. 31537) as well as *E. coli* W3110 (F-, lambda-, prototrophic, ATCC No. 273325); bacilli such as *Bacillus subtilis*; and other enterobacteriaceae such as *Salmonella typhimurium*, *Serratia marcescens*, and various Pseudomonas species.

In general, plasmid vectors containing replicon and control sequences that are derived from species compatible with the host cell are used in connection with these hosts. The vector ordinarily carries a replication site, as well as marking sequences that are capable of providing phenotypic selection in transformed cells. For example, *E. coli* is often transformed using derivatives of pBR322, a plasmid derived from an *E. coli* species. pBR322 contains genes for ampicillin and tetracycline resistance and thus provides easy means for identifying transformed cells. The pBR plasmid, or other microbial plasmid or phage must also contain, or be modified to contain, promoters which can be used by the microbial organism for expression of its own proteins.

In addition, phage vectors containing replicon and control sequences that are compatible with the host microorganism can be used as transforming vectors in connection with these hosts. For example, the phage lambda GEM™-11 may be utilized in making a recombinant phage vector that can be used to transform host cells, such as *E. coli* LE392.

Further useful vectors include pIN vectors; and pGEX vectors, for use in generating glutathione S-transferase (GST) soluble fusion proteins for later purification and separation or cleavage. Other suitable fusion proteins are those with β-galactosidase, ubiquitin, and the like.

Promoters that are most commonly used in recombinant DNA construction include the β-lactamase (penicillinase), lactose and tryptophan (trp) promoter systems. While these are the most commonly used, other microbial promoters have been discovered and utilized, and details concerning their nucleotide sequences have been published, enabling those of skill in the art to ligate them functionally with plasmid vectors.

The following details concerning recombinant protein production in bacterial cells, such as *E. coli*, are provided by way of exemplary information on recombinant protein production in general, the adaptation of which to a particular recombinant expression system will be known to those of skill in the art.

Bacterial cells, for example, *E. coli*, containing the expression vector are grown in any of a number of suitable media. The expression of the recombinant protein may be induced, e.g., by adding IPTG to the media (if an inducible expression construct is used) or by switching incubation to a higher temperature. After culturing the bacteria for a further period, generally of between 2 and 24 hours, the cells are collected by centrifugation and washed to remove residual media.

The bacterial cells are then lysed, for example, by disruption in a cell homogenizer and centrifuged to separate the dense inclusion bodies and cell membranes from the soluble cell components. This centrifugation can be performed under conditions whereby the dense inclusion bodies are selectively enriched by incorporation of sugars, such as sucrose, into the buffer and centrifugation at a selective speed.

If the recombinant protein is expressed in the inclusion bodies, as is the case in many instances, these can be washed in any of several solutions to remove some of the contaminating host proteins, then solubilized in solutions containing high concentrations of urea (e.g. 8 M) or chaotropic agents such as guanidine hydrochloride in the presence of reducing agents, such as β-mercaptoethanol or DTT (dithiothreitol).

Under some circumstances, it may be advantageous to incubate the protein for several hours under conditions suitable for the protein to undergo a refolding process into a conformation that more closely resembles that of the native protein. Such conditions generally include low protein concentrations, less than 500 mg/ml, low levels of reducing agent, concentrations of urea less than 2 M and often the presence of reagents such as a mixture of reduced and oxidized glutathione which facilitate the interchange of disulfide bonds within the protein molecule.

The refolding process can be monitored, for example, by SDS-PAGE, or with antibodies specific for the native molecule (which can be obtained from animals vaccinated with the native molecule or smaller quantities of recombinant protein). Following refolding, the protein can then be purified further and separated from the refolding mixture by chromatography on any of several supports including ion exchange resins, gel permeation resins or on a variety of affinity columns.

For expression in Saccharomyces, the plasmid YRp7, for example, is commonly used. This plasmid already contains the trpl gene, which provides a selection marker for a mutant strain of yeast lacking the ability to grow in tryptophan, for example ATCC No. 44076 or PEP4-1. The presence of the trpl lesion as a characteristic of the yeast host cell genome then provides an effective environment for detecting transformation by growth in the absence of tryptophan.

Suitable promoting sequences in yeast vectors include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination.

Other suitable promoters, which have the additional advantage of transcription controlled by growth conditions, include the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization.

In addition to micro-organisms, cultures of cells derived from multicellular organisms may also be used as hosts. In principle, any such cell culture is workable, whether from vertebrate or invertebrate culture. In addition to mammalian cells, these include insect cell systems infected with recombinant virus expression vectors (e.g., baculovirus); and plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing OMP A coding sequences.

In a useful insect system, *Autograph californica* nuclear polyhedrosis virus (AcNPV) is used as a vector to express foreign genes. The virus grows in *Spodoptera frugiperda* cells. The OMP A coding sequences are cloned into non-essential regions (for example the polyhedrin gene) of the virus and placed under control of an AcNPV promoter (for example the polyhedrin promoter). Successful insertion of the coding sequences results in the inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed (e.g., U.S. Pat. No. 4,215,051, incorporated herein by reference).

Examples of useful mammalian host cell lines are VERO and HeLa cells, Chinese hamster ovary (CHO) cell lines, W138, BHK, COS-7, 293, HepG2, 3T3, RIN and MDCK cell lines. In addition, a host cell strain may be chosen that modulates the expression of the inserted sequences, or modifies and processes the gene product in the specific fashion desired. Such modifications and processing (e.g., cleavage) of protein products may be important for the function of the protein.

Different host cells have characteristic and specific mechanisms for the post-translational processing and modification of proteins. Appropriate cells lines or host systems can be chosen to ensure the correct modification and processing of the foreign protein expressed.

Expression vectors for use in mammalian such cells ordinarily include an origin of replication (as necessary), a promoter located in front of the gene to be expressed, along with any necessary ribosome binding sites, RNA splice sites, polyadenylation site, and transcriptional terminator sequences. The origin of replication may be provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient. The promoters may be derived from the genome of mammalian cells (e.g., metallothionein promoter) or from mammalian viruses (e.g., the adenovirus late promoter; the vaccinia virus 7.5 K promoter).

A number of viral based expression systems may be utilized, for example, commonly used promoters are derived from polyoma, Adenovirus 2, and most frequently Simian Virus 40 (SV40). The early and late promoters of SV40 virus are particularly useful because both are obtained easily from the virus as a fragment that also contains the SV40 viral origin of replication. Smaller or larger SV40 fragments may also be used, provided there is included the approximately 250 bp sequence extending from the HindIII site toward the BglI site located in the viral origin of replication.

In eukaryotic expression, one will also typically desire to incorporate into the transcriptional unit an appropriate polyadenylation site (e.g., 5'-AATAAA-3') if one was not contained within the original cloned segment. Typically, the poly A addition site is placed about 30 to 2000 nucleotides "downstream" of the termination site of the protein at a position prior to transcription termination.

For long-term, high-yield production of recombinant OMP A, stable expression may be used and cell lines that stably express OMP A may be engineered. Rather than using expression vectors that contain viral origins of replication, host cells can be transformed with vectors controlled by appropriate expression control elements (e.g., promoter, enhancer, sequences, transcription terminators, polyadenylation sites, etc.), and a selectable marker. Following the introduction of foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines.

A number of selection systems may be used, including, but not limited, to the herpes simplex virus thymidine kinase, hypoxanthine-guanine phosphoribosyltransferase and adenine phosphoribosyltransferase genes, in tk-, hgprt- or aprt- cells, respectively. Also, antimetabolite resistance can be used as the basis of selection for dhfr, which confers resistance to methotrexate; gpt, which confers resistance to mycophenolic acid; neo, that confers resistance to the aminoglycoside G-418; and hygro, which confers resistance to hygromycin.

Animal cells can be propagated in vitro in two modes: as non-anchorage dependent cells growing in suspension throughout the bulk of the culture or as anchorage-dependent cells requiring attachment to a solid substrate for their propagation (i.e., a monolayer type of cell growth).

Non-anchorage dependent or suspension cultures from continuous established cell lines are the most widely used means of large scale production of cells and cell products. However, suspension cultured cells have limitations, such as tumorigenic potential and lower protein production than adherent cells.

Large scale suspension culture of mammalian cells in stirred tanks is a common method for production of recombinant proteins. Two suspension culture reactor designs are in wide use—the stirred reactor and the airlift reactor. The stirred design has successfully been used on an 8000 liter capacity for the production of interferon. Cells are grown in a stainless steel tank with a height-to-diameter ratio of 1:1 to 3:1. The culture is usually mixed with one or more agitators, based on bladed disks or marine propeller patterns. Agitator systems offering less shear forces than blades have been described. Agitation may be driven either directly or indirectly by magnetically coupled drives. Indirect drives reduce the risk of microbial contamination through seals on stirrer shafts.

The airlift reactor, also initially described for microbial fermentation and later adapted for mammalian culture, relies on a gas stream to both mix and oxygenate the culture. The gas stream enters a riser section of the reactor and drives circulation. Gas disengages at the culture surface, causing denser liquid free of gas bubbles to travel downward in the downcomer section of the reactor. The main advantage of this design is the simplicity and lack of need for mechanical mixing. Typically, the height-to-diameter ratio is 10:1. The airlift reactor scales up relatively easily, has good mass transfer of gases and generates relatively low shear forces.

It is contemplated that the OMP A proteins of the invention may be "overexpressed", i.e., expressed in increased levels relative to its natural expression in cells. Such overexpression may be assessed by a variety of methods, including radio-labeling and/or protein purification. However, simple and direct methods are preferred, for example, those involving SDS/PAGE and protein staining or western blotting, followed by quantitative analyses, such as densitometric scanning of the resultant gel or blot. A specific increase in the level of the recombinant protein or peptide in comparison to the level in natural cells is indicative of overexpression, as is a relative abundance of the specific protein in relation to the other proteins produced by the host cell and, e.g., visible on a gel.

III. Nucleic Acid Detection

In addition to their use in directing the expression of OMP A proteins and peptides, the nucleic acid sequences of the invention also have a variety of other uses. For example, they also have utility as probes or primers in nucleic acid hybridization and diagnostic embodiments.

A. Hybridization

In general, it is envisioned that the hybridization embodiments of the invention include hybridization in solution, as in PCR™, for detection of expression of corresponding nucleic acids and genes, as well as in embodiments employing a solid phase (nucleic acids adsorbed or affixed to a matrix or solid support). The selected hybridization conditions will depend on the particular circumstances based on the particular criteria required (depending, for example, on the G+C content, type of target nucleic acid, source of nucleic acid, size of hybridization probe, etc.). Following washing of the hybridized surface to remove non-specifically bound probe molecules, hybridization is detected, or even quantified, by means of the label.

The use of a hybridization probe of between about 17–21 and about 100 nucleotides in length allows the formation of a duplex molecule that is both stable and selective. Molecules having complementary sequences over stretches greater than about 20–21 bases in length are generally preferred for straightforward hybridization, in order to increase stability and selectivity of the hybrid, and thereby improve the quality and degree of particular hybrid molecules obtained. However, where a plurality of sequences are arrayed on a sequencing chip, the individual nucleic acid segments may be shorter, e.g., on the order of about 6, 8, 10, 12 or 14 or so nucleotides in length, as the information imparted by these sequencing methods relies on the sequences over the entire array or "chip", not just on one 6-mer or 8-mer.

As used herein, the "hybridization" terminology, methodology and compositions refer to hybridization embodiments other than hybridization using arrays of immobilized probes or sequencing by hybridization (SBH), unless otherwise stated. In more routine hybridization embodiments, one will generally prefer to design nucleic acid molecules having stretches of about 20–21 to about 30 nucleotides, or even longer where desired. Such fragments may be readily prepared by, for example, directly synthesizing the fragment by chemical means or by introducing selected sequences into recombinant vectors for recombinant production.

Accordingly, the nucleotide sequences of the invention may be used for their ability to selectively form duplex molecules with complementary stretches of nucleic acids, DNAs or RNAs or to provide primers for amplification of DNA or RNA. Depending on the application envisioned, one will employ varying conditions of hybridization to achieve varying degrees of selectivity of probe towards target sequence.

For applications requiring high selectivity, one will typically desire to employ relatively stringent hybridization conditions to form the hybrids, e.g., as described herein in Example II. Other appropriately high selectivity and relatively stringent hybridization conditions are provided by relatively low salt and/or high temperature conditions, such as using about 0.02 M to about 0.10 M NaCl at temperatures of about 50° C. to about 70° C. Such high stringency conditions tolerate little, if any, mismatch between the probe and the template or target strand, and are particularly suitable for isolating specific nucleic acids and/or detecting specific mRNA transcripts. It is generally appreciated that conditions can be rendered more stringent by the addition of increasing amounts of formamide.

For certain applications, for example, substitution of nucleotides by site-directed mutagenesis, it is appreciated that lower stringency conditions are required. Under these conditions, hybridization may occur even though the sequences of probe and target strand are not perfectly complementary, but are mismatched at one or more positions. Conditions may be rendered less stringent by increasing salt concentration and decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Thus, hybridization conditions can be readily manipulated depending on the desired results.

In other embodiments, hybridization may be achieved under conditions of, for example, 50 mM Tris-HCl (pH 8.3), 75 mM KCl, 3 mM MgCl$_2$, 1.0 mM dithiothreitol, at temperatures between approximately 20° C. to about 37° C. Other hybridization conditions utilized could include approximately 10 mM Tris-HCl (pH 8.3), 50 mM KCl, 1.5 mM MgCl$_2$, at temperatures ranging from approximately 40° C. to about 72° C.

Certain preferred hybridization conditions are as follows: hybridize immobilized DNA on Hybond N plus overnight at 65° C. in the Church and Gilbert solution comprised of 0.5M Na phosphate, pH 7.2, 7%SDS, 5 mM EDTA. Wash in 2×SSC/0.2%SDS for 5 min at 65° C. 3 times. The signal intensity can be checked initially with a Geiger counter, then on Phosphorimager to test for specific bands. If it is desired to decrease the radioactive background, perform additional washes at 65° C. down to 0.1×SSC and 0.1%SDS. 20×SSC is 175.3 g of NaCl and 88.2 g Na citrate in 1 liter of water pH with NaOH.

In certain embodiments, it will be advantageous to employ nucleic acid sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of being detected. In preferred embodiments, one may desire to employ a fluorescent label or an enzyme tag such as urease, alkaline phosphatase or peroxidase, instead of radioactive or other environmentally undesirable reagents. In the case of enzyme tags, colorimetric indicator substrates are known that can be employed to provide a detection means visible to the human eye or spectrophotometrically, to identify specific hybridization with complementary nucleic acid-containing samples.

B. Amplification and PCR™

Nucleic acid used as a template for amplification is isolated from cells contained in the biological sample, according to standard methodologies (Sambrook et al., 1989; incorporated herein by reference). The nucleic acid may be genomic DNA or fractionated or whole cell RNA. Where RNA is used, it may be desired to convert the RNA to a complementary DNA. In one embodiment, the RNA is whole cell RNA and is used directly as the template for amplification.

The isolated nucleic acid is contacted with at least a pair of primers that selectively hybridize to nucleic acids corresponding to OMP A (e.g., primers that selectively hybridize to distant sequences within SEQ ID NO:1) under conditions that permit selective hybridization. The term "primer", as defined herein, encompasses any nucleic acid that is capable of priming the synthesis of a nascent nucleic acid in a template-dependent (OMP A template-dependent) process. Typically, primers are oligonucleotides from about 10–14 to 20–21 base pairs in length, but longer sequences can be employed. Primers may be provided in double-stranded or single-stranded form, although the single-stranded form is preferred.

Once hybridized, the nucleic acid:primer complex is contacted with one or more enzymes that facilitate template-dependent nucleic acid synthesis. Multiple rounds of amplification, also referred to as "cycles," are conducted until a sufficient amount of amplification product is produced.

Next, the amplification product is detected. In certain applications, the detection may be performed by visual means. Alternatively, the detection may involve indirect identification of the product via chemiluminescence, radioactive scintigraphy of incorporated radiolabel or fluorescent label or even via a system using electrical or thermal impulse signals (Affymax technology).

A number of template dependent processes are available to amplify the marker sequences present in a given template sample. One of the best known amplification methods is the polymerase chain reaction (referred to as PCR™) which is described in detail in U.S. Pat. Nos. 4,683,195, 4,683,202 and 4,800,159, and each incorporated herein by reference in entirety.

Briefly, in PCR™, at least two primer sequences are prepared that are complementary to regions on opposite complementary strands of the marker sequence. Nested primers may also be used. An excess of deoxynucleoside triphosphates is added to a reaction mixture along with a DNA polymerase, e.g., Taq polymerase. If the marker sequence is present in a sample, the primers will bind to the marker and the polymerase will cause the primers to be extended along the marker sequence by adding on nucleotides. By raising and lowering the temperature of the reaction mixture, the extended primers will dissociate from the marker to form reaction products, excess primers will bind to the marker and to the reaction products and the process is repeated.

A reverse transcriptase PCR™ amplification procedure may be performed in order to quantify the amount of mRNA amplified. Methods of reverse transcribing RNA into cDNA are well known and described in Sambrook et al. (1989; incorporated herein by reference). Alternative methods for reverse transcription utilize thermostable, RNA-dependent DNA polymerases. These methods are described in WO 90/07641, incorporated herein by reference. Polymerase chain reaction methodologies are well known in the art.

Another method for amplification is the ligase chain reaction ("LCR"), disclosed in EPA No. 320 308, incorporated herein by reference. In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR™, bound ligated units dissociate from the target and then serve as "target sequences" for ligation of excess probe pairs. U.S. Pat. No. 4,883,750, also incorporated herein by reference, describes a method similar to LCR for binding probe pairs to a target sequence.

Qbeta Replicase, described in PCT Application No. PCT/US87/00880, incorporated herein by reference, may also be used as still another amplification method in the present invention. In this method, a replicative sequence of RNA that has a region complementary to that of a target is added to a sample in the presence of an RNA polymerase. The polymerase will copy the replicative sequence that can then be detected.

An isothermal amplification method, in which restriction endonucleases and ligases are used to achieve the amplification of target molecules that contain nucleotide 5'-[alpha-thio]-triphosphates in one strand of a restriction site may also be useful in the amplification of nucleic acids in the present invention. Restriction amplification may be practiced in context of the present invention, as disclosed in U.S. Pat. No. 5,102,784, incorporated herein by reference.

PCR™, LCR, transcription-based amplification and restriction amplification each require temperature cycling of the reaction between denaturing temperatures (higher) and polymerization temperatures (lower). Methods such as self-sustained sequence replication (3SR), the Qβ replicase system and Strand Displacement Amplification (SDA; U.S. Pat. No. 5,455,166; incorporated herein by reference) are isothermal reactions that are conducted at a constant temperature, which is typically much lower than the reaction temperatures of temperature cycling amplification methods.

Strand Displacement Amplification (SDA) is a method of carrying out isothermal amplification of nucleic acids, which involves multiple rounds of strand displacement and synthesis, i.e., nick translation. A similar method, called Repair Chain Reaction (RCR), involves annealing several probes throughout a region targeted for amplification, followed by a repair reaction in which only two of the four bases are present. The other two bases can be added as biotinylated derivatives for easy detection. A similar approach is used in SDA.

Methods for isothermal Strand Displacement Amplification, which may be performed in a higher temperature range than conventional SDA (about 50° C. to 70° C., "thermophilic SDA"), have also been developed. Thermophilic SDA is described in European Patent Application No. 0 684 315, incorporated herein by reference. This employs thermophilic restriction endonucleases that nick the hemimodified restriction endonuclease recognition/cleavage site at high temperature and thermophilic polymerases that extend from the nick and displace the downstream strand in the same temperature range.

Target specific sequences can also be detected using a cyclic probe reaction (CPR). In CPR, a probe having 3' and 5' sequences of non-specific DNA and a middle sequence of specific RNA is hybridized to DNA that is present in a sample. Upon hybridization, the reaction is treated with RNase H, and the products of the probe identified as distinctive products that are released after digestion. The original template is annealed to another cycling probe and the reaction is repeated.

Still another amplification methods described in GB Application No. 2202328, and in PCT Application No. PCT/US89/01025, each incorporated herein by reference, may be used in accordance with the present invention. In the former application, "modified" primers are used in a PCR™-like, template- and enzyme-dependent synthesis. The primers may be modified by labeling with a capture moiety (e.g., biotin) and/or a detector moiety (e.g., enzyme). In the latter application, an excess of labeled probes is added to a sample. In the presence of the target sequence, the probe binds and is cleaved catalytically. After cleavage, the target sequence is released intact to be bound by excess probe. Cleavage of the labeled probe signals the presence of the target sequence.

Other nucleic acid amplification procedures include transcription-based amplification systems (TAS), including nucleic acid sequence based amplification (NASBA) and 3SR (PCT Application WO 88/10315, incorporated herein by reference). In NASBA, the nucleic acids can be prepared for amplification by standard phenol/chloroform extraction, heat denaturation of a clinical sample, treatment with lysis buffer and minispin columns for isolation of DNA and RNA or guanidinium chloride extraction of RNA. These amplification techniques involve annealing a primer that has target specific sequences. Following polymerization, DNA/RNA hybrids are digested with RNase H while double stranded DNA molecules are heat denatured again. In either case the single stranded DNA is made fully double stranded by addition of second target specific primer, followed by polymerization. The double-stranded DNA molecules are then multiply transcribed by an RNA polymerase such as T7 or SP6. In an isothermal cyclic reaction, the RNA's are reverse transcribed into single stranded DNA, which is then converted to double stranded DNA, and then transcribed once again with an RNA polymerase such as T7 or SP6. The resulting products, whether truncated or complete, indicate target specific sequences.

EPA No. 329 822 (incorporated herein by reference) discloses a nucleic acid amplification process involving cyclically synthesizing single-stranded RNA ("ssRNA"), ssDNA, and double-stranded DNA (dsDNA), which may be used in accordance with the present invention. The ssRNA is a template for a first primer oligonucleotide, which is elongated by reverse transcriptase (RNA-dependent DNA polymerase). The RNA is then removed from the resulting DNA:RNA duplex by the action of ribonuclease H (RNase H, an RNase specific for RNA in duplex with either DNA or RNA). The resultant ssDNA is a template for a second primer, which also includes the sequences of an RNA polymerase promoter (exemplified by T7 RNA polymerase) 5' to its homology to the template. This primer is then extended by DNA polymerase (exemplified by the large "Klenow" fragment of *E. coli* DNA polymerase I), resulting in a double-stranded DNA ("dsDNA") molecule, having a sequence identical to that of the original RNA between the primers and having additionally, at one end, a promoter sequence. This promoter sequence can be used by the appropriate RNA polymerase to make many RNA copies of the DNA. These copies can then re-enter the cycle leading to very swift amplification. With proper choice of enzymes, this amplification can be done isothermally without addition of enzymes at each cycle. Because of the cyclical nature of this process, the starting sequence can be chosen to be in the form of either DNA or RNA.

PCT Application WO 89/06700 (incorporated herein by reference) discloses a nucleic acid sequence amplification scheme based on the hybridization of a promoter/primer sequence to a target single-stranded DNA ("ssDNA") followed by transcription of many RNA copies of the sequence. This scheme is not cyclic, i.e., new templates are not produced from the resultant RNA transcripts. Other amplification methods include "RACE" and "one-sided PCR™" (Frohman, 1990 incorporated by reference).

Methods based on ligation of two (or more) oligonucleotides in the presence of nucleic acid having the sequence of the resulting "di-oligonucleotide", thereby amplifying the di-oligonucleotide, may also be used in the amplification step of the present invention.

Following any amplification, it may be desirable to separate the amplification product from the template and the excess primer for the purpose of determining whether specific amplification has occurred. In one embodiment, amplification products are separated by agarose, agarose-acrylamide or polyacrylamide gel electrophoresis using standard methods (Sambrook et al., 1989; incorporated herein by reference).

Alternatively, chromatographic techniques may be employed to effect separation. There are many kinds of chromatography which may be used in the present invention: adsorption, partition, ion-exchange and molecular sieve, and many specialized techniques for using them including column, paper, thin-layer and gas chromatography. Where microscale reactions are used, e.g., PCR™ on chips, the separation step is also on a microscale.

Amplification products must be visualized in order to confirm amplification of the marker sequences. One typical visualization method involves staining of a gel with ethidium bromide and visualization under UV light. Alternatively, if the amplification products are integrally labeled with radio- or fluorometrically-labeled nucleotides, the amplification products can then be exposed to x-ray film or visualized under the appropriate stimulating spectra, following separation.

In one embodiment, visualization is achieved indirectly. Following separation of amplification products, a labeled, nucleic acid probe is brought into contact with the amplified marker sequence. The probe preferably is conjugated to a chromophore but may be radiolabeled. In another embodiment, the probe is conjugated to a binding partner, such as an antibody or biotin, and the other member of the binding pair carries a detectable moiety.

In one embodiment, detection is by Southern blotting and hybridization with a labeled probe. The techniques involved in Southern blotting are well known to those of skill in the art and can be found in many standard books on molecular protocols (Sambrook et al., 1989; incorporated herein by reference). Briefly, amplification products are separated by gel electrophoresis. The gel is then contacted with a membrane, such as nitrocellulose, permitting transfer of the nucleic acid and non-covalent binding. Subsequently, the membrane is incubated with a chromophore-conjugated probe that is capable of hybridizing with a target amplification product. Detection is by exposure of the membrane to x-ray film or ion-emitting detection devices.

One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

All the essential materials and reagents required for detecting OMP A in a biological sample may be assembled together in a kit. This generally will comprise OMP A sequences, pre-selected OMP A primers, a plurality of OMP A sequences arrayed on a chip, and such like. Also included may be enzymes suitable for amplifying nucleic acids including various polymerases (RT, Taq, etc.), deoxynucleotides and buffers to provide the necessary reaction mixture for amplification. Such kits generally will comprise, in suitable means, distinct containers for each individual reagent and enzyme as well as for each marker primer pair.

The kits may also be formulated onto chips, such as for use in microscale PCR™, or fabricated as a sequencing array, such as for use in SBH (see below). Photolithographic micromachining of silicon (and glass) have been used to construct high-throughput integrated fluidic systems and devices for analysis of nucleic acids. Any of such microfabricated devices may be used in nucleic acid analyses with the present invention. For example, nucleic acids have been successfully amplified by PCR™ and LCR on such microfabricated devices or "chips" (U.S. Pat. Nos. 5,498,392; 5,589,136; 5,639,423; 5,587,128; 5,451,500; and 5,589,136; each incorporated herein by reference). Therefore, where appropriate, the chosen amplification process for use with the invention may be conducted in a reduced scale on such a chip.

C. Other Assays

In addition to conducting standard sequencing on small scales, chips may be used in sequencing by hybridization (SBH) formats. Here, arrays of DNA sequences are attached to glass slides or other solid supports and used to screen and/or sequence other nucleic acids in an automated fashion. Such solid phase hybridization embodiments are now quite routine, and any may be used with the present invention.

In general, the test DNA (or RNA) is adsorbed or otherwise affixed to a selected matrix or surface. These fixed nucleic acids are then subjected to hybridization or "interrogated" with selected probes under desired conditions. The information generated is generally assimilated using computer-based algorithms.

Both Format 1 and Format 2 sequencing is envisioned, as are combinations thereof (WO 95/09248; incorporated herein by reference). The following patents are each incorporated herein by reference for purposes of even further exemplifying SBH: U.S. Pat. Nos. 5,202,231; 5,695,940; 5,525,464; 5,667,972; 5,202,231; 5,492,806; WO 99/09217; and WO 98/31836.

To use SBH with the present invention, multiple copies of the full length OMP A sequence, multiple copies of one or more small, selected oligos, or multiple copies of a range of distinct oligos may be employed. The rapid throughput afforded by SBH makes this ideal for exposing Acinetobacter to different conditions, such as variations in acid, and then screening to identifying genes that may be induced by the conditions.

Other methods for genetic screening to accurately detect mutations in DNA or RNA samples may be employed, depending on the specific situation. Historically, a number of different methods have been used to detect point mutations, including denaturing gradient gel electrophoresis ("DGGE"), restriction enzyme polymorphism analysis, chemical and enzymatic cleavage methods, and others. The more common procedures currently in use include direct sequencing of target regions amplified by PCR™ (see above) and single-strand conformation polymorphism analysis ("SSCP").

Another method of screening for point mutations is based on RNase cleavage of base pair mismatches in RNA/DNA and RNA/RNA heteroduplexes. As used herein, the term "mismatch" is defined as a region of one or more unpaired or mispaired nucleotides in a double-stranded RNA/RNA, RNA/DNA or DNA/DNA molecule. This definition thus includes mismatches due to insertion/deletion mutations, as well as single and multiple base point mutations.

U.S. Pat. No. 4,946,773, incorporated herein by reference, describes an RNase A mismatch cleavage assay that involves annealing single-stranded DNA or RNA test samples to an RNA probe, and subsequent treatment of the nucleic acid duplexes with RNase A. After the RNase cleavage reaction, the RNase is inactivated by proteolytic digestion and organic extraction, and the cleavage products are denatured by heating and analyzed by electrophoresis on denaturing polyacrylamide gels. For the detection of mismatches, the single-stranded products of the RNase A treatment, electrophoretically separated according to size, are compared to similarly treated control duplexes. Samples containing smaller fragments (cleavage products) not seen in the control duplex are scored as positive.

Currently available RNase mismatch cleavage assays, including those performed according to U.S. Pat. No. 4,946,773, require the use of radiolabeled RNA probes. U.S. Pat. No. 4,946,773, incorporated herein by reference, describes the detection of base pair mismatches using RNase A. Other investigators have described the use of *E. coli* enzyme, RNase I, in mismatch assays. Because it has broader cleavage specificity than RNase A, RNase I would be a desirable enzyme to employ in the detection of base pair mismatches if components can be found to decrease the extent of non-specific cleavage and increase the frequency of cleavage of mismatches. The use of RNase I for mismatch detection is described in literature from Promega Biotech. Promega markets a kit containing RNase I that is shown in their literature to cleave three out of four known mismatches, provided the enzyme level is sufficiently high.

The RNase protection assay was first used to detect and map the ends of specific mRNA targets in solution. The assay relies on being able to easily generate high specific activity radiolabeled RNA probes complementary to the mRNA of interest by in vitro transcription. Originally, the templates for in vitro transcription were recombinant plasmids containing bacteriophage promoters. The probes are mixed with total cellular RNA samples to permit hybridization to their complementary targets, then the mixture is treated with RNase to degrade excess unhybridized probe. Also, as originally intended, the RNase used is specific for single-stranded RNA, so that hybridized double-stranded probe is protected from degradation. After inactivation and removal of the RNase, the protected probe (which is proportional in amount to the amount of target mRNA that was present) is recovered and analyzed on a polyacrylamide gel.

The RNase Protection assay was adapted for detection of single base mutations. In this type of RNase A mismatch cleavage assay, radiolabeled RNA probes transcribed in vitro from wild-type sequences, are hybridized to complementary target regions derived from test samples. The test target generally comprises DNA (either genomic DNA or DNA amplified by cloning in plasmids or by PCR™), although RNA targets (endogenous mRNA) have occasionally been used. If single nucleotide (or greater) sequence differences occur between the hybridized probe and target, the resulting disruption in Watson-Crick hydrogen bonding at that position ("mismatch") can be recognized and cleaved in some cases by single-strand specific ribonuclease. To date, RNase A has been used almost exclusively for cleavage of single-base mismatches, although RNase I has recently been shown as useful also for mismatch cleavage. There are recent descriptions of using the MutS protein and other DNA-repair enzymes for detection of single-base mismatches.

D. Mutagenesis

Site-specific mutagenesis is a technique useful in the preparation of individual peptides, or biologically functional equivalent proteins or peptides, through specific mutagenesis of the underlying DNA. The technique further provides a ready ability to prepare and test sequence variants by introducing one or more nucleotide sequence changes into the DNA. U.S. Pat. No. 4,888,286 is specifically incorporated herein by reference to further exemplify such processes.

Site-specific mutagenesis allows the production of mutants through the use of specific oligonucleotide sequences that encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to residues on both sides of the junction of the sequence being altered.

Techniques of site-specific mutagenesis are well known in the art. Certain techniques typically employ a bacteriophage vector that exists in both a single stranded and double stranded form. Typical vectors useful in site-directed mutagenesis include vectors such as the M13 phage. These phage vectors are commercially available and their use is generally well known to those skilled in the art. Double stranded plasmids are also routinely employed in site directed mutagenesis, which eliminates the step of transferring the gene of interest from a phage to a plasmid.

In general, site-directed mutagenesis is performed by first obtaining a single-stranded vector, or melting of two strands of a double stranded vector that includes within its sequence a DNA sequence encoding the desired protein. An oligonucleotide primer bearing the desired mutated sequence is synthetically prepared. This primer is then annealed with the single-stranded DNA preparation, and subjected to DNA polymerizing enzymes such as E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as E. coli cells, and clones are selected that include recombinant vectors bearing the mutated sequence arrangement.

The preparation of sequence variants of OMP A using site-directed mutagenesis described above is provided as a means of producing potentially useful species and is not meant to be limiting, as there are other ways in which sequence variants of OMP A may be obtained. For example, recombinant vectors encoding the desired gene may be treated with mutagenic agents, such as hydroxylamine, to obtain sequence variants.

Although the foregoing methods are suitable for use in mutagenesis, the use of PCR™ is generally now preferred. This technology offers a quick and efficient method for introducing desired mutations into a given DNA sequence. The following text particularly describes the use of PCR™ to introduce point mutations into a sequence, as may be used to change the amino acid encoded by the given sequence. Adaptations of this method are also suitable for introducing restriction enzyme sites into a DNA molecule.

In this method, synthetic oligonucleotides are designed to incorporate a point mutation at one end of an amplified segment. Following PCR™, the amplified fragments are blunt-ended by treating with Klenow fragments, and the blunt-ended fragments are then ligated and subcloned into a vector to facilitate sequence analysis.

To prepare the template DNA that one desires to mutagenize, the DNA is subcloned into a high copy number vector, such as pUC19, using restriction sites flanking the area to be mutated. Template DNA is then prepared using a plasmid miniprep. Appropriate oligonucleotide primers that are based upon the parent sequence, but which contain the desired point mutation and which are flanked at the 5' end by a restriction enzyme site, are synthesized using an automated synthesizer. It is generally required that the primer be homologous to the template DNA for about 15 bases or so. Primers may be purified by denaturing polyacrylamide gel electrophoresis, although this is not absolutely necessary for use in PCR™. The 5' end of the oligonucleotides should then be phosphorylated.

The template DNA should be amplified by PCR™, using the oligonucleotide primers that contain the desired point mutations. The concentration of $MgCl_2$ in the amplification buffer will generally be about 15 mM. Generally about 20–25 cycles of PCR™ should be carried out as follows: denaturation, 35 sec. at 95° C.; hybridization, 2 min. at 50° C.; and extension, 2 min. at 72° C. The PCR™ will generally include a last cycle extension of about 10 min. at 72° C. After the final extension step, about 5 units of Klenow fragments should be added to the reaction mixture and incubated for a further 15 min. at about 30° C. The exonuclease activity of the Klenow fragments is required to make the ends flush and suitable for blunt-end cloning.

The resultant reaction mixture should generally be analyzed by nondenaturing agarose or acrylamide gel electrophoresis to verify that the amplification has yielded the predicted product. One would then process the reaction mixture by removing most of the mineral oils, extracting with chloroform to remove the remaining oil, extracting with buffered phenol and then concentrating by precipitation with 100% ethanol. Next, one should digest about half of the amplified fragments with a restriction enzyme that cuts at the flanking sequences used in the oligonucleotides. The digested fragments are purified on a low gelling/melting agarose gel.

To subclone the fragments and to check the point mutation, one would subclone the two amplified fragments into an appropriately digested vector by blunt-end ligation. This would be used to transform *E. coli*, from which plasmid DNA could subsequently be prepared using a miniprep. The amplified portion of the plasmid DNA would then be analyzed by DNA sequencing to confirm that the correct point mutation was generated. This is important as Taq DNA polymerase can introduce additional mutations into DNA fragments.

The introduction of a point mutation can also be effected using sequential PCR™ steps. In this procedure, the two fragments encompassing the mutation are annealed with each other and extended by mutually primed synthesis. This fragment is then amplified by a second PCR™ step, thereby avoiding the blunt-end ligation required in the above protocol. In this method, the preparation of the template DNA, the generation of the oligonucleotide primers and the first PCR™ amplification are performed as described above. In this process, however, the chosen oligonucleotides should be homologous to the template DNA for a stretch of between about 15 and about 20 bases and must also overlap with each other by about 10 bases or more.

In the second PCR™ amplification, one would use each amplified fragment and each flanking sequence primer and carry PCR™ for between about 20 and about 25 cycles, using the conditions as described above. One would again subclone the fragments and check that the point mutation was correct by using the steps outlined above.

In using either of the foregoing methods, it is generally preferred to introduce the mutation by amplifying as small a fragment as possible. Of course, parameters such as the melting temperature of the oligonucleotide, as will generally be influenced by the GC content and the length of the oligo, should also be carefully considered. The execution of these methods, and their optimization if necessary, will be known to those of skill in the art, and are further described in various publications, such as Current Protocols in Molecular Biology, 1995, incorporated herein by reference.

IV. Proteins and Peptides

A. Proteins

The present invention further provides purified, and in preferred embodiments, substantially purified, OMP A proteins and peptides. The term "purified OMP A protein or peptide" as used herein, is intended to refer to an OMP A proteinaceous composition, isolatable from Acinetobacter or recombinant host cells, wherein the OMP A protein or peptide is purified to any degree relative to its naturally-obtainable state, i.e., relative to its purity within a cellular extract. A purified OMP A protein or peptide therefore also refers to an OMP A protein or peptide free from the environment in which it naturally occurs.

The OMP A proteins may be full length proteins, such as being about 349 amino acids in length. The OMP A proteins, polypeptides and peptides may also be less then full length proteins, such as individual domains, regions or epitopic peptides. Where less than full length OMP A proteins are concerned, certain preferred will be those containing predicted immunogenic sites and those containing functional domains, such as the OMP A-like domain.

Generally, "purified" will refer to an OMP A protein or peptide composition that has been subjected to fractionation to remove various non-OMP A protein or peptide components, and which composition substantially retains its OMP A status, as may be readily assessed by binding to antibodies reactive with native OMP A.

Where the term "substantially purified" is used, this will refer to a composition in which the OMP A protein or peptide forms the major component of the composition, such as constituting about 50% of the proteins in the composition or more. In preferred embodiments, a substantially purified protein will constitute more than 60%, 70%, 80%, 90%, 95% or 99% or so of the proteins in the composition.

An OMP A protein or polypeptide that is "purified to homogeneity," as applied to the present invention, means that the OMP A protein or polypeptide has a level of purity where the OMP A protein or polypeptide is substantially free from other proteins and biological components. For example, a purified OMP A protein or polypeptide will often be sufficiently free of other protein components so that degradative sequencing may be performed successfully.

Various methods for quantifying the degree of purification of OMP A proteins or peptides will be known to those of skill in the art in light of the present disclosure. These include, for example, assessing the number of polypeptides within a fraction by gel electrophoresis, which is a straight-forward technique.

To purify an OMP A protein or peptide, a natural or recombinant composition comprising at least some OMP A proteins or peptides will be subjected to fractionation to remove various non-OMP A components from the composition. Various techniques suitable for use in protein purification are well known to those of skill in the art. These include, for example, precipitation with ammonium sulfate, PEG, antibodies and the like or by heat denaturation, as preferably shown herein, followed by centrifugation; chromatography steps such as ion exchange, gel filtration, reverse phase, hydroxylapatite, lectin affinity and other affinity chromatography steps; isoelectric focusing; gel electrophoresis; and combinations of such and other techniques.

Another specific example is the purification of an OMP A fusion protein using a specific binding partner. Such purification methods are routine in the art. As the present invention provides DNA sequences for OMP A proteins, any fusion protein purification method can now be practiced. This is exemplified by the generation of an OMP A-glutathione S-transferase fusion protein, expression in *E. coli*, and isolation using affinity chromatography on glutathione-agarose.

Although preferred for use in certain embodiments, there is no general requirement that the OMP A protein or peptide always be provided in its most purified state. Indeed, it is contemplated that less substantially purified OMP A proteins or peptides, which are nonetheless enriched in OMP A protein compositions, relative to the natural state, will have utility in certain embodiments. Methods exhibiting a lower degree of relative purification may have advantages in total recovery of protein product, or in maintaining the activity of an expressed protein. For example, antibodies can be generated using less then 100% OMP A, wherein preferably, the resultant antisera would be subsequently screened in an assay using purified OMP A. Inactive products also have utility in certain embodiments, particularly in antibody generation.

B. Epitopic Peptides

Peptides corresponding to one or more antigenic determinants, or "epitopic core regions", of OMP A can also be prepared. Exemplary peptides are described in Example II. Such peptides should generally be at least five or six amino acid residues in length, will preferably be about 8, 10, 12, 15, 20, 25 or about 30 amino acid residues in length, and may contain up to about 35–50 residues or so.

Synthetic peptides will generally be a maximum of about 35 residues long, which is the approximate upper length limit of automated peptide synthesis machines, such as those available from Applied Biosystems (Foster City, Calif.). Longer peptides may also be prepared, e.g., by recombinant means. Recombinant peptides of any desired length may be used.

U.S. Pat. No. 4,554,101 (Hopp), incorporated herein by reference, teaches the identification and preparation of epitopes from primary amino acid sequences on the basis of hydrophilicity. Through the methods disclosed in U.S. Pat. No. 4,554,101, one of skill in the art is able to identify epitopes from within an amino acid sequence such as OMP A (SEQ ID NO:2). Numerous scientific publications have also been devoted to the prediction of secondary structure, and to the identification of epitopes, from analyses of amino acid sequences (Chou & Fasman, 1974a,b; 1978a,b, 1979; each incorporated herein by reference). Any of these may be used, if desired, to supplement the teachings of U.S. Pat. No. 4,554,101.

Moreover, computer programs are currently available to assist with predicting antigenic portions and epitopic core regions of proteins. Examples include those programs based upon the Jameson-Wolf analysis (Jameson & Wolf, 1998; Wolf et al., 1988; each incorporated herein by reference), the program PepPlot® (Brutlag et al., 1990; Weinberger et al., 1985; each incorporated herein by reference), and other new programs for protein tertiary structure prediction (Fetrow & Bryant, 1993; incorporated herein by reference). Further commercially available software capable of carrying out such analyses is termed MacVector (IBI, New Haven, Conn.).

In further embodiments, major antigenic determinants of a polypeptide may be identified by an empirical approach in which portions of the gene encoding the polypeptide are expressed in a recombinant host, and the resulting proteins tested for their ability to elicit an immune response. For example, PCR™ can be used to prepare a range of peptides lacking successively longer fragments of, e.g., the C-terminus of the protein. The immunoactivity of each of these peptides is determined to identify those fragments or domains of the polypeptide that are immunodominant. Further studies in which only a small number of amino acids are removed at each iteration then allows the location of the antigenic determinants of the polypeptide to be more precisely determined.

Another method for determining the major antigenic determinants of a polypeptide is the SPOTs™ system (Genosys Biotechnologies, Inc., The Woodlands, Tex.). In this method, overlapping peptides are synthesized on a cellulose membrane, which following synthesis and deprotection, is screened using a polyclonal or monoclonal antibody. The antigenic determinants of the peptides that are initially identified can be further localized by performing subsequent syntheses of smaller peptides with larger overlaps, and by eventually replacing individual amino acids at each position along the immunoreactive peptide.

Once one or more such analyses are completed, polypeptides are prepared that contain at least the essential features of one or more antigenic determinants. The peptides are then employed in the generation of antisera against the polypeptide. Minigenes or gene fusions encoding these determinants can also be constructed and inserted into expression vectors by standard methods, for example, using PCR™ cloning methodology.

The use of such small peptides for vaccination typically requires conjugation of the peptide to an immunogenic carrier protein, such as hepatitis B surface antigen, keyhole limpet hemocyanin or bovine serum albumin. Methods for performing this conjugation are well known in the art.

C. Biological Functional Equivalents

As modifications and changes may be made in the structure of OMP A nucleic acids and proteins of the present invention, and still obtain molecules having like or otherwise desirable characteristics, such biologically functional equivalents are also encompassed within the present invention.

For example, certain amino acids may be substituted for other amino acids in a protein structure without appreciable loss of interactive binding capacity, for example, peptide signal capacity. Since it is the interactive capacity and nature of a protein that defines that protein's biological functional activity, certain amino acid sequence substitutions can be made in a protein sequence (or, of course, its underlying DNA coding sequence) and nevertheless obtain a protein with like (agonistic) properties. It is thus contemplated that various changes may be made in the sequence of OMP A proteins or peptides, or underlying DNA, without appreciable loss of their biological utility or activity.

In terms of functional equivalents, it is well understood by the skilled artisan that, inherent in the definition of a "biologically functional equivalent protein or peptide or gene", is the concept that there is a limit to the number of changes that may be made within a defined portion of the molecule and still result in a molecule with an acceptable level of equivalent biological activity. Biologically functional equivalent peptides are thus defined herein as those peptides in which certain, not most or all, of the amino acids may be substituted.

In particular, where shorter length peptides are concerned, it is contemplated that fewer amino acid substitutions should be made within the given peptide. Longer proteins and domains may have an intermediate number of changes. The full length protein will have the most tolerance for a larger number of changes. Of course, a plurality of distinct proteins/peptides with different substitutions may easily be made and used in accordance with the invention.

It is also well understood that where certain residues are shown to be particularly important to the biological or structural properties of a protein or peptide, such residues may not generally be exchanged. Maintenance of biological structure/function can always be easily tested though. For example, functional equivalents may be defined as those proteins and peptides that maintain a substantial ability to bind antibodies that bind to the native OMP A (see below).

Amino acid substitutions are generally based on the relative similarity of the amino acid side-chain substituents, for example, their hydrophobicity, hydrophilicity, charge, size, and the like. An analysis of the size, shape and type of the amino acid side-chain substituents reveals that arginine, lysine and histidine are all positively charged residues; that alanine, glycine and serine are all a similar size; and that phenylalanine, tryptophan and tyrosine all have a generally similar shape. Therefore, based upon these considerations, arginine, lysine and histidine; alanine, glycine and serine; and phenylalanine, tryptophan and tyrosine; are defined herein as biologically functional equivalents.

To effect more quantitative changes, the hydropathic index of amino acids may be considered. Each amino acid has been assigned a hydropathic index on the basis of their hydrophobicity and charge characteristics, these are: isoleucine (+4.5); valine (+4.2); leucine (+38); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art (Kyte & Doolittle, 1982, incorporated herein by reference). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those which are within +1 are particularly preferred, and those within ±0.5 are even more particularly preferred.

It is also understood in the art that the substitution of like amino acids can be made effectively on the basis of hydrophilicity, particularly where the biological functional equivalent protein or peptide thereby created is intended for use in immunological embodiments, as in certain embodiments of the present invention. U.S. Pat. No. 4,554,101, incorporated herein by reference, states that the greatest local average hydrophilicity of a protein, as governed by the hydrophilicity of its adjacent amino acids, correlates with its immunogenicity and antigenicity, i.e. with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In making changes based upon similar hydrophilicity values, the substitution of amino acids whose hydrophilicity values are within ±2 is preferred, those which are within ±1 are particularly preferred, and those within ±0.5 are even more particularly preferred.

While discussion has focused on functionally equivalent polypeptides arising from amino acid changes, it will be appreciated that these changes may be effected by alteration of the encoding DNA; taking into consideration also that the genetic code is degenerate and that two or more codons may code for the same amino acid. A table of amino acids and their codons is presented herein for use in such embodiments, as well as for other uses, such as in the design of probes and primers and the like.

One effective method of confirming that a functionally equivalent protein or peptide has retained sufficient OMP A characteristics is to confirm that the equivalent protein or peptide is immunologically cross-reactive with OMP A. Tests of immunological cross-reactivity are a straightforward matter and can be readily determined using specific assays, i.e., based upon competition for binding sites between antibodies and antigens.

Suitable competition assays that may be employed include protocols based upon immunohistochemical assays, ELISAs, RIAs, Western or dot blotting and the like. In any of the competitive assays, one of the binding components, generally the known element, such as the OMP A protein (or even a known antibody) will be labeled with a detectable label. The test components, which generally remain unlabeled, are tested for their ability to reduce the amount of label that is bound to the corresponding reactive antibody or antigen.

As an exemplary embodiment, to conduct a competition study between OMP A and a test antigen or OMP A derivative, one would first label native OMP A with a detectable label, such as, e.g., biotin or an enzymatic, radioactive or fluorogenic label, to enable subsequent identification. One would then incubate the labeled OMP A antigen with the other, test OMP A antigen to be examined at various ratios (e.g., 1:1, 1:10 and 1:100) and, after mixing, one would then add the mixture to a reactive antibody. Preferably, the antibody would be immobilized, e.g., by attaching to an ELISA plate. The ability of the mixture to bind to the antibody would be determined by detecting the presence of the specifically bound label. This value would then be compared to a control value in which no potentially competing (test) antigen was included in the incubation.

The assay may be any one of a range of immunological assays based upon hybridization, and the reactive antigens would be detected by means of detecting their label, e.g., using streptavidin in the case of biotinylated antigens or by using a chromogenic substrate in connection with an enzymatic label or by simply detecting a radioactive or fluorescent label. An antigen that binds to the same antibody as OMP A, for example, will be able to effectively compete for binding to the immobilized antibody and thus will significantly reduce labeled OMP A binding, as evidenced by a reduction in the amount of label detected.

The reactivity of the labeled OMP A antigen in the absence of any test antigen would be the control high value. The control low value would be obtained by incubating the labeled antigen with an excess of unlabeled native OMP A, when competition would occur and reduce binding. A significant reduction in labeled antigen reactivity in the presence of a test antigen is indicative of a test antigen that is "cross-reactive", i.e., that has binding affinity for the same antibody. "A significant reduction", in terms of the present application, may be defined as a reproducible (i.e., consistently observed) reduction in binding.

Such assays may determine precise immunological cross-reactivity, i.e., at the epitope level. Here, a test antigen that competes with labeled OMP A binding to a defined, monoclonal antibody would have at least one epitope that is substantially the same as native OMP A. Such precise assays are generally not necessary. Test antigens that compete with labeled OMP A binding to polyclonal antisera or a range of monoclonal antibodies are identified as having at least one epitope that is substantially the same as an epitope on native OMP A. That is sufficient for cross-reactivity, although a plurality of substantially the same epitopes are expected in functional equivalents.

In addition to the OMP A peptidyl compounds described herein, other sterically similar compounds may be formulated to mimic the key portions of the peptide structure, e.g., to raise cross-reactive antibodies. Such compounds, which may be termed peptidomimetics, may be used in the same manner as the proteins and peptides of the invention and hence are also functional equivalents.

The underlying rationale behind the use of peptide mimetics is that the peptide backbone of proteins exists chiefly to orientate amino acid side chains in such a way as to facilitate molecular interactions, such as those of antibody and antigen. A peptide mimetic is thus designed to permit molecular interactions similar to the natural molecule.

Some successful applications of the peptide mimetic concept have focused on mimetics of β-turns within proteins, which are known to be highly antigenic (Johnson et al., 1993). Likely β-turn structure within a polypeptide can be predicted by computer-based algorithms, as discussed herein. Once the component amino acids of the turn are determined, mimetics can be constructed to achieve a similar spatial orientation of the essential elements of the amino acid side chains.

The generation of further structural equivalents or mimetics may be achieved by the techniques of modeling and chemical design known to those of skill in the art. The art of modeling is now well known, and by such methods a chemical that binds to an OMP A protein can be designed and then synthesized. It will be understood that all such sterically designed constructs fall within the scope of the present invention.

V. Antibodies
A. Antibody Generation

In certain embodiments, the present invention provides antibodies that bind with high specificity to OMP A proteins (SEQ ID NO:2). In addition to antibodies generated against the full length proteins, antibodies may also be generated in response to smaller constructs comprising epitopic core regions, including wild-type, polymorphic and even mutant epitopes.

As used herein, the term "antibody" is intended to refer broadly to any immunological binding agent such as IgG, IgM, IgA, IgD and IgE. Generally, IgG and/or IgM are preferred because they are the most common antibodies in the physiological situation and because they are most easily made in a laboratory setting.

Monoclonal antibodies (MAbs) are recognized to have certain advantages, e.g., reproducibility and large-scale production, and their use is generally preferred. The invention thus provides monoclonal antibodies of the human, murine, monkey, rat, hamster, rabbit and even chicken origin. Due to the ease of preparation and ready availability of reagents, murine monoclonal antibodies will often be preferred.

However, "humanized" antibodies are also contemplated, as are chimeric antibodies from mouse, rat, or other species, bearing human constant and/or variable region domains, bispecific antibodies, recombinant and engineered antibodies and fragments thereof. Methods for the development of antibodies that are "custom-tailored" to the patient's tumor are likewise known and such custom-tailored antibodies are also contemplated.

The term "antibody" is used to refer to any antibody-like molecule that has an antigen binding region, and includes antibody fragments such as Fab', Fab, F(ab')$_2$, single domain antibodies (DABs), Fv, scFv (single chain Fv), and the like. The techniques for preparing and using various antibody-based constructs and fragments are well known in the art.

Means for preparing and characterizing antibodies are well known in the art (See, e.g., Antibodies: A Laboratory Manual, Cold Spring Harbor Laboratory, 1988; incorporated herein by reference).

The methods for generating monoclonal antibodies (MAbs) generally begin along the same lines as those for preparing polyclonal antibodies. Briefly, a polyclonal antibody is prepared by immunizing an animal with an immunogenic OMP A protein or peptide composition in accordance with the present invention and collecting antisera from that immunized animal.

A wide range of animal species can be used for the production of antisera. Typically the animal used for production of anti-antisera is a rabbit, a mouse, a rat, a hamster, a guinea pig or a goat. Because of the relatively large blood volume of rabbits, a rabbit is a preferred choice for production of polyclonal antibodies.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobenzoyl-N-hydroxysuccinimide ester, carbodiimide and bis-biazotized benzidine.

As is also well known in the art, the immunogenicity of a particular immunogen composition can be enhanced by the use of non-specific stimulators of the immune response, known as adjuvants. Suitable adjuvants include all acceptable immunostimulatory compounds, such as cytokines, toxins or synthetic compositions.

Adjuvants that may be used include IL-1, IL-2, IL4, IL-7, IL-12, g-interferon, GMCSP, BCG, aluminum hydroxide, MDP compounds, such as thur-MDP and nor-MDP, CGP (MTP-PE), lipid A, and monophosphoryl lipid A (MPL). RIBI, which contains three components extracted from bacteria, MPL, trehalose dimycolate (TDM) and cell wall skeleton (CWS) in a 2% squalene/Tween 80 emulsion. MHC antigens may even be used.

Exemplary, often preferred adjuvants include complete Freund's adjuvant (a non-specific stimulator of the immune response containing killed *Mycobacterium tuberculosis*), incomplete Freund's adjuvants and aluminum hydroxide adjuvant.

In addition to adjuvants, it may be desirable to coadminister biologic response modifiers (BRM), which have been shown to upregulate T cell immunity or downregulate suppressor cell activity. Such BRMs include, but are not limited to, Cimetidine (CIM; 1200 mg/d) (Smith/Kline, Pa.); or low-dose Cyclophosphamide (CYP; 300 mg/m$^2$) (Johnson/Mead, N.J.) and Cytokines such as γ-interferon, IL-2, or IL-12 or genes encoding proteins involved in immune helper functions, such as B-7.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization.

A second, booster injection, may also be given. The process of boosting and titering is repeated until a suitable titer is achieved. When a desired level of immunogenicity is obtained, the immunized animal can be bled and the serum isolated and stored, and/or the animal can be used to generate MAbs.

For production of rabbit polyclonal antibodies, the animal can be bled through an ear vein or alternatively by cardiac puncture. The removed blood is allowed to coagulate and then centrifuged to separate serum components from whole cells and blood clots. The serum may be used as is for various applications or else the desired antibody fraction may be purified by well-known methods, such as affinity chromatography using another antibody, a peptide bound to a solid matrix, or by using, e.g., protein A or protein G chromatography.

The methods for generating monoclonal antibodies (MAbs) generally begin along the same lines as those for preparing polyclonal antibodies. MAbs may be readily prepared through use of well-known techniques, such as those exemplified in U.S. Pat. No. 4,196,265, incorporated herein by reference. Typically, these techniques involve immunizing a suitable animal with a selected immunogen composition, e.g., a purified or partially purified OMP A protein, polypeptide, peptide or domain. The immunizing composition is administered in a manner effective to stimulate antibody producing cells.

Rodents such as mice and rats are preferred animals, however, the use of rabbit, sheep frog cells is also possible. The use of rats may provide certain advantages (Goding, 1986, pp. 60–61), but mice are preferred, with the BALB/c mouse being most preferred as this is most routinely used and generally gives a higher percentage of stable fusions.

The animals are injected with antigen, generally as described above. The antigen may be coupled to carrier molecules such as keyhole limpet hemocyanin if necessary. The antigen would typically be mixed with adjuvant, such as Freund's complete or incomplete adjuvant. Booster injections with the same antigen would occur at approximately two-week intervals.

Following immunization, somatic cells with the potential for producing antibodies, specifically B lymphocytes (B cells), are selected for use in the MAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible.

Often, a panel of animals will have been immunized and the spleen of animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, pp. 65–66, 1986; Campbell, pp. 75–83, 1984). cites). For example, where the immunized animal is a mouse, one may use P3-X63/Ag8, X63-Ag8.653, NS1/1.Ag 4 1, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with human cell fusions.

One preferred murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line.

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976), and those using polyethylene glycol (PEG), such as 37% (v/v) PEG, by Gefter et al. (1977). The use of electrically induced fusion methods is also appropriate (Goding pp. 71–74, 1986).

Fusion procedures usually produce viable hybrids at low frequencies, about $1 \times 10^{-6}$ to $1 \times 10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody-producing cell lines, which clones can then be propagated indefinitely to provide MAbs. The cell lines may be exploited for MAb production in two basic ways.

A sample of the hybridoma can be injected (often into the peritoneal cavity) into a histocompatible animal of the type that was used to provide the somatic and myeloma cells for the original fusion (e.g., a syngeneic mouse). Optionally, the animals are primed with a hydrocarbon, especially oils such as pristane (tetramethylpentadecane) prior to injection. The injected animal develops tumors secreting the specific monoclonal antibody produced by the fused cell hybrid. The body fluids of the animal, such as serum or ascites fluid, can then be tapped to provide MAbs in high concentration.

The individual cell lines could also be cultured in vitro, where the MAbs are naturally secreted into the culture medium from which they can be readily obtained in high concentrations.

MAbs produced by either means may be further purified, if desired, using filtration, centrifugation and various chromatographic methods such as HPLC or affinity chromatography. Fragments of the monoclonal antibodies of the invention can be obtained from the monoclonal antibodies so produced by methods that include digestion with enzymes, such as pepsin or papain, and/or by cleavage of disulfide bonds by chemical reduction. Alternatively, monoclonal antibody fragments encompassed by the present invention can be synthesized using an automated peptide synthesizer.

It is also contemplated that a molecular cloning approach may be used to generate monoclonals. For this, combinatorial immunoglobulin phagemid libraries are prepared from RNA isolated from the spleen of the immunized animal, and phagemids expressing appropriate antibodies are selected by panning using cells expressing the antigen and control cells. The advantages of this approach over conventional hybridoma techniques are that approximately $10^4$ times as many antibodies can be produced and screened in a single round, and that new specificities are generated by H and L chain combination which further increases the chance of finding appropriate antibodies.

Alternatively, monoclonal antibody fragments encompassed by the present invention can be synthesized using an automated peptide synthesizer, or by expression of full-length gene or of gene fragments in *E. coli*.

B. Antibody Conjugates

The present invention further provides antibodies against OMP A proteins, generally of the monoclonal type, that are linked to one or more other agents to form an antibody conjugate. Any antibody of sufficient selectivity, specificity and affinity may be employed as the basis for an antibody conjugate. Such properties may be evaluated using conventional immunological screening methodology known to those of skill in the art.

Certain examples of antibody conjugates are those conjugates in which the antibody is linked to a detectable label. "Detectable labels" are compounds or elements that can be detected due to their specific functional properties, or chemical characteristics, the use of which allows the antibody to which they are attached to be detected, and further quantified if desired.

Another such example is the formation of a conjugate comprising an antibody linked to a cytotoxic or anti-cellular agent, as may be termed "immunotoxins". In the context of the present invention, immunotoxins are not so preferred as diagnostic conjugates, although immunotoxins could be used in embodiments for killing Acinetobacter and are certainly encompassed as such.

Antibody conjugates are preferred for use as diagnostic agents. Antibody diagnostics generally fall within two classes, those for in vitro diagnostics, such as in a variety of immunoassays, and those in vivo diagnostic protocols, generally known as "antibody-directed imaging". Antibody-directed imaging is less preferred for use with this invention.

Many appropriate imaging agents are known in the art, as are methods for their attachment to antibodies (U.S. Pat. Nos. 5,021,236 and 4,472,509, each incorporated herein by reference). Certain attachment methods involve the use of a metal chelate complex employing, for example, an organic chelating agent such a DTPA attached to the antibody (U.S. Pat. No. 4,472,509). Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate.

In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and erbium (III), with gadolinium being particularly preferred.

Ions useful in other contexts, such as X-ray imaging, include but are not limited to lanthanum (III), gold (III), lead (II), and especially bismuth (III).

In the case of radioactive isotopes for therapeutic and/or diagnostic application, one might mention astatine$^{211}$, $^{14}$carbon, $^{51}$chromium, $^{36}$chlorine, $^{57}$cobalt, $^{58}$cobalt, copper$^{67}$, $^{152}$Eu, gallium$^{67}$, $^{3}$hydrogen, iodine$^{123}$, iodine$^{125}$, iodine$^{131}$, indium$^{111}$, $^{59}$iron, $^{32}$phosphor, rhenium$^{186}$, rhenium$^{188}$, $^{75}$selenium, $^{35}$sulphur, technicium$^{99m}$ and yttrium$^{90}$. $^{125}$I is often being preferred for use in certain embodiments, and technicium$^{99m}$ and indium$^{111}$ are also often preferred due to their low energy and suitability for long range detection.

Radioactively labeled monoclonal antibodies of the present invention may be produced according to well-known methods in the art. For instance, monoclonal antibodies can be iodinated by contact with sodium or potassium iodide and a chemical oxidizing agent such as sodium hypochlorite, or an enzymatic oxidizing agent, such as lactoperoxidase. Monoclonal antibodies according to the invention may be labeled with technetium-$^{99m}$ by ligand exchange process, for example, by reducing pertechnate with stannous solution, chelating the reduced technetium onto a Sephadex column and applying the antibody to this column or by direct labeling techniques, e.g., by incubating pertechnate, a reducing agent such as SNCl$_2$, a buffer solution such as sodium-potassium phthalate solution, and the antibody.

Intermediary functional groups that are often used to bind radioisotopes that exist as metallic ions to antibody are diethylenetriaminepentaacetic acid (DTPA) and ethylene diaminetetracetic acid (EDTA).

Fluorescent labels include rhodamine, fluorescein isothiocyanate and renographin.

Preferred antibody conjugates of the present invention are those intended primarily for use in vitro, where the antibody is linked to a secondary binding ligand or to an enzyme (an enzyme tag) that will generate a colored product upon contact with a chromogenic substrate. Examples of suitable enzymes include urease, alkaline phosphatase, (horseradish) hydrogen peroxidase and glucose oxidase. Preferred secondary binding ligands are biotin and avidin or streptavidin compounds. The use of such labels is well known to those of skill in the art and is described, for example, in U.S. Pat. Nos. 3,817,837; 3,850,752; 3,939,350; 3,996,345; 4,277,437; 4,275,149 and 4,366,241; each incorporated herein by reference.

VI. Immunodetection Methods

In still further embodiments, the present invention provides immunodetection methods for binding, purifying, removing, quantifying or otherwise generally detecting OMP A biological components. The OMP A proteins and peptides of the invention may be employed to detect and purify OMP A antibodies, such as those prepared in accordance herewith and those present in patients' sera. Equally, OMP A-specific antibodies may be used to purified OMP A and OMP A in Acinetobacter. The steps of various useful immunodetection methods have been described in the scientific literature, such as, e.g., Nakamura et al. (1987), incorporated herein by reference.

As at least a sub-set of patients infected with Acinetobacter will likely generate antibodies to the OMP A proteins, the detection of antibodies within the patients' sera is a valid diagnostic test (although the detection of OMP A itself will often be preferred). As well as variations of the typical binding assays described below, in which OMP A is immobilized and used to detect anti-OMP A antibodies, immunoprecipitation may also be used. Here, labeled OMP A proteins are admixed with sera and any immune complexes formed are immunoprecipitated to facilitate detection.

Certain immunobinding methods include obtaining a sample suspected of containing an OMP A protein or peptide, and contacting the sample with a first anti-OMP A antibody, under conditions effective to allow the formation of immunocomplexes. These methods include methods for purifying OMP A, as may be employed in purifying wild-type or recombinantly expressed OMP A. In these instances, the antibody removes the OMP A component from a sample.

Thus, the antibody may preferably be linked to a solid support, such as in the form of a column matrix, wherein the sample suspected of containing OMP A will be applied to the immobilized antibody. The unwanted components will be washed from the column, leaving the OMP A immunocomplexed to the immobilized antibody. OMP A is then collected by removing the OMP A protein from the column.

The immunobinding methods also include methods for detecting or quantifying the amount of an OMP A component in a sample, which methods require the detection or quantification of any immune complexes formed during the binding process. Here, one would generally obtain a sample suspected of containing an OMP A and contact the sample with an antibody against OMP A, and then detect or quantify the amount of immune complexes formed under the specific conditions.

In terms of antigen detection, the biological sample analyzed may be any sample that is suspected of containing an OMP A antigen, or Acinetobacter organisms containing such OMP As. Such samples include gastrointestinal tissue sections or specimens and homogenized tissue extracts. Preferably, biological byproducts and fluids that come into contact with the gastrointestinal tissues (preferably the stomach and duodenum) will be used. Blood and serum are generally preferred, although stool samples can be employed.

Contacting the chosen biological sample with the antibody under conditions effective and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to, any OMP A present. After this time, the sample-antibody composition, such as a tissue section, ELISA plate, dot blot or western blot, will generally be washed to remove any non-specifically bound antibody species, allowing only those antibodies specifically bound within the primary immune complexes to be detected.

In general, the detection of immunocomplex (immune complex) formation is well known in the art and may be achieved through the application of numerous approaches. These methods are generally based upon the detection of a label or marker, such as any of those radioactive, fluorescent, biological or enzymatic tags. U.S. Patents concerning the use of such labels include U.S. Pat. Nos. 3,817,837; 3,850, 752; 3,939,350; 3,996,345; 4,277,437; 4,275,149 and 4,366, 241, each incorporated herein by reference. Of course, one may find additional advantages through the use of a secondary binding ligand such as a second antibody or a biotin/avidin ligand binding arrangement, as is known in the art.

The OMP A-binding antibody employed in the detection may itself be linked to a detectable label, wherein one would then simply detect this label, thereby allowing the amount of the primary immune complexes in the composition to be determined.

Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under conditions effective and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two step approach. A second binding ligand, such as an antibody, that has binding affinity for the antibody is used to form secondary immune complexes, as described above. After washing, the secondary immune complexes are contacted with a third binding ligand or antibody that has binding affinity for the second antibody, again under conditions effective and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

The immunodetection methods of the present invention have evident utility in the diagnosis or prognosis of medical conditions associated with Acinetobacter (e.g., gastric and duodenal ulcers; gastrointestinal cancers; respiratory disorders; pneumonia; meningitis; pernicious anemia and/or sepsis). However, immunodetection embodiments also have applications to non-clinical samples, such as in the titering of antigen or antibody samples, in the selection of hybridomas, and the like.

In addition to ELISAs (see below), the antibodies of the present invention may also be used diagnostically in conjunction with both fresh-frozen and formalin-fixed, paraffin-embedded tissue blocks prepared for study by immunohistochemistry (IHC). The tissue blocks may consists of residual "pulverized" tissue. Methods of preparing tissue blocks from specimens and methods of immunohistochemistry are well known to those of skill in the art.

A. ELISAs

As detailed above, immunoassays, in their most simple and direct sense, are binding assays. Certain preferred immunoassays are the various types of enzyme linked immunosorbent assays (ELISAs) and radioimmunoassays (RIA) known in the art. Immunohistochemical detection using tissue sections is also particularly useful. However, it will be readily appreciated that detection is not limited to such techniques, and Western blotting, dot blotting, FACS analyses, and the like may also be used.

In one exemplary ELISA, the OMP A antibodies of the invention are immobilized onto a selected surface exhibiting protein affinity, such as a well in a polystyrene microtiter plate. Then, a test composition suspected of containing OMP A, such as a clinical sample, is added to the wells. After binding and washing to remove non-specifically bound immune complexes, the bound OMP A antigen may be detected. Detection is generally achieved by the addition of another OMP A antibody that is linked to a detectable label. This type of ELISA is a simple "sandwich ELISA". Detection may also be achieved by the addition of a second anti-OMP A antibody, followed by the addition of a third antibody that has binding affinity for the second antibody, with the third antibody being linked to a detectable label.

In another exemplary ELISA, the samples suspected of containing the OMP A antigen are immobilized onto the well surface and then contacted with the anti-OMP A antibodies of the invention. After binding and washing to remove non-specifically bound immune complexes, the bound anti-OMP A antibodies are detected. Where the initial anti-OMP A antibodies are linked to a detectable label, the immune complexes may be detected directly. Again, the immune complexes may be detected using a second antibody that has binding affinity for the first anti-OMP A antibody, with the second antibody being linked to a detectable label.

Another ELISA in which the OMP A proteins or peptides are immobilized, involves the use of antibody competition in the detection. In this ELISA, labeled antibodies against OMP A are added to the wells, allowed to bind, and detected by means of their label. The amount of OMP A in an unknown sample is then determined by mixing the sample with the labeled anti-OMP A antibodies before or during incubation with coated wells. The presence of OMP A in the sample acts to reduce the amount of antibody against OMP A available for binding to the well and thus reduces the ultimate signal. This is also appropriate for detecting antibodies against OMP A in an unknown sample, where the unlabeled antibodies bind to the antigen-coated wells and also reduce the amount of antigen available to bind the labeled antibodies.

Irrespective of the format employed, ELISAs have certain features in common, such as coating, incubating or binding, washing to remove non-specifically bound species, and detecting the bound immune complexes. These are described as follows:

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein and solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the biological sample to be tested under conditions effective to allow immune complex (antigen/antibody) formation. Detection of the immune complex then requires a labeled secondary binding ligand or antibody, or a secondary binding ligand or antibody in conjunction with a labeled tertiary antibody or third binding ligand.

"Under conditions effective to allow immune complex (antigen/antibody) formation" means that the conditions preferably include diluting the antigens and antibodies with solutions such as BSA, bovine gamma globulin (BGG) and phosphate buffered saline (PBS)/Tween. These added agents also tend to assist in the reduction of nonspecific background.

The "suitable" conditions also mean that the incubation is at a temperature and for a period of time sufficient to allow effective binding. Incubation steps are typically from about 1 to 2 to 4 hours, at temperatures preferably on the order of 25° C. to 27° C., or may be overnight at about 4° C. or so.

Following all incubation steps in an ELISA, the contacted surface is washed so as to remove non-complexed material. A preferred washing procedure includes washing with a solution such as PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. Preferably, this will be an enzyme that will generate color development upon incubating with an appropriate chromogenic substrate. Thus, for example, one will desire to contact and incubate the first or second immune complex with a urease, glucose oxidase, alkaline phosphatase or hydrogen peroxidase-conjugated antibody for a period of time and under conditions that favor the development of further immune complex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea and bromocresol purple or 2,2'-azino-di-(3-ethyl-benzthiazoline-6-sulfonic acid [ABTS] and $H_2O_2$, in the case of peroxidase as the enzyme label. Quantification is then achieved by measuring the degree of color generation, e.g., using a visible spectra spectrophotometer.

B. Immunodetection Kits

In still further embodiments, the present invention provides immunodetection kits for use with the immunodetection methods described above. As the OMP A antibodies are generally used to detect OMP A, the antibodies will preferably be included in the kit. However, kits including both such components may be provided. The immunodetection kits will thus comprise, in suitable container means, at least a first antibody that binds to OMP A, and optionally, an immunodetection reagent and further optionally, an OMP A protein or peptide.

In preferred embodiments, monoclonal antibodies will be used. In certain embodiments, the first antibody that binds to OMP A may be pre-bound to a solid support, such as a column matrix or well of a microtiter plate.

The immunodetection reagents of the kit may take any one of a variety of forms, including those detectable labels that are associated with or linked to the given antibody. Detectable labels that are associated with or attached to a secondary binding ligand are also contemplated. Exemplary secondary ligands are those secondary antibodies that have binding affinity for the first antibody.

Further suitable immunodetection reagents for use in the present kits include the two-component reagent that comprises a secondary antibody that has binding affinity for the first antibody, along with a third antibody that has binding affinity for the second antibody, the third antibody being linked to a detectable label. As noted above, a number of exemplary labels are known in the art and all such labels may be employed in connection with the present invention.

The kits may further comprise a suitably aliquoted composition of OMP A, whether labeled or unlabeled, as may be used to prepare a standard curve for a detection assay.

The kits may contain antibody-label conjugates either in fully conjugated form, in the form of intermediates, or as separate moieties to be conjugated by the user of the kit. The components of the kits may be packaged either in aqueous media or in lyophilized form.

The container means of the kits will generally include at least one vial, test tube, flask, bottle, syringe or other container means, into which the antibody may be placed, and preferably, suitably aliquoted. Where OMP A proteins or second or third binding ligands or additional components are provided, the kit will also generally contain a second, third or other additional container into which such components may be placed. The kits of the present invention will also typically include a means for containing the antibody, antigen, and any other reagent containers in close confinement for commercial sale. Such containers may include injection or blow-molded plastic containers into which the desired vials are retained.

VII. Diagnostics

Certain of the diagnostic methods of the present invention are based upon the evidence of the importance of Acinetobacter infection in gastric disorders, such as gastritis, duodenal and gastric ulcers and gastrointestinal cancers. Other diagnostic aspects include those in relation to respiratory disorders, pneumonia, meningitis, pernicious anemia, sepsis and in connection with immunocompromised and transplant patients and those in ICU. The diagnostic methods of the invention generally involve determining either the presence or the amount of an OMP A protein (or OMP A-containing Acinetobacter) in a biological sample from a patient suspected of having any such condition or disease.

Irrespective of the actual role of Acinetobacter, and/or OMP A, it will be understood that the detection of OMP A is diagnostic for the foregoing conditions. OMP A may be detected as a protein or anti-OMP A antibodies may be detected. OMP A may also be identified at the nucleic acid level. The finding of an increased amount of OMP A protein, anti-OMP A antibodies or OMP A nucleic acids, in comparison to the amount within a sample from a normal subject, will be indicative of a patient with such a gastrointestinal, respiratory or other condition or disease connected with Acinetobacter infection.

The amount of OMP A protein present within a biological sample, such as a blood, stool, sputum or tissue sample, may be determined by means of a molecular biological assay to determine the level of a nucleic acid that encodes such an OMP A, or by means of an immunoassay to determine the level of the polypeptide itself. Any of the foregoing nucleic acid detection methods or immunodetection methods may be employed as diagnostic methods in the context of the present invention.

However, as is known to those of skill in the art, such a clinical diagnosis would not necessarily be made on the basis of this method in isolation. Those of skill in the art are very familiar with differentiating between significant differences in types or amounts of biomarkers, which represent a positive identification, and low level or background changes of biomarkers. Indeed, background expression levels are often used to form a "cut-off" above which increased detection will be scored as significant or positive.

The foregoing nucleic acid and immunodetection methods will also have evident utility in prognostic embodiments and in monitoring the success of therapies to eradicate Acinetobacter infection. All such diagnostic and prognostic uses may be applied to gastrointestinal conditions, such as peptic ulcers (gastric and duodenal) and gastrointestinal cancers and to respiratory and other conditions mentioned above.

In monitoring the success of therapies against Acinetobacter infection or colonization, the lack of detection of OMP A, or a decrease in the levels of OMP A in comparison to the levels in a corresponding biological sample prior to therapy, is indicative of a patient that is being successfully treated for the gastrointestinal condition associated with Acinetobacter infection or colonization.

The biological samples suspected of containing Acinetobacter may also be exposed to conditions that are known, or believed, to be capable of modifying Acinetobacter gene expression, i.e., conditions that alter the profile of proteins expressed by Acinetobacter. Currently preferred amongst such variable conditions is pH. In addition to ensuring workable or optimal conditions for conducting diagnostic tests, such methodology is also of use in eliciting further antigens for analysis and in understanding the pathogenesis of Acinetobacter infection.

VIII. Therapeutics

As OMP A proteins are expressed at the cell surface, further embodiments of the invention concern the use of such proteins and peptides in immunological-based therapies for the prevention or treatment of Acinetobacter infections and associated gastrointestinal, respiratory and other conditions. The treatment of patients with pneumonia, meningitis, pernicious anemia and sepsis is particularly contemplated, as is the treatment of immunocompromised and transplant patients and those in ICU. In fact, the stomach serves as a reservoir for organisms that are aspirated causing respiratory disease in ventilated patients, so such patients will particularly benefit from application of the present invention.

Since Acinetobacter is a major cause of a variety of hospital-based infectious diseases, the present invention is particularly useful in preparing a vaccine for use in situations in which the antibody is not required to cross an epithelial cell barrier to be effective. In cases of sepsis, where the immune response generated is readily accessible to the organisms, antibody against Acinetobacter OmpA appears to be quite effective.

Therefore, the invention also encompasses OMP A protein or peptide (antigen) and/or nucleic acid compositions, or "vaccines", preferably formulated with pharmaceutically acceptable carriers, diluents and/or adjuvants. Other formulations, vaccines or "antigenic cocktails" are also provided, comprising additional components, such as antigens or even outer membrane preparations, as are often employed in the formulation of vaccines.

Although more refined vaccination components will generally be preferred, the preparation of Acinetobacter outer membrane vesicles that contain OMP A could also be as the basis for a human vaccine, so long as the vesicles are not significantly toxic. The preparation of vesicles that are essentially free from endotoxin and LPS can be achieved, for example, see U.S. Pat. No. 4,271,147, incorporated herein by reference.

The present invention thus also provides methods of generating an immune response, which methods generally comprise administering to an animal, including a human subject, a pharmaceutically acceptable composition comprising an immunologically effective amount of an OMP A protein, peptide or nucleic acid composition. The composition may include partially or significantly purified OMP A proteins or peptides, obtained from natural or recombinant sources. Smaller peptides that include immunogenic epitopes, such as those between about 30 and about 50 amino acids in length will often be preferred. The OMP A proteins or peptides may also be combined with other agents and Acinetobacter components, as desired.

By "immunologically effective amount" is meant an amount of an OMP A protein or peptide composition that is capable of generating an immune response in the recipient animal or patient. This includes both the generation of an antibody response (B cell response), and/or the stimulation of a cytotoxic immune response (T cell response). The generation of such an immune response will have utility in both the production of useful bioreagents, e.g., CTLs and, more particularly, reactive antibodies, for use in diagnostic embodiments, and will also have utility in various prophylactic or therapeutic embodiments. Therefore, although these methods for the stimulation of an immune response include vaccination regimens designed to prevent or lessen Acinetobacter infections and associated diseases, and treatment regimens that may lessen the severity or duration of any infection or medical condition, it will be understood that achieving either of these end results is not necessary for practicing these aspects of the invention.

Although the use of the entire OMP A protein is certainly contemplated, the use of shorter antigenic peptides that incorporate OMP A epitopes may provide advantages in certain circumstances. Exemplary advantages include the ease of preparation and purification, the relatively low cost and improved reproducibility of production, and advantageous biodistribution. The preparation of vaccines that contain peptide sequences as active ingredients is generally well understood in the art, as exemplified by U.S. Pat. Nos. 4,608,251; 4,601,903; 4,599,231; 4,599,230; 4,596,792; and 4,578,770, each incorporated herein by reference.

Whether protein- or peptide-based, various methods of achieving adjuvant effects for the vaccines are included. For example, the use of agents such as aluminum hydroxide or phosphate (alum), commonly used as 0.05 to 0.1 percent solution in phosphate buffered saline; and admixtures with synthetic polymers of sugars (Carbopol) used as 0.25 percent solution. Emulsions in physiologically acceptable oil vehicles such as mannide mono-oleate (Aracel A) or emulsion with 20 percent solution of a perfluorocarbon (Fluosol-DA) used as a block substitute may also be employed.

Further means contemplated for generating an immune response in an animal or patient include administering to the animal or human subject a pharmaceutically acceptable composition comprising an immunologically effective amount of an OMP A-encoding nucleic acid composition, or even an immunologically effective amount of an attenuated live organism that includes and expresses an OMP A-encoding nucleic acid composition. The "immunologically effective amounts" are those amounts capable of stimulating B cell and/or T cell responses.

The inventor has further data showing that activation by OmpA can be blocked by a specific inhibitor of Erk kinases (Map kinases). It is therefore likely that OmpA activation of cells occurs through a specific receptor and that OmpA is a "ligand" for a mammalian cell receptor. As such, synthetic peptides or small molecules can be designed to block the inflammatory response in a similar manner to already shown with the present OmpA antibody studies. All such compositions are included within the invention.

The vaccines may be administered in a manner compatible with the dosage formulation, and in such amount as will be immunogenic and therapeutically effective. The quantity to be administered depends on the subject to be treated, including, e.g., the capacity of the individual's immune system to synthesize antibodies, and the degree of protection/treatment desired. Precise amounts of active ingredient required to be administered will be readily determinable by the skilled practitioner. Suitable regimes for initial administration and booster shots are also variable, and are typified by an initial administration followed by subsequent inoculations or other administrations.

The manner of application may be varied widely. Any of the conventional methods for administration of a vaccine are applicable. These will include oral application on a solid physiologically acceptable base or in a physiologically acceptable dispersion, parenterally, by injection and the like. The dosage of the vaccine may also vary with the route of administration.

In many instances, it will be desirable to have multiple administrations of the vaccine, usually not exceeding six vaccinations, more usually not exceeding four vaccinations and preferably one or more, usually at least about three vaccinations. The vaccinations will normally be at from two to twelve week intervals, more usually from three to five week intervals. Periodic boosters at intervals of 1–5 years, usually three years, will be desirable to maintain protective levels of the antibodies. The course of the immunization may be followed by assays for antibodies produced.

A. Pharmaceutical Compositions

The OMP A-based protein, peptide and/or nucleic acid compositions, vaccines, or cocktails thereof will most often be formulated for parenteral administration, e.g., formulated for injection via the intravenous, intramuscular, subcutaneous, transdermal, or other such routes, including peristaltic administration and direct instillation into a tumor or ulcer site.

The preparation of an aqueous composition that contains an OMP A component as an active ingredient will be known to those of skill in the art in light of the present disclosure. Typically, such compositions can be prepared as injectables, either as liquid solutions or suspensions. Solid forms suitable for using to prepare solutions or suspensions upon the addition of a liquid prior to injection can also be prepared. The preparations can also be emulsified.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form should be sterile and fluid to the extent that syringability exists. It should be stable under the conditions of manufacture and storage and should be preserved against the contaminating action of microorganisms, such as bacteria and fungi.

The OMP A compositions can be formulated into a sterile aqueous composition in a neutral or salt form. Solutions as free base or pharmacologically acceptable salts can be prepared in water suitably mixed with a surfactant, such as hydroxypropylcellulose. Pharmaceutically acceptable salts, include the acid addition salts (formed with the free amino groups of the protein), and those that are formed with inorganic acids such as, for example, hydrochloric or phosphoric acids, or such organic acids as acetic, trifluoroacetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Suitable carriers include solvents and dispersion media containing, for example, water, ethanol, polyol (for example, glycerol, propylene glycol, and liquid polyethylene glycol, and the like), suitable mixtures thereof, and vegetable oils. In many cases, it will be preferable to include isotonic agents, for example, sugars or sodium chloride. The proper fluidity can be maintained, for example, by the use of a coating, such as lecithin, by the maintenance of the required particle size in the case of dispersion and/or by the use of surfactants.

Under ordinary conditions of storage and use, all such preparations should contain a preservative to prevent the growth of microorganisms. The prevention of the action of microorganisms can be brought about by various antibacterial and antifungal agents, for example, parabens, chlorobutanol, phenol, sorbic acid, thimerosal, and the like. Prolonged absorption of the injectable compositions can be brought about by the use in the compositions of agents delaying absorption, for example, aluminum monostearate and gelatin.

Prior to or upon formulation, the OMP A component should be extensively dialyzed to remove undesired small molecular weight molecules, and/or lyophilized for more ready formulation into a desired vehicle, where appropriate. Sterile injectable solutions are prepared by incorporating the active agents in the required amount in the appropriate solvent with various of the other ingredients enumerated above, as desired, followed by filtered sterilization. Generally, dispersions are prepared by incorporating the various sterilized active ingredients into a sterile vehicle that contains the basic dispersion medium and the required other ingredients from those enumerated above.

In the case of sterile powders for the preparation of sterile injectable solutions, the preferred methods of preparation are vacuum-drying and freeze-drying techniques that yield a powder of the active ingredient, plus any additional desired ingredient from a previously sterile-filtered solution thereof.

Suitable pharmaceutical compositions in accordance with the invention will generally include an amount of the OMP A component admixed with an acceptable pharmaceutical diluent or excipient, such as a sterile aqueous solution, to give a range of final concentrations, depending on the intended use. The techniques of preparation are generally well known in the art as exemplified by Remington's Pharmaceutical Sciences, 16th Ed. Mack Publishing Company, 1980, incorporated herein by reference. It should be appreciated that endotoxin contamination should be kept minimally at a safe level, for example, less that 0.5 ng/mg protein. Moreover, for human administration, preparations should meet sterility, pyrogenicity, general safety and purity standards as required by FDA Office of Biological Standards.

Upon formulation, an OMP A component solution will be administered in a manner compatible with the dosage formulation and in such amount as is therapeutically effective. The type of injectable solutions described above are generally preferred, but other pharmaceutically acceptable forms are also contemplated, e.g., tablets, pills, capsules or other solids for oral administration, suppositories, pessaries, nasal solutions or sprays, aerosols, inhalants, liposomal forms and the like.

For OMP A-based suppositories, traditional binders and carriers may include, for example, polyalkalene glycols or triglycerides: such suppositories may be formed from mixtures containing the active ingredient in the range of 0.5% to 10%, preferably 1–2%.

Pharmaceutical "slow release" capsules or compositions may also be used. Slow release formulations are generally designed to give a constant drug level over an extended period and may be used to deliver OMP in accordance with the present invention.

B. Therapeutic Kits

This invention also provides therapeutic kits comprising OMP A component(s) for use in the present treatment methods. Such kits will generally contain, in suitable container means, a pharmaceutically acceptable formulation of at least one OMP A component. The kits may also contain other pharmaceutically acceptable formulations for combined therapy. For example, such kits may contain any one or more of a range of Acinetobacter antigens, conventional ulcer therapeutics, or chemotherapeutic or radiotherapeutic drugs or anti-tumor cell antibodies, where cancer treatment is planned.

The kits may have a single container (container means) that contains the OMP A component, with or without any additional components, or they may have distinct containers for each desired agent. Where combined therapeutics are provided, a single solution may be pre-mixed, either in a molar equivalent combination, or with one component in excess of the other. Alternatively, each of the OMP A components and other agents, such as Acinetobacter antigens, ulcer therapeutics, or anti-cancer agents, may be maintained separately within distinct containers prior to administration to a patient.

When the components of the kit are provided in one or more liquid solutions, the liquid solution is preferably an aqueous solution, with a sterile aqueous solution being particularly preferred. However, the components of the kit may be provided as dried powder(s). When reagents or components are provided as a dry powder, the powder can be reconstituted by the addition of a suitable solvent. It is envisioned that the solvent may also be provided in another container.

The containers of the kit will generally include at least one vial, test tube, flask, bottle, syringe or other container means, into which the OMP A component and any other desired agent, may be placed and, preferably, suitably aliquoted. Where separate components are included, the kit will also generally contain a second vial or other container into which these are placed, enabling the administration of separated designed doses. The kits may also comprise a second/third container means for containing a sterile, pharmaceutically acceptable buffer or other diluent.

The kits may also contain a means by which to administer the OMP A component to an animal or patient, e.g., one or more needles or syringes, or other such like apparatus, from which the formulation may be injected into the animal or applied to a diseased area of the body. The kits of the present invention will also typically include a means for containing the vials, or such like, and other component, in close confinement for commercial sale, such as, e.g., injection or blow-molded plastic containers into which the desired vials and other apparatus are placed and retained.

C. DNA Vaccination

In light of developing technology on DNA vaccination, it will be understood that virtually all such vaccination regimens will be appropriate for use with OMP A immunization. In addition to parenteral routes of DNA inoculation, including intramuscular and intravenous injections, mucosal vaccination is also contemplated, as may be achieved by direct application.

The stimulation of specific antibodies and CTL (cytotoxic T lymphocyte) responses by administering to an animal a nucleic molecule is now well known in the art, as evidenced by articles such as Tang et al. (1992); Cox et al. (1993;) Fynan et al. (1993); Ulmer et al. (1993); Wang et al. (1993) and Whitton et al. (1993); each incorporated herein by reference. The use of attenuated organisms, such as vaccinia viruses and salmonella, that express recombinant DNA products is also now established in the art and contemplated for use in the present invention.

The naked DNA technology, often referred to as genetic immunization, is contemplated to be suitable to protect against infectious organisms. Immunization with DNA has been successfully employed to protect animals from challenge with influenza A (Ulmer et al., 1993). The use of the OMP A-encoding nucleic acid compositions of the present invention in such genetic immunization techniques is thus another useful vaccination regimen. The OMP A-encoding nucleic acid segments could be used in virtually any form, including naked DNA and plasmid DNA, and may be administered to the animal in a variety of ways, as described, for example, by Fynan et al. (1993).

In addition to naked DNA technology, or genetic immunization, using recombinant DNA or plasmids, other embodiments of the invention deliver DNA entrapped in liposomes or lipofectamine-DNA complexes. In yet further embodiments, the ability of viruses to enter cells and to integrate into host cell genome is used to transfer OMP A nucleic acids into target cells. Preferred gene therapy vectors of the present invention will generally be viral vectors.

Retroviruses have promise as gene delivery vectors due to their ability to integrate their genes into the host genome, transferring a large amount of foreign genetic material, infecting a broad spectrum of species and cell types and of being packaged in special cell-lines. Other viruses, such as adenovirus, herpes simplex viruses (HSV), cytomegalovirus (CMV), and adeno-associated virus (AAV), such as those described by U.S. Pat. No. 5,139,941, incorporated herein by reference, may also be engineered to serve as vectors for gene transfer.

Adenoviruses do not integrate their genetic material into the host genome and therefore do not require host replication for gene expression, making them ideally suited for rapid, efficient, heterologous gene expression. Adenoviral vectors may be employed with the present invention, and techniques for preparing replication-defective infective viruses are well known in the art.

In certain further embodiments, an HSV gene therapy vector may be used. A factor that makes HSV an attractive vector is the size and organization of the genome. Because HSV is large, incorporation of multiple genes or expression cassettes is less problematic than in other smaller viral systems. In addition, the availability of different viral control sequences with varying performance (temporal, strength, etc.) makes it possible to control expression to a greater extent than in other systems. It also is an advantage that the virus has relatively few spliced messages, further easing genetic manipulations. HSV also is relatively easy to manipulate and can be grown to high titers. Thus, delivery is less of a problem, both in terms of volumes needed to attain sufficient MOI and in a lessened need for repeat dosings.

Of course, in using viral delivery systems, one will desire to purify the virion sufficiently to render it essentially free of undesirable contaminants, such as defective interfering viral particles or endotoxins and other pyrogens such that it will not cause any untoward reactions in the cell, animal or individual receiving the vector construct. A preferred means of purifying the vector involves the use of buoyant density gradients, such as cesium chloride gradient centrifugation.

The following examples are included to demonstrate certain preferred embodiments of the invention. It will be appreciated by those of skill in the art that the compositions and techniques disclosed in the examples that follow represent compositions and techniques discovered by the inventor to function well in the practice of the invention, and thus can be considered to constitute certain preferred modes for its practice. However, those of skill in the art should, in light of the present disclosure, appreciate that many changes can be made in the specific embodiments that are disclosed and still obtain a like or similar result without departing from the spirit and scope of the invention.

EXAMPLE I

An OmpA-like Protein from Acinetobacter Stimulates the Gastrin and IL-8 Promoters A. Materials and Methods 1. Reagents The IL-8 luciferase reporter construct was obtained from H. C. Reinecker (Massachusetts General Hospital, Boston) and contains the first 497 bp of the human IL-8 promoter as described by Mukaido et al. (1989; specifically incorporated herein by reference) in pGL3 basic (Promega).

A mixed stock of Acinetobacter, Pseudomonas and Corynebacterial spp. were used to inoculate blood agar plates consisting of 5% sterile horse blood in Campylobacter -selective agar (CSA) (Difco) supplemented with 5% (vol/vol) sterile horse blood (Rockland). The plates were incubated for 5 days in a humidified microaerophilic chamber to mimic the stomach environment. (BBL Gas System, with CampyPak Plus packs, Fisher). The bacteria recovered from the mice and cultured under these conditions were urease, catalase and oxidase positive.

To document the absence of any *H. pylori* species, the culture was plated onto blood agar plates supplemented with multiple antibiotics (Fungizone 1.5 ml/L, vancomycin 6.67 mg/ml, Polymyxin B sulfate 0.22 mg/ml, Bacitracin 13.33 mg/ml and Nalidixic Acid 2.14 mg/ml). No growth was observed.

Whole cell sonicates were prepared by removing bacterial growth with a cotton swab, suspending in ice cold PBS (10 ml per 150 mm plate) then pelleting the bacteria collected in ml conical tubes at 3000 rpm for 10 min at 4° C. The washed bacterial pellet was resuspended in a final concentration of $10^8$ organisms/ml. Five 15 second bursts at 30% power output were used to disrupt the bacterial wall at 4° C. Heated supernatants (HS) were prepared from the whole cell sonicates (WCS) by incubating the sonicate for 15 min at 80° C. then pelleting denatured protein at 10,000 rpm for 15 min.

50 µg of either WCS or HS was added to each 35 mm well of a 6 well plate. Luciferase activity normalized to protein was analyzed 6 h later after incubating cells with live organisms or 3 h later after incubation with bacterial extracts. Protein concentrations were determined by the method of Bradford (1976). The results were expressed as induction relative to the untreated controls. The proteins in the HS were size fractionated in a 2 ml volume Centricon filter (Millipore) with a membrane size limit of 10 kDa according to the manufacturer's instructions.

2. Bacterial Colonization in Mice

C57BL6 (Charles River) underwent gastric intubation with a catheter 4 times over 4 consecutive days with 100 µl of bacterial suspension containing $10^8$ organisms in PBS. Control animals were treated with a suspension of $10^8$ DH5α *E. coli* organisms. The animals were fasted overnight then sacrificed 2 and 6 months later. The stomach was fixed in 4% paraformaldehyde diluted in. PBS and paraffin embedded. Three micron sections were prepared, deparaffinized and stained with hematoxylin and eosin.

Acinetobacter colonization was verified by reculturing stomach homogenates. Re-intubation of mice with a pure subculture of the Acinetobacter spp. was accomplished as described above after twice daily oral administration of streptomycin (0.2 ml per intubation of 5 mg/ml stock solution) over 5 days. Serum gastrin levels were determined by radioimmunoassay.

3. Cell Culture

AGS cells (derived from a human gastric adenocarcinoma (Barranco et al., 1983) were obtained from American Type Culture Collection (ATCC) and cultured in Dulbecco's Modified Eagle's Medium (Gibco-BRL) containing 10% fetal calf serum, 100 µg/ml penicillin, and 100 µg/ml streptomycin in a humidified atmosphere of 5% $CO_2$ and 95% air in 35 mm 6 well culture dishes at 37° C.

The cells were stably transfected with the 240 gastrin luciferase reporter construct (240 GasLuc), selected in G418 (Gibco-BRL) and pooled as described by Ford et al. (1997; specifically incorporated herein by reference). The 240 GasLuc construct contains 240 bp of the human gastrin promoter and the first exon ligated upstream of the luciferase reporter in pGL2 basic (Promega). Calcium phosphate coprecipitation (5 Prime-3 Prime) was used to perform stable transfections into AGS cells. The cells were incubated 48 h in F-12 Nutrient Mixture (Ham's) containing 100 µg/ml penicillin and 100 µg/ml streptomycin (Gibco-BRL) without serum prior to treatment with 10 nM EGF, 20 ng/ml IL1β or 50 µg of bacterial extracts.

4. Protease Digestion

*Staphylococcal aureus* V8 and trypsin proteases were purchased from Sigma. 300 µg of the HS were incubated at 37° C. with 7500 units of each protease. A second aliquot of the proteases was added after 3 h and the incubation allowed to proceed overnight. Protease activity was inactivated by heating to 80° C. for 15 min. and pelleting denatured protein. Digestion of the proteins in the HS was confirmed by SDS-PAGE and Coomassie blue staining. 50 µg of the digest was added to the luciferase expressing stable transformants to determine whether the activity in the HS was protease sensitive. There was no morphologic change in the cells after incubating with the protein digest. Protein concentrations were determined by the method of Bradford (Bradford, 1976).

5. Protein Elution

Bacterial proteins from the HS were resolved on a 4–12% gradient gel (Novex) and visualized by Sypro Orange (Molecular Probes). The 38, 130 and 15 kDa proteins were excised, minced then electro-eluted overnight at 10 mA per sample in a Bio-Rad Electro-Eluter (Model 422) in the presence of 25 mM Tris, 192 mM glycine and 0.1%SDS. The SDS was removed by continuing the elution for an additional hour in the absence SDS. 50 µl of the eluted protein was added per well of a 6 well plate (35 mm).

6. Peptide Analysis

SDS-polyacrylamide gel electrophoresis was carried out on a 4–12% gradient gel (Novex) and stained using Coomassie blue dye. Edman degradation N-terminal sequences analysis was carried out after transferring resolved proteins to polyvinylidene fluoride paper. Thirty N-terminal amino acids were sequenced from the 38 kDa protein isolated from the heated supernatant and bacterial wash fraction. In addition, a cyanogen bromide digest of the 38 kDa protein was resolved on a 10% SDS polyacrylamide gel, transferred to PVDF for amino acid sequencing by Edman degradation.

7. Genomic Library Screen

The forward primer for cloning was a degenerate oligonucleotide sequence based upon a sequence from the N-terminal amino acid sequence from the full-length 38 kDa protein. The reverse primer was a degenerate oligonucleotide sequence based upon an amino acid sequence from the 9 kDa peptide. The primers produced a 600 bp fragment from genomic DNA. This fragment was labeled using the Rediprime II kit (Stratagene) and used to screen a genomic bacterial library.

The library in lambda ZAP II (Stratagene) was prepared from genomic DNA extracted from the bacterial culture mixture using a genomic DNA extraction kit (Qiagen). $10^7$ plaques of the unamplified library were screened. The Bluescript plasmid containing genomic inserts were excised with helper phage and sequenced. Of the six positive clones identified containing 0.4 to 1.6 kb inserts, all six were partially sequenced and confirmed that they contained the same overlapping sequence. Two of the overlapping clones containing the most distal 5' and 3' sequences were completely sequenced to produce a 1.7 kb genomic contig for the ompA locus.

8. Antibody Production and Immunoblot

Peptide sequences chosen for raising antibodies included an N-terminal and C-terminal sequence. Antibodies to the N-terminal sequence were generated to follow the newly synthesized protein. The peptide sequence used was GVTVTPLMLGYTFQDTQHNN (amino acids 22–41 of SEQ ID NO:2), which was conjugated to Map (multiple antigenic protein). There is strong homology of the chosen peptide to the N-terminal of the Moraxella protein, so this is less preferred for use in generating specific antibodies.

Antibodies can also be raised to whole recombinant protein, e.g., following expression in bacteria. The remainder of the OMP A protein is quite hydrophobic, and it is not difficult to identify further suitable amino acid sequences for antibody generation. Additional OMP A peptides for use as antigens based on their "antigenicity" and "surface probability" are: DTQHNNNGND (amino acids 36–45 of SEQ ID NO:2); TGNYDSKVKP (amino acids 111–120 of SEQ ID NO:2); YKYEFEGVPRGTRGNEEEG (amino acids 129–147 of SEQ ID NO:2); TNKSNIKDQYKPEIAK (amino acids 236–251 of SEQ ID NO:2); and DQPI-ADNNTKEGR (amino acids 313–325 of SEQ ID NO:2). Based on sequence homology programs, the peptides have been chosen not to cross-react with the Moraxella protein.

The C-terminal peptide chosen was GSRTVLAEQPVAQ (amino acids 337–349 of SEQ ID NO:2). The peptide (250 micromoles) was conjugated to keyhole limpet hemocyanin (KLH) via a cysteine residue (KLH-Cys-GSRTVLAEQPVAQ). The OMP sequence was first conjugated to cysteine to give Cys-GSRTVLAEQPVAQ, permitting conjugation of KLH to the N-terminal of the sequence, leaving the C-terminal free. Rabbits were injected monthly with 250–500 mg of the peptide (Rockland) and analyzed by Western blot using the HS as the antigen. An immunoglobulin fraction was prepared from both the immune and pre-immune sera using Protein A agarose (Santa Cruz) prior to use.

To detect the OmpA on immunoblots, protein transferred to polyvinylidene fluoride membrane was blocked for 1 h with 0.5 × Uni-block (Analytical Genetic Testing Center, Inc.) then incubated with a 1:10,000 dilution of the immunoglobulin fraction raised against the C-terminal peptide for 1 h at 25° C. A 1:1000 dilution of the secondary antibody was used and the complexes were detected by enhanced chemiluminescence (SuperSignal, Pierce).

9. Recombinant Protein

Primers that have adapters on them may be used in connection with expression vectors. They permit PCR amplification of the entire sequence. Examples of such PCR primers include forward, 5' cgc gga tcc ATG GCC TAT TGC GGG CTT GAG CTT GAA (SEQ ID NO:3; the ggatcc adds a BamH1 site to the OMP sequence); forward, cgc gga tcc GGC GTA ACT GTT ACT CCG TTG ATG TTG GGG (SEQ ID NO:4; the ggatcc adds a BamH1 site to the OMP sequence); and reverse, 5' ctc gaa ttc tTG AGC AAC TGG TTG TTC AGC TAA AAC (SEQ ID NO:5; the gaattc adds an EcoR1 site to the OMP sequence).

To produce recombinant OmpA protein, the cDNA was amplified from the Bluescript plasmid using one of two forward primers (GGCGTAACTGTTACTCCGTTGATG, minus putative signal peptide, nt 64–87 of SEQ ID NO:1; or ATG GCCTATTGCGGGCTTGAGCTT, full length, nt 529–552 of SEQ ID NO:6) and a reverse primer (TTGAGCAACTGGTTGTTCAGCTAAAACAG, nt from SEQ ID NO:1). The amplimer was then inserted into the EcoR1 site of the TA Cloning vector (Invitrogen) and sequenced to determine the orientation. The EcoR1 fragment was excised from the TA cloning vector and directionally subcloned into the EcoR1 site of the pET vector (Novagen). The orientation was verified by restriction analysis and sequencing.

The resulting expression vector was used to transform BL21 (DE) cells and produce recombinant protein. The recombinant protein was induced at 37° C. with 1 mM IPTG for 3–4 h then purified from the bacterial pellet (inclusion bodies) according to the method described by Yang et al. (1997; specifically incorporated herein by reference). Briefly, the bacterial pellet obtained after sonication, was suspended in 50 mM Tris-HCl, pH 8.0 in 0.5% Triton X-100 and 10 mM EGTA. It was then centrifuged at 20,000g for 30 min at 4° C. The pellet was washed in 50 mM Tris-HCl, pH 8.0 containing 0.1% SDS and re-suspended in 50 mM Tris-HCl, pH 8.0 in 0.5% Triton X-100 and 10 mM EGTA. To this suspension, a final concentration of 6 M urea was added, heated to 60° C. for 30 min then dialyzed at 4° C. against 50 mM Tris-HCl, pH 8.0 overnight. Due to low solubility, this suspension was resolved on an SDS polyacrylamide gel as described for the eluted protein above prior to adding to the AGS cell cultures.

B. Results

1. Increase in Serum Gastrin by Gastric Flora

Mice were infected with the mixture of opportunistic pathogens then sacrificed after 2 months. The stomachs were examined by immunohistochemistry and revealed mucosal and submucosal infiltrates in the corpus and antrum. Serum gastrin levels were elevated in infected versus control mice by ~4-fold (14.2 fmol/ml±4.0 SEM; n=3 vs 3.2 fmol/ml +1.1 SEM; n=3; respectively.

2. Regulation of the Gastrin Promoter by Bacterial Co-Culture

To examine whether bacterial contact directly stimulates gastrin gene expression, increasing concentrations of the bacterial mixture used to infect the mice were co-cultured with stable transformants of AGS cells that express the human gastrin reporter construct. The effect of the organisms on IL-8 promoter activity was also examined. The results demonstrate a dose-dependent increase in both gastrin and IL-8 promoter activity with increasing concentrations of bacteria (FIG. 1). This shows that live organisms were capable of stimulating gastrin as well as IL-8 promoter activity that correlated with their ability to increase serum gastrin levels in infected mice.

3. Identifying a Protein Fraction that Stimulates Promoter Activity

Figure 2:
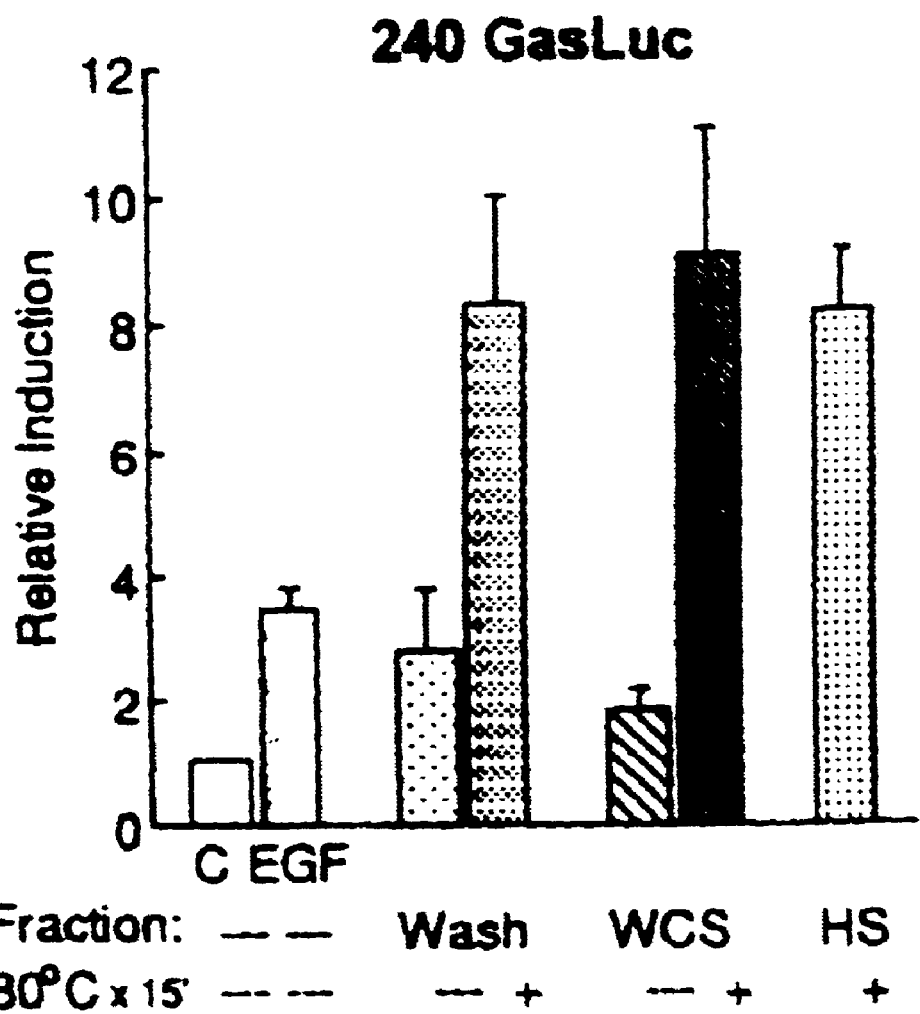
FIG. 2. The bacterial fraction stimulating the gastrin promoter is heat-stable. The PBS wash, whole cell sonicates (WCS) and supernatant from the WCS were heated to 80° C. for 15 min. The heated supernatant fraction (HS) represents the activity after pelleting insoluble protein (Pellet) at 10,000 rpm for 15 min. 50 µg of the various fractions were used to stimulate stable transformants that express the human gastrin reporter construct. The relative induction±S.E. for at least four studies is shown.

To isolate a bacterial subfraction containing the promoter-stimulating activity, the proteins recovered from the bacterial wash as well as the whole cell sonicate (WCS) and supernatant from the WCS were heated to 80° C. for 15 min. then separated into soluble and insoluble fractions. Surprisingly, the substance stimulating an increase in promoter activity partitioned with the heat-soluble fraction (FIG. 2). This result raised several possibilities—that the activating substance was not protein or that heating removed heat-labile inhibitory substances. A third consideration was that heating induced a conformational change in the protein such that it was more active.

To address the first two possibilities, the various fractions, including the heat stable supernatant, were resolved on a 4–12% gradient denaturing gel, stained with Coomassie blue dye and compared to molecular weight markers. A striking finding was the similarity between the heat stable bacterial wash and the heat stable fraction isolated from the whole cell sonicate. The most abundant protein in the heat stable supernatant prepared from the whole cell sonicate was a 38 kDa protein that also appeared in the heated wash. Much of the protein was heat labile and was rendered insoluble. Thus, the higher specific activity may be related to the removal of an inhibitor.

Figure 3:
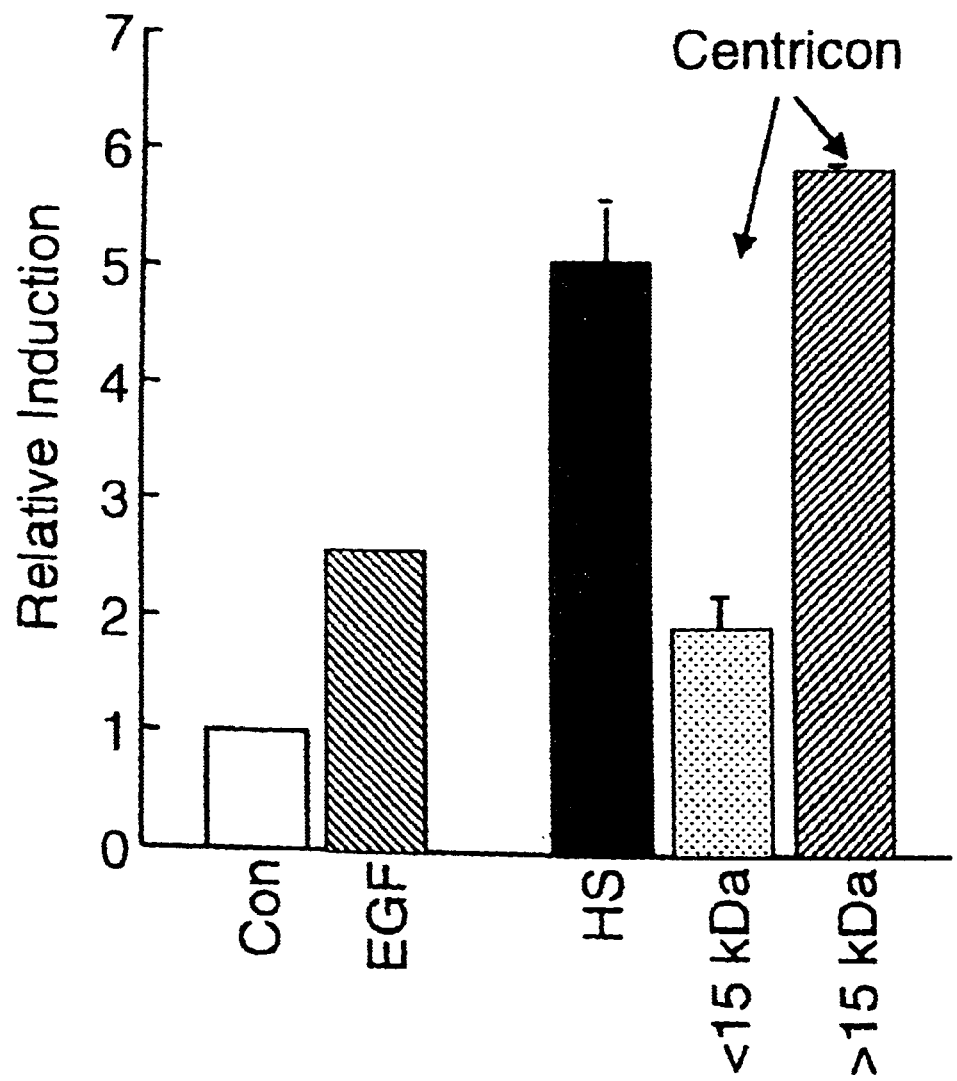
FIG. 3. The bacterial activity segregates with protein >15 kDa. Activity of the gastrin promoter after stimulating the stable transformants with 10 nM EGF or with 50 μg of the heated supernatant fraction (HS) or the >15 kDa or <15 kDa protein fractions from the Centricon filter. Shown is the mean of two studies.

To examine whether the activating material was of protein origin versus a small organic molecule or peptide, size fractionation was performed using Centricon spin columns set to exclude weights of approximately 10 to 15,000 daltons. The Centricon fractions greater or less than 15 kDa were resolved on a 4–12% SDS polyacrylamide gradient gel. The activity of the gastrin promoter was determined after stimulating the stable transformants with 10 nM EGF or with 50 µg of the heated supernatant fraction or the >15 kDa or <15 kDa protein fractions from the Centricon filter (FIG. 3). The results demonstrate that most of the activity segregated with the higher molecular weight proteins >15 kDa (FIG. 3), indicating that the activating factor was not a small molecule. A minimum amount of activity segregated with the small molecular weight material, suggesting that this may represent either peptides or proteolytic fragments of the higher molecular weight proteins.

Figure 4:
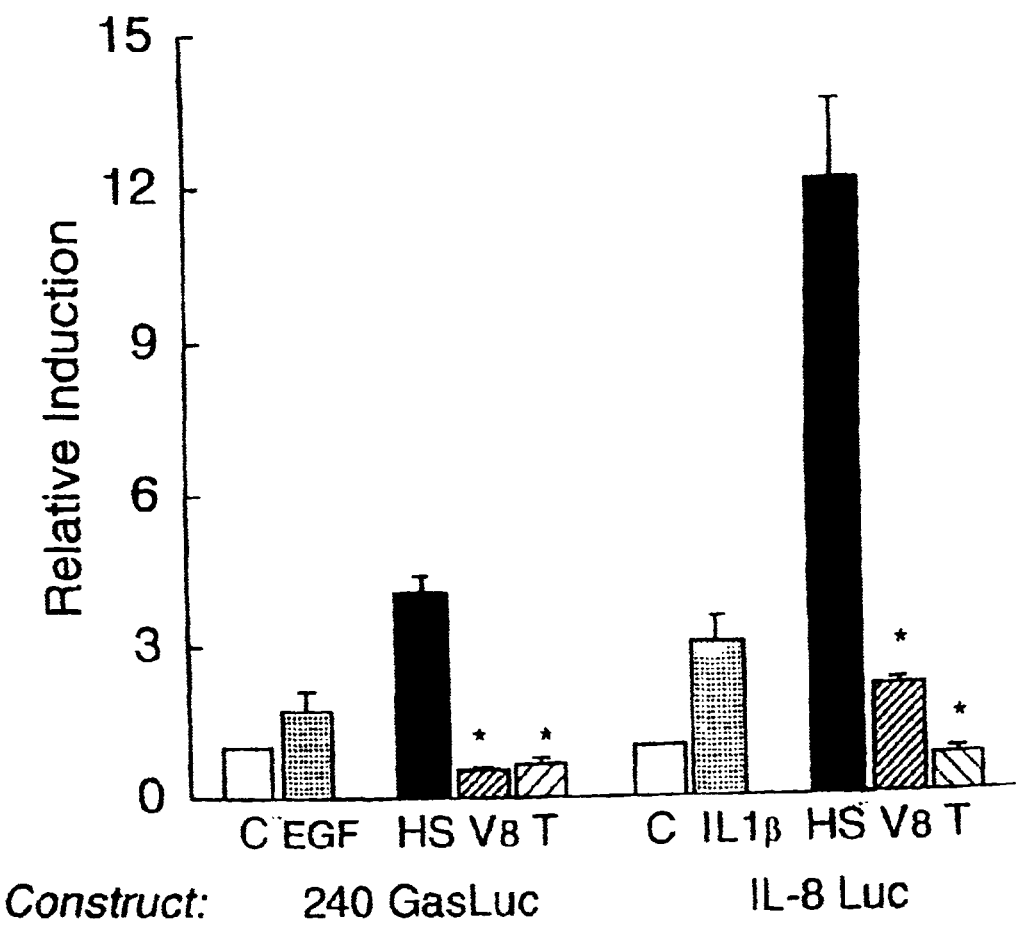
FIG. 4. The activity in the heated supernatant (HS) is protease sensitive. The heated supernatant (HS) was digested with either V8 protease (V8) or trypsin (T) overnight. 50 μg of the HS before and after protease digestion was incubated with the stable transformants expressing the human gastrin (240 GasLuc) or IL-8 (IL-8 Luc) promoters for 3 h prior to assaying for luciferase activity and expressed as relative induction. Treatment of the gastrin and IL-8 promoters with 10 nM EGF or 4 ng/ml of IL-1β respectively is shown. The mean±S.E. is shown for 3 independent studies. *$P<0.05$.

To demonstrate directly that the factor was a protein, the heated supernatant was treated with *Staphylococcal aureus* V8 or trypsin proteases (FIG. 4). Indeed, both proteases abolished the expected induction of both promoters by the heat stable fraction (HS). Therefore, it can be concluded that the gram negative organisms produce soluble, heat stable proteins capable of stimulating gene expression.

4. Transcriptional Activity Attributed to 38 kDa Protein

Figure 5:
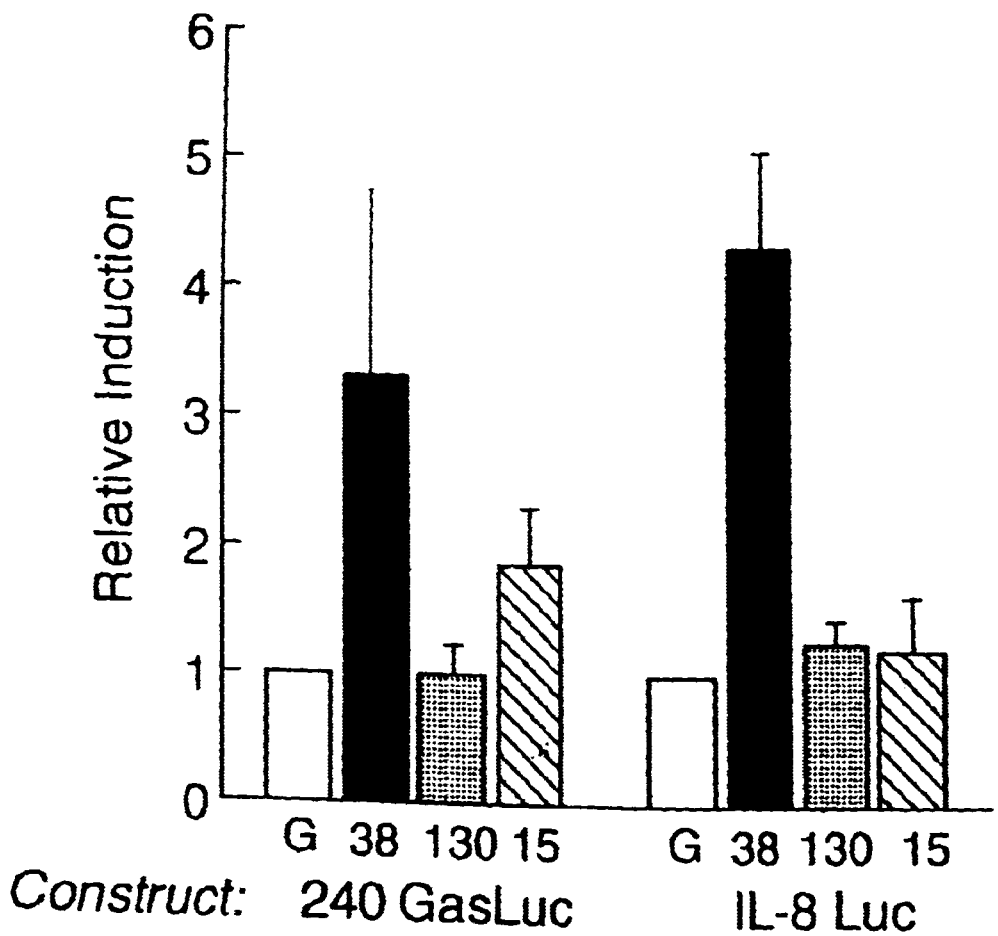
FIG. 5. Eluted 38 kDa protein isolated from the HS stimulates the gastrin promoter and IL-8 promoters. Protein bands eluted from Coomassie blue stained SDS-PAGE gels were used reporter gene assays. The figure shows the relative induction of the gastrin (240 GasLuc) and IL-8 (IL-8 Luc) promoter constructs stably expressed in AGS cells after treatment with the eluted 38 (solid bars), 130 (stippled bars) and 15 (hatched bars) kDa proteins. Eluted gel (G, open bars) without protein was used as the control for the eluted protein bands. Shown is representative of 3 studies performed in triplicate.

To determine whether the activity resided with one or more of the abundant heat stable proteins, three protein bands including the abundant 38 kDa protein were eluted from the SDS gel. Equivalent amounts of eluted protein verified by SDS-PAGE were tested on the stable transformants expressing the gastrin and IL-8 promoters. The results shown in FIG. 5 demonstrate that much of the induction was mediated by the 38 kDa heat-stable protein in contrast to the 130 and 15 kDa protein bands.

5. Peptide Sequencing

Since a significant amount of the promoter activity was attributed to the 38 kDa protein, peptide sequencing was performed on the eluted band. N-terminal sequencing of the first 30 amino acids revealed the sequence GVTVTPL MLGYTFODTOHNNNGNDGELTSS (amino acids 22–51 from SEQ ID NO:2). The N-terminal sequence showed 80% similarity to outer membrane protein CD from a respiratory pathogen *Moraxella catarrhalis*.

Cyanogen bromide cleavage produced several internal peptides that were subsequently sequenced. Sequencing of a 9 kDa fragment revealed the sequence ELR VFFDTNKSNIKDQYKPEIAKVAEKLVE (amino acids 229–258 from SEQ ID NO:2). The 9 kDa fragment was 80% identical to a sequence within the C-terminus of the same Moraxella protein. Thus, it was concluded that the bacterial factor is also an outer membrane protein.

6. Cloning of an ompA-like gene.

Degenerate PCR™ primers were designed from the two N- and C-terminal peptides. The forward primer was based upon the underlined sequence from the foregoing N-terminal sequence of the full-length 38 kDa protein. The reverse primer was based upon the underlined sequence from the 9 kDa peptide. The primers produced a 600 bp amplimer with genomic DNA isolated from the bacterial culture. The resulting amplimer was subcloned, sequenced and translated to confirm overlap with the N-terminal and C-terminal peptides and one additional 21 kDa internal CNBr peptide fragment.

This 600 bp fragment was then used to screen a genomic library created from genomic DNA. Two of the six overlapping clones were sequenced completely creating a 1.7 kb locus (SEQ ID NO:6) containing the 1.1 kb coding sequence (SEQ ID NO:1). The GenBank Accession number for SEQ ID NO:1, which encodes the protein of SEQ ID NO:2, is #AF132598; NCBI ref #555286.

Translation of the open reading frame based upon the most N-terminal peptide revealed two TAA stop codons 78 bp upstream of a putative ATG start codon. Another in-frame ATG was identified 57 bp further upstream. However, this second ATG was not preceded by a Shine-Dalgarno sequence. Thus, the predicted ATG was preceded by a perfect Shine-Dalgarno sequence (TGGAGGAT) 6 bp upstream of the translational start codon (Freifelder, 1983).

The additional 21 amino acid residues upstream of the original peptide beginning with GVTV (i.e., the peptide from N-terminal sequencing) was 45% identical to the *E. coli* OmpA signal sequence and the leader sequence of other secreted bacterial proteins (Pratap and Dikshit, 1998). Amino acids 22–262 were similar to transmembrane domains of OmpA (Lawrence et al., 1991).

Thus, overall the translated protein contained 349 amino acids, corresponding to a molecular weight of 38 kDa (35 kDa without the N-terminal leader sequence) and a pI of 4.76. There were no cysteine residues present within the entire open reading frame. These features are consistent with the abundant heat-modifiable class of outer membrane proteins called OmpA found in most gram negative bacteria. For example, there is homology between the Moraxella outer membrane CD OmpA-like protein and the newly cloned OmpA-like protein.

7. Recombinant OmpA-like protein stimulates gastrin and IL-8 promoter activity

Figure 6:
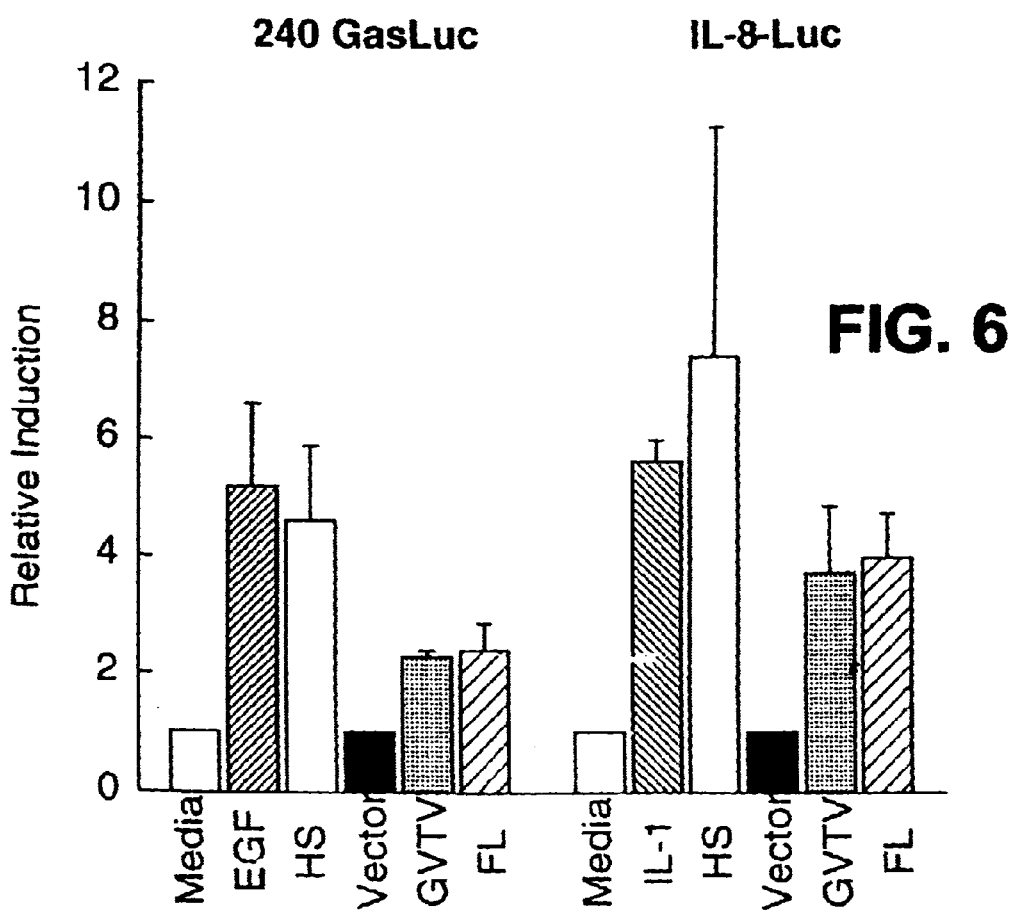
FIG. 6. Recombinant OmpA-like protein stimulates gastrin and IL-8 promoters. Heated supernatant (HS) or two forms (minus signal sequence- GVTV; the full-length protein- FL) of the recombinant OmpA-like protein eluted from the SDS-PAGE gel were incubated with AGS cells stably transfected with the 240 GasLuc or IL-8 Luc reporter constructs. Vector indicates bacterial extract prepared as for the recombinant protein except that the bacteria were transformed with the empty pET vector. Media indicates the AGS culture medium described in the Methods section. The results are the means and range of two independent studies performed in duplicate and plotted as relative induction.

To demonstrate that the recombinant OmpA-like protein stimulated gastrin and IL-8 gene expression, the recombinant protein was prepared from *E. coli* overexpressing transformants and tested on the stably transfected AGS cells. The results demonstrate that the recombinant OmpA-like protein stimulated the gastrin and IL-8 promoters (FIG. 6). The difference between the activity of the HS versus the recombinant protein was due to the lower concentration of protein eluted from the gel.

Figure 7:
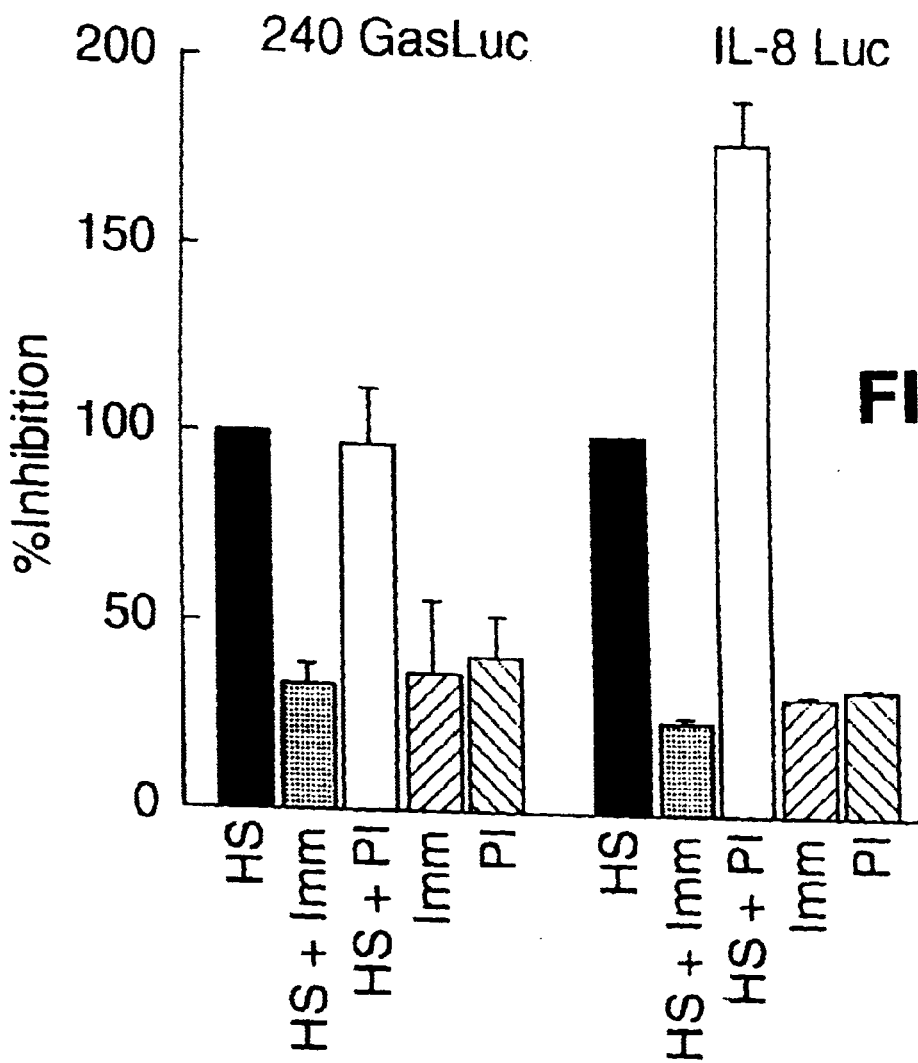
FIG. 7. Neutralization of HS activity with OmpA-like protein antisera. Heated supernatant (HS) alone (20 μg) or in the presence of a 2 μg of antibody raised against the OmpA-like protein (HS+Imm) was incubated with the HS for 4 h prior to precipitating the complexes with Protein A/G. The resulting supernatant was then added to the stable AGS transformants. The same concentration of IgG prepared from the pre-immune serum was used as a negative control (HS+PI). In addition, the immune (Imm) or pre-immune (PI) IgG fractions alone were added to the stable transformants in the absence of the heated supernatant. The results are the means and range of two independent studies performed in duplicate and plotted as % inhibition relative to the HS.

To demonstrate that the OmpA-like protein was the major protein responsible for the activity in the HS, antibody neutralization studies were performed. Antibody raised against the C-terminus of the OmpA-like protein specifically blocked the activation of both the gastrin and IL-8 promoters mediated by the HS; whereas, the pre-immune antibodies did not inhibit activity in the HS (FIG. 7).

8. The OmpA-like protein is expressed only in Acinetobacter species

Since the original bacterial suspension contained at least two other bacterial spp., the mixture was subcultured and typed. Typing of the bacterial species was performed using 16S ribosome primers and comparing the sequences to database entries (Lane et al., 1985). Further characterization was performed using morphology, culture characteristics and enzymatic analysis.

Antibody raised to the cloned OmpA-like protein was used on an immunoblot to identify the bacterial strain expressing the cloned factor. HS from subcultures of Acinetobacter, Pseudomonas and a Corynebacteria spp. were resolved on a 4–12% SDS polyacrylamide gel, transferred to PVDF membrane and probed with a 1:2000 dilution of the OmpA-like antibody. Enhanced chemiluminescence was used to detect the antigen-antibody complexes.

The results demonstrate that the Acinetobacter spp. was the only bacterial strain isolated that expressed the cloned OmpA-like protein. To verify that this species was present in the inoculated mice, a Western blot was performed on the bacteria cultured from the mice. Heated supernatants (HS) were prepared from subcultures of bacteria isolated from two different mice infected with the gram negative organisms 6 month previously. The Coomassie blue stained gel was compared with the immunoblot prepared from the same samples and resolved in parallel. Antibody to the OmpA-like protein was used at a 1:10,000 dilution. The results demonstrate that the same OmpA-like protein cloned was expressed in a subculture of Acinetobacter from infected mouse stomachs. The antibody did not cross react with HS from a Pseudomonas spp.

9. Acinetobacter species causes gastritis

To show that Acinetobacter alone causes gastritis, mice were treated orally for 5 days with streptomycin to sterilize the mouse stomach mouse prior to instilling $10^8$ Acinetobacter organisms. Stomachs from sham-incubated mice were compared to stomachs from mice incubated with $10^8$ Acinetobacter organisms for 2 months. Sections from paraffin-embedded stomach were stained with hemotoxylin and eosin. Results showed the presence of a mucosal mononuclear infiltrate in the mouse corpus not present in the sham-incubated mouse. The infiltrate disrupted the normal architecture of the chief and parietal cells. Thus, Acinetobacter spp. are capable of causing gastritis.

C. Discussion

The inventor hypothesized that one of the events to occur during bacterial colonization of the stomach is the production of virulence factors. The present studies show that the OmpA-like protein from an Acinetobacter spp. stimulates the gastrin and IL-8 promoters, and therefore would be capable of stimulating the production of this hormone and cytokine under conditions that would favor its colonization in the stomach. This result has relevance to atrophic gastritis during which the pH of the stomach rises due to atrophy of the parietal cell population favoring colonization by aerobic and anaerobic flora (Houben and Stockbrugger, 1995). Atrophic gastritis is a late feature of chronic *Helicobacter pylori* infection, but also occurs in pernicious anemia, malnutrition and with advancing age. More importantly, the loss of stomach acid is a risk factor for gastric cancer presumably due to an increase in N-nitroso compounds produced by colonizing bacterial flora (Bartsch et al., 1992).

The antral G cell response to bacterial infection of the gastric mucosa has been most intensively studied during *H. pylori* infection. A major consequence of *H. pylori* colonization is the increase in antral G cells and serum gastrin levels (Graham et al., 1993; Sumii et al., 1994). The studies reported here clearly demonstrate that bacterial species other than *H. pylori* can colonize the stomach and cause inflammation.

Colonization by *H. pylori* does not occur efficiently in the hypochlorhydric stomach due to competition by other bacterial species (Houben and Stockbrugger, 1995). Thus, the ability of *H. pylori* to successfully compete with other bacteria for this rather unique niche is primarily due to its ability to survive in the low pH environment of the stomach, e.g., pH<3. Chronic *H. pylori* infection eventually results in atrophic gastritis resulting in achlorhydria or severe hypochlorhydria. The bacterial overgrowth that follows is usually comprised of aerobic and anerobic flora. Moreover, where mucosal transformation has occurred, *H. pylori* is absent (McCloy et al., 1995; Safatle-Ribeiro et al., 1999; Zhang et al., 1999). Thus, while *H. pylori* infection may initiate the development of atrophic gastritis, it may not mediate the final transforming event. Moreover, it may not be the only bacterial species initiating these events.

The use of the gastrin reporter construct to identify specific virulence factors was based upon the connection between gastrin and the pathogenesis of ulcers and cancer triggered by *H. pylori* infection (Blaser and Parsonnet, 1994). Sustained levels of this hormone are associated with duodenal ulcers (Walsh and Grossman, 1975) as well as neoplastic transformation (Conteas et al., 1988; Finley et al., 1993; Singh et al., 1996). Patients with chronic bacterial infection of the stomach exhibit increases in serum gastrin and G cell populations concomitant with a decrease in D cells (Grahma et al., 1993; Summi et al., 1994).

In the case of the G cell, several regulatory mechanisms may be operating. First, bacterial proteins may have a direct effect on the G cell. Second, there may be a loss of negative regulation due to a direct effect on the D cell. Third, parietal cell atrophy and subsequent achlorhydria may develop after longstanding *H. pylori* infection resulting in elevated serum gastrin through the normal feedback regulatory mechanisms. Since atrophic gastritis is accompanied by a decrease in *H. pylori* colonization (Farinati et al., 1993; Kuipers, 1999), the present inventor contemplated that other organisms colonizing the hypochlorhydric stomach would be capable of stimulating gastrin. Gastrin activation by these organisms would provide a mechanism by which growth factors may be produced in the pre-neoplastic stomach.

To address the first possibility, the inventor determined whether bacterial colonization activates gastrin promoter activity. This study shows that infection by bacterial flora that includes Acinetobacter strains raises serum gastrin levels coincident with inflammation of the mucosa. Indeed, co-culturing with the organisms stimulated both the gastrin and IL-8 promoters in a dose-dependent manner. The production and secretion of IL-8 or other CxC cytokines is an important mechanism to recruit inflammatory mediators to the site of infection (Crabtree, 1998). Therefore, the ability of Acinetobacter to stimulate IL-8 gene expression was evaluated. It was found that stimulation of both IL-8 and gastrin gene expression by Acinetobacter is due to a member of the OmpA protein family. Antibody raised against the Acinetobacter OmpA blocked IL-8 and gastrin promoter activation.

The OmpA-like protein has a low isoelectric point and no cysteines, suggesting that it may be acid as well as heat-stable. This is logical for a protein that is exposed to a low stomach pH. Residues 1–21 are hydrophobic and contain a signal peptide cleavage site (AlaXAla) (Pratap and Dikshit, 1998). The putative leader sequence is 38% identical (76% similar) to the signal peptide for *E. coli* OmpA, which predicts protein translocation, export and cleavage by signal peptidase I (Pratap and Dikshit, 1998). The putative cleavage site for the Acinetobacter spp.-OmpA follows the −3,−1 rule for signal peptides (Duffaud and Inouye, 1988). Thus, the Acinetobacter spp.-OmpA leader sequence is consistent with the protein being present in the outer membrane or periplasm.

Although unique, the protein is generally related to the OmpA-related "heat-modifiable" proteins from Moraxella and Pseudomonas, as well as the OmpA homologs from Salmonella, Shigella and Klebsiella spp. The novel Acinetobacter spp. protein was most homologous to outer membrane protein CD precursor from Moraxella (45% identical; 60% positive over 341 amino acids). It also has ~25% identity and 40% similarity within the C-terminal domain (268–333) to OmpA from *E. coli*, Serratia Salmonella, Shigella, and Klebsiella bacterial species (Hsiao et al, 1995; Kennell et al., 1992; Komatsuzawa et al., 1999; Murphy et al., 1993; Ohnishi et al., 1998; Wexler et al., 1992). Apparently, OmpA proteins usually represent the major outer membrane protein and all gram-negative bacteria have some functional equivalent of OmpA (Beher et al., 1980). The Acinetobacter spp. OmpA protein was 30% identical (47% similar) over 321 amino acids to outer membrane protein porin F (Opfr) from Pseudomonas, which is also a member of the OmpA protein family. Thus, Acinetobacter spp. OmpA is also related to the Pseudomonas porin proteins.

OmpA-related proteins including the Pseudomonas porin F protein (OprF) appear to play a variety of roles depending on the bacterial species. In Pseudomonas, these proteins form pores in mammalian cells that permit the penetration of solutes, support survival in low osmotic conditions, maintain cell shape and participate in antimicrobial resistance (Rawling et al., 1998). OmpA from Shigella, Salmonella, Serratia, *E. coli* and Klebsiella is the prevalent outer membrane protein and is highly immunogenic. It is also a receptor for bacterial phages, mediates F'-pili-dependent conjugation and maintains cell shape (Behrmann et al., 1998; Ghiara et al., 1997; Nguyen et al., 1998; Ortiz et al., 1989; Puohiniemi et al., 1990).

Acinetobacter spp. OmpA is quite heat stable and this property may be related to the "heat modifiable" characteristic of most OmpA proteins including the *Moraxella catarrhalis* CD (Hsiao et al., 1995; Murphy et al., 1999). This property is also a characteristic of *E. coli* OmpA, OmpA from enteropathogens and *H. pylori* porin proteins (Doig and Trust, 1994; Exner et al., 1995; Kennell et al., 1992; Komatsuzawa et al., 1999; Ohnishi et al., 1998; Wexler et al., 1992). "Heat modifiable" proteins migrate in a heterogeneous pattern on SDS gels after heating due to a conformational change in the protein (Beher et al., 1980).

In summary, this is the first report documenting regulation of the human gastrin promoter by a bacterial protein, indicating that bacterial proteins alone, exclusive of inflammation, may be sufficient to mediate elevated serum gastrin levels. This is also the first report of an effect of an OmpA-like protein on mammalian gene expression. IL-8 promoter activity was also activated, consistent with prior reports showing general activation of IL-8 production when epithelial cells are co-cultured with a variety of bacterial strains. The results also show that opportunistic pathogens regulate both gastrin and IL-8 production, at least in part, by producing OmpA-like proteins. It is clear that the 38 kDa OmpA is the major protein within the heat-stable fraction of Acinetobacter spp. that is capable of activating these two promoters.

EXAMPLE II

Atrophic Gastritis and Hypergastrinemia Due to Acinetobacter spp. in Mice

A. Materials and Methods

1. Bacterial Strains and Culture Conditions

A stock of Acinetobacter spp. (cultured and purified from the mouse stomach) was used to inoculate LB plates. The plates were incubated overnight at 37° C. The bacteria were harvested and used for oral intubations of mice. A stock of

*H. pylori* (SS1 strain, obtained from K. A. Eaton, Ohio State University) was inoculated on 5% sterile horse blood in Campylobacter selective agar (CSA) (Difco) supplemented with trimethoprin (mg/ml), vancomycin (10 mg/ml) and nystatin (10 mg/ml) (Lee et al., 1998). Plates were incubated for two days in a humidified microaerophilic chamber (BBL Gas System, with CampyPak Plus packs, Fisher). *H. pylori* was harvested used to inoculate mouse stomachs by oral intubations.

Twelve week old C57B1/6 mice were anaesthetized by ether. Mice were pretreated with streptomycin (5 mg/ml) diluted in brain heart infusion (BHI) for three consecutive days. Mice were then orally inoculated with a catheter three times over a period of three days with $10^8$ organisms per 200 µl of either Acinetobacter or *H. pylori* suspension in BHI. Control animals were treated with 200 µl of BHI alone. Mice were sacrificed at 2, 3 and 4 months after oral inoculation.

Colonization of mouse stomachs by Acinetobacter was verified by streaking gastric biopsies onto LB plates followed by incubation at 37° C. for 24 h. Bacteria from these plates were then harvested, heated supernatant prepared and a Western blot was performed using antiserum specific for the Acinetobacter Omp-A protein (Example I; Ofori-Darko et al., 2000). A 1:10,000 dilution of the Omp-A immunoglobulin fraction was used. To verify colonization after *H. pylori* inoculation, gastric biopsies were collected from the stomach, streaked onto blood agar plates, and incubated under microaerophilic conditions at 37° C. for 5–7 days. Bacteria were then tested for urease, oxidase and catalase activity. In addition, sections from the corpus and antrum of both Acinetobacter and *H. pylori* inoculated mice were fixed in 2% paraformaldehyde, paraffin-embedded and a Warthin-Starry stain performed to verify the presence of organisms in the gastric mucosa.

2. Cell Preparation and Flow Cytometry

Lymphocytes and epithelial cells were isolated from the gastric mucosa according to Davies & Parrott, 1981 and Taguchi et al., 1990, each specifically incorporated herein by reference. Briefly, mucosa was dissected into 2 mm size pieces and incubated in 20 ml of Hank's balanced salt solution containing 5% BSA, 1 mM DTT and 1 mM EDTA for 1 hour with vigorous shaking at 37° C. The cell suspension was passed through a filter (50 µm Filcon filter, Dako), collected and washed twice with RPMI medium containing 5% fetal calf serum. The mucosa was then digested in 20 ml of RPMI medium containing 1 g/ml dispase II (Roche Molecular Biochemicals) for two 30 minute incubation at 37° C. with vigorous shaking. Lymphocytes were collected, washed and labeled. Isolated T and B cells were labeled with FITC-conjugated anti-mouse CD3 and CD19, respectively.

To phenotype the T cells, lymphocytes were triple labeled with CD3, phycoerythrin-conujugated CD4 (specific for T helper cells) and tricolor-conjugated CD8 (specific for T suppressor cells). IFN-γ expression on CD8+ cells was analyzed by a double staining lymphocytes using FITC-conjugated anti-mouse IFN-γ. G-cells were detected with a [Lys3]-bombesin 14-Cy3 conjugate, parietal cells with an antibody specific for the $H^+$, $K^+$-ATPase and D-cells with a somatostatin antibody after permeabilization (Zavros et al., 2000). Labeled cells were then analyzed by flow cytometry using a Coulter Elite ESP Cell Sorter (Beckman-Coulter Electronics, Florida).

3. Immunohistochemistry and Peptide Assays

A longitudinal section of the stomach (spanning both the corpus and antral region) was fixed in 2% paraformaldehyde, embedded in paraffin and stained with hemotoxylin and eosin (H&E) or PAS/alcian blue.

After sacrifice, approximately 1 ml of blood was collected by cardiac puncture, aliquoted into lithium heparinized glass tubes (Becton Dickinson Vacutainer Systems, NJ) and centrifuged at 15,000 rpm for 15 minutes at 4° C. Plasma was collected and immediately stored at −20° C. until assayed. Gastrin was directly assayed using 50 µl of plasma (Shulkes & Read, 1991). Serum IL-8 levels were determined using a double-ligand ELISA kit according to the manufactures specifications (R&D Systems).

4. Statistics

At least 3 mice per treatment expressed as the mean±SEM. Statistical comparison between two groups was made by using an unpaired t-test. $P<0.05$ was considered significant.

B. Results

1. Verifying Mouse Colonization by *H. pylori* and Acinetobacter

*H. pylori* (HP) and Acinetobacter (AC) organisms were used to inoculate mice and study their effects on gastric pathology in parallel. To verify colonization of Acinetobacter in inoculated mice, a Western blot was performed on the bacteria cultured from the stomach. This demonstrated that Omp-A antiserum detects a 40 kDA protein expressed from the HS of cultures from mice inoculated with Acinetobacter, but not from stomach cultures of uninoculated animals. The percentages of subcultures, prepared from mice inoculated with Acinetobacter after 2, 3 and 4 months, that expressed the Omp-A protein were 0%, 50% and 100% respectively, as shown by the Western blot. The low detection rate for OmpA at earlier time points may reflect density dependent expression of the protein, since there was clearly an increase in the inflammatory response by two months that increased with longer colonization times (see below).

Sections of mouse stomachs from uninoculated mice or mice inoculated with *H. pylori* or Acinetobacter were stained for analyses using Warthin-Starry stain, H&E stain and PAS/alcian blue stain. The percentages of mice that were culture or Warthin-Starry positive for *H. pylori* was 73%. A representative Warthin-Starry stain demonstrated the presence of *H. pylori* in the gastric crypts. A Warthin-Starry stain of Acinetobacter infected mice showed large rod-shaped bacteria on the surface of the gastric mucosa.

H&E stains showed inflammation within the corpus mucosa (type A chronic gastritis) in both *H. pylori* and Acinetobacter infected mice. Mucous gland metaplasia was documented in mice infected for 2 or 3 months with *H. pylori* or Acinetobacter. PAS/alcian blue was used to document neutral and acid mucin present in both *H. pylori* and Acinetobacter infected mice.

Figure 8A:
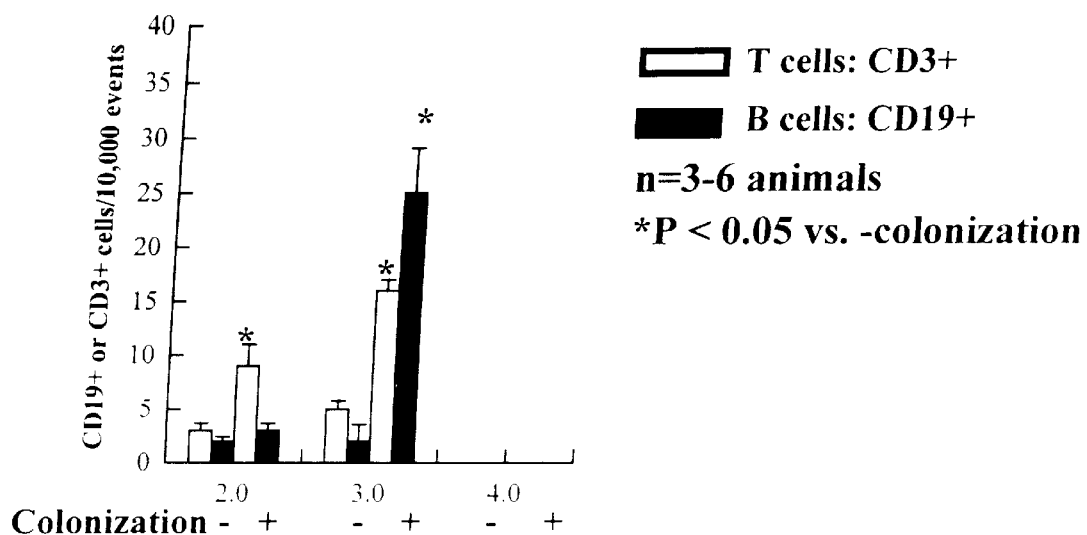
FIG. 8A and FIG. 8B. Flow cytometric analysis was used to analyze changes in gastric mucosal lymphocytes.
Figure 8B:
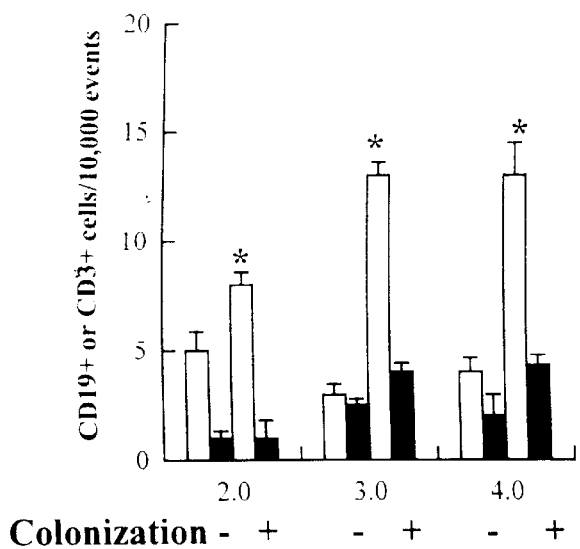

2. Elevated Lymphocytes in *H. pylori* and Acinetobacter Gastric Mucosa Colonization T cells increased by ~3-fold after two months of infection with *H. pylori* (FIG. 8A). After 3 months of infection there was a 5-fold increase in the number of T cells (FIG. 8A). Unlike Acinetobacter infection, the B cell population increased after 3 months of infection by 12-fold (FIG. 8A). Two months after inoculation with Acinetobacter, there was a nearly 2-fold increase in the number of T lymphocytes (FIG. 8B). These numbers continued to increase after 3 and 4 months of colonization a maximum of 4-fold above levels found in the uninoculated animals. There was no significant difference between B cell numbers (CD19+ cells) in the uninoculated versus the inoculated Acinetobacter mice (FIG. 8A).

Flow cytometric analysis was used to phenotype (subtype) the T cell response. It was found that there was an increase in the number of CD4+, CD8+ and CD8+ lymphocytes expressing IFN-γ cells in both *H. pylori* and Acinetobacter inoculated mice compared to uninoculated mice.

3. Plasma IL-8 Concentrations are Elevated in *H. pylori* and Acinetobacter Infection Increases were measured in plasma collected from *H. pylori* infected mice (Table 1). After 2 and 3 months there was a 3- and 2-fold increase in IL-8 concentrations, respectively. Similar plasma IL-8 concentrations were assayed in Acinetobacter infected mice. Table 1 shows that after 2 and 3 months there was an approximate 2-fold increase in IL-8 levels. After 4 months of colonization, IL-8 concentrations increased by approximately 4-fold in Acinetobacter infected animals compared to uninfected animals (Table 1).

TABLE 1

Changes in plasma IL-8 concentrations (pg/ml) in Acinetobacter or *H. pylori* infections

| Infection | Plasma IL-8 concentrations (pg/ml) | |
|---|---|---|
| | −colonization | +colonization |
| I. Acinetobacter | | |
| 2 months | 2016 ± 857 | 4998 ± 213* |
| 3 months | 2516 ± 191 | 4338 ± 677* |
| 4 months | 3130 ± 386 | 11300 ± 459* |
| II. *H. pylori* | | |
| 2 months | 2470 ± 473 | 6200 ± 232* |
| 3 months | 2435 ± 205 | 4998 ± 213* |

*$P<0.05$ vs −colonization

4. Changes in Neuroendocrine and Epithelial Cell Populations

Flow cytometric analysis was used to measure changes in neuroendocrine cell numbers after bacterial colonization. After 2 and 3 months of colonization with *H. pylori*, G-cells increased by 2.5- and 5-fold, respectively (FIG. 9A). There was a 6-fold decrease in the number of D-cells after 2 months of colonization with *H. pylori*. The decrease in D cells was sustained for up to 4 months (FIG. 9A). After 2, 3 and 4 months of Acinetobacter colonization, there was a 3- to 4-fold increase in the number of G-cells/10,000 events (FIG. 9C). The number of D-cells decreased 4 to 5-fold after Acinetobacter infection over the same time period (FIG. 9C).

Up to 4 months after *H. pylori* inoculation, parietal cell numbers also increased about 2-fold (FIG. 9B). Similarly, parietal cells also increased after 2-fold after 2 to 4 months of Acinetobacter colonization (FIG. 9D). Therefore, 4 months after inoculation by either bacteria, there was an increase in parietal cell numbers despite patches of atrophic glands scattered throughout the mucosa. Since the entire stomach was submitted for dissociation and analysis by flow cytometry, these results suggest that there is a greater increase in the proliferative rate in inflamed corpus mucosa.

Figure 10:
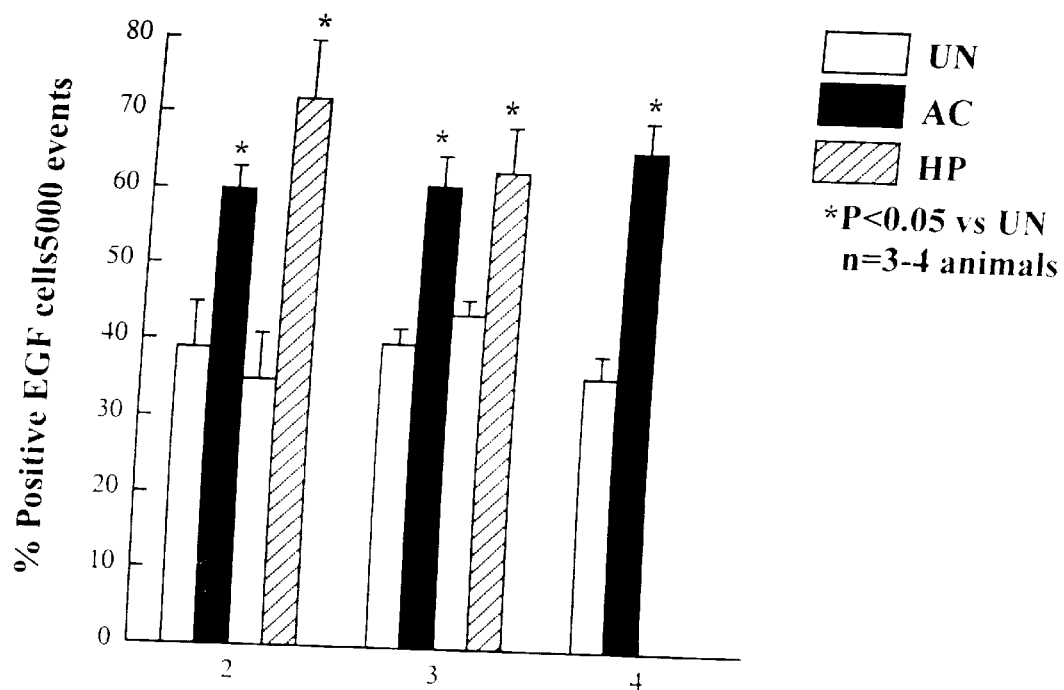
FIG. 10. Flow cytometric analysis was used to analyze the changes in cells expressing the EGF receptor (epithelial cell population). Number of EGF receptor positive cells increased in mice inoculated with Acinetobacter or *H. pylori* compared to uninoculated animals.

Consistent with this observation, the percentage of cells staining positive for EGF receptor also nearly doubled over the same 4 months period (FIG. 10). The number of Ki67 positive cells from uninoculated, *H. pylori* and Acinetobacter mice were also measured 3 months after inoculation.

5. Plasma Gastrin Elevation During *H. pylori* and Acinetobacter Infection

Table 2 summarizes the plasma gastrin concentrations measured after 2, 3 and 4 months of colonization with either *H. pylori* or Acinetobacter. After 2 and 3 months of *H. pylori* infection, plasma gastrin concentrations increased by 7- and 4-fold, respectively (Table 2). Similarly, after 2, 3 and 4 months of Acinetobacter infection, plasma gastrin levels increased by 3-, 5- and 6-fold, respectively (Table 2).

TABLE 2

Changes in plasma gastrin concentrations (pmol/l) in Acinetobacter or *H. pylori* infections

| Infection | Plasma gastrin concentrations (pmol/l) | |
|---|---|---|
| | −colonization | +colonization |
| I. Acinetobacter | | |
| 2 months | 50 ± 16 | 153 ± 64* |
| 3 months | 38 ± 3 | 186 ± 63* |
| 4 months | 35 ± 3 | 222 ± 55* |
| II. *H. pylori* | | |
| 2 months | 56 ± 23 | 383 ± 99* |
| 3 months | 44 ± 10 | 195 ± 36* |

$P<0.05$ vs −colonization

C. DISCUSSION

Conditions such as gastritis, peptic ulcers and gastric carcinoma are often associated with the colonization of *H. pylori* in the stomach. However, although colonization with bacteria other than *H. pylori* was possible, such colonization and the effects on the gastric mucosa were not studied prior to the present invention. This study demonstrates that bacterial colonization of the mouse stomach with Acinetobacter will cause a pathologic and histological response that mimics that of infection by *H. pylori*. Colonization of the stomach by Acinetobacter caused an inflammatory response reflected by an increase in T lymphocytes. However, unlike *H. pylori*, there was no change in the B-cell population after 4 months of Acinetobacter infection. Bacterial infection by either organism increased the number of G and parietal cells with a concomitant decrease in the number of D-cells. In addition, after a two month infection with *H. pylori* or Acinetobacter, parietal cell atrophy and mucous gland metaplasia was observed.

Although both Acinetobacter and *H. pylori* infections caused an increase in the number of T cells (CD3+), an increase in the number of B cells (CD19+) was observed in *H. pylori* infected mice. However, the stimulation of a B cell response by Acinetobacter inoculation may be time dependent, since 12 months of infection with a mixed bacterial culture containing Acinetobacter spp. significantly stimulated the number of B cells. These results are consistent with the activation of a clonal B-cell population by T helper cell activity in mucosa associated lymphoid tissue (MALT) lymphoma (D'Elios et al., 1999; Terres and Pajares, 1998). Even though there is a 95% association between *H. pylori* infection and MALT lymphoma, others showed the presence of bacterial overgrowth by non-*H. pylori* organisms in these patients (Jonkers et al., 1997).

In the mouse, there was an increase in parietal cell number during both *H. pylori* and Acinetobacter infection. In support of this, findings in patients with gastrin-producing tumors associated with Zollinger-Ellison syndrome showed hypergastrinemia resulting in an increase in the thickness of the acid secreting mucosa and the number of parietal cells (Komorowski and Caya, 1991; Helander et al., 1992). In addition, corpus atrophy has been reported in human *H. pylori* studies as well as mouse models using *H. felis*; however, both studies also reported an increase in the mucosal proliferative rate (Peek et al., 1997; Wang et al., 1998). However, in the human study, atrophy was explained by an increase in the apoptotic over the proliferative rate (Wang et al., 1998). Whereas, in the mouse model, the proliferative rate was greater than that for apoptosis (Peek et al., 1997). Therefore, despite parietal cell atrophy, there is presumably an increase in the overall rate of proliferation in the gland, and there is conflicting evidence for the effects of H. pylori infection on apoptosis. Although these studies associate hypergastrinemia with parietal cell changes, the present study is the first to show that this effect is not H. pylori specific. Both Acinetobacter and H. pylori infection caused the same level of inflammation. The increase in the number of T cells was reflected by an increase in plasma IL-8 concentrations. It has now been accepted that patients infected with H. pylori eventually develop chronic gastric inflammation and atrophic gastritis, conditions that are characterized by infiltration of the gastric submucosa and lamina propria by T cells and macrophages (D'Elios et al., 1999; Dixon et al., 1996; Judd et al., 1999; Mattapallil et al., 2000; Roth et al., 1999; Zhang et al., 1999). Furthermore, prolonged IL-8 production by gastric epithelial cells and elevated T cells during H. pylori infection, is consistent with the observed histological abnormalities in the gastric mucosa (Bamford et al., 1998; Judd et al., 1999; Masamune et al., 1999).

The present studies show that non-H. pylori bacteria can colonize the mouse stomach thus causing gastric inflammation. The susceptibility of H. pylori versus Acinetobacter infection in the human stomach is dependent on the gastric pH. H. pylori survives in the human stomach under low pH conditions (pH 2), creating an alkaline microenvironment through its production of urease. Although Acinetobacter has variable urease activity, this bacterial species is known to colonize the achlorhydric stomach (Graevenitz, 1995; Sharma et al., 1984). This work and Koh et al (1997) showed that the pH of the mouse stomach is 4.2.

Increased gastric pH in the human stomach results in bacterial overgrowth (Haruma et al., 1995; Lehy et al., 2000; Stockbruegger et al., 1984). As a consequence of bacterial overgrowth, there is the development of inflammation and atrophic gastritis (Haruma et al., 1995; Lehy et al., 2000; Stockbruegger et al., 1984). Patients with pernicious anemia, thought to be achlorhydric due to anti-parietal cell antibodies, exhibit bacterial overgrowth (Haruma et al., 1995; Lehy et al., 2000; Stockbruegger et al., 1984; Toh et al., 1997), and Acinetobacter was isolated from the gastric contents of healthy volunteers made achlorhydric through the administration of omeprazole (Sharma et al., 1984). In addition, H. pylori infection is infrequent in pernicious anemia patients (Fong et al., 1991; Haruma et al., 1995), which may be due to achlorhydria resulting in the overgrowth of other bacteria. Therefore, evidence reveals that gastric inflammation and atrophic gastritis is not specific for H. pylori.

Based on the pattern of cytokine expression CD4+ and CD8+ T cells have been classified as T helper (Th)1 T cells. The cytokines are predominantly released after a Th1 type of inflammatory response (Mattapallil et al., 2000). The Th1 type response is the predominant inflammatory response detected during H. pylori infection in man (Mattapallil et al., 2000) and mouse (Bamford et al., 1998; Lee, 1999). Therefore the Acinetobacter infection seems to mimic this process.

In this study, CD8+ cells expressing IFN-γ increased with Acinetobacter infection. Such an observation is typical of a Th1 immune response activated during H. pylori infection (Bamford et al., 1998; Mohammadi et al., 1996; Strober et al., 1997). Furthermore, immunization against IFN-Y resulted in a reduction of gastric inflammation in H. pylori infected mice (Mohammadi et al., 1996). It is also important to note that increased IFN-γ expression during H. pylori infection correlates with an increase in gastrin secretion both in vivo and in vitro (Jassel et al., 1999; Lehmann et al., 1996). The present study also correlates an increase in IFN-γ expression with increased plasma gastrin and G-cell numbers. In addition, a study using isolated canine antral G cells showed stimulation in gastrin release by IFN-γ (Lehmann et al., 1996).

The present study demonstrates that like H. pylori, Acinetobacter causes a significant increase in plasma gastrin concentrations. The pattern of hypergastrinemia associated with H. pylori infection may be due to a lack of inhibitory influence of somatostatin (SOM). Furthermore, it is known that D-cells contain neuronal nitric oxide synthase that regulates apoptosis of G-cells (Larsson, 2000). This is supported by the present findings of decreased D-cells and increased G-cell numbers during both H. pylori and Acinetobacter infection. This lack of inhibition is supported by studies showing that SOM content in antral biopsies collected from H. pylori positive patients is significantly lower compared to uninfected patients (Haruma et al., 1995; Odum et al., 1994). Furthermore, the eradication of H. pylori results in an increased number of antral SOM immunoreactive (D-) cells and increased expression of SOM mRNA (Moss et al., 1992; Queiroz et al., 1994). Although the data on SOM and H. pylori infection correlates with the D cell as the initial target, genetic mouse models deficient in gastrin or SOM may shed light on whether bacteria directly affects G and D cells.

Therefore, the present study demonstrates that atrophic gastritis and gastric inflammation is not specific for H. pylori infection. In the mouse, Acinetobacter, a known human pathogen, is able to colonize the stomach and cause gastric atrophy and inflammation, similar to that of H. pylori. The study has clinical relevance to patients with low gastric acid secretion either due to disease such as pernicious anemia, or acid suppressant drugs. These patients are known to have bacterial overgrowth correlating with atrophic gastritis and inflammation. Acinetobacter also likely has a role in the observed atrophy and inflammation in achlorhydric patients.

EXAMPLE III

Prevention of Acinetobacter-Mediated Mucosal Inflammatory Changes

A. Immunoneutralization Prevents Mucosal Inflammatory Changes

This study shows that immunoneutralization using antisera against Acinetobacter Omp-A prevented the mucosal inflammatory changes triggered by Acinetobacter. The OmpA antibody used here was raised against the extreme C-terminal domain of the OmpA protein, as described in Example I.

To determine whether the inflammatory changes by Acinetobacter were due to the Omp-A protein, Omp-A antiserum was incubated with the bacteria prior to inoculation. To verify colonization, mouse stomachs were rinsed with phosphate buffered saline (PBS) and the resulting rinse diluted 1:10 in PBS. 100 µl of the diluted rinse was plated on LB plates and incubated at 37° C. for 24 h. The rinses were obtained from mice that were inoculated with a 1:50 dilution of either pre-immune plus Acinetobacter or OmpA immune serum plus Acinetobacter. About ~200 bacterial colonies per plate grew at the 1:50 dilution of both pre-immune and immune samples. At the 1:500 dilution, there were ~800 colonies per plate counted. At the 1:5000 dilution, there were ~4000 colonies per plate. There was an increase in the number of colonies per plate with an increase in the dilution of the pre-immune and immune serum.

Flow cytometric analysis was used to quantify the changes in T cell populations after immunoneutralization. T cells were measured using a CD3+ specific antibody and T helper and suppressor cells were analyzed using CD4+ and CD8+ specific antibodies. At a 1:50 dilution of pre-immune serum, total T-cells (T), T-helper (Th) and T-suppressor (Ts) cells increased by 7-, 3- and 5-fold respectively compared to uninoculated mice (FIG. 11A). The IFN-Y expressing cells were also elevated 12-fold compared to uninoculated mice (FIG. 11A). At a 1:50 dilution of immune serum, T-, Th- and Ts-cells decreased by ~2-fold compared to pre-immune animals, but there was no significant difference between uninoculated and immune sera treated mice (FIG. 11A). IFN-γ expression by CD8+ cells was also significantly lower compared to pre-immune animals (FIG. 11A). At concentrations of 1:500 and 1:5000 there was no significant difference between pre-immune and immune T cell populations, and these numbers were also significantly greater than uninoculated animals (FIG. 11B and FIG. 11C). Histograms of CD4+, CD8+ cells and IFN-γ expressing cells were also generated.

Table 3 summarizes the plasma IL-8 concentrations measured after immunoneutralization with the Acinetobacter OMP-A antibody. Measurement of serum IL-8 gives a quantitative indication of the degree of the inflammatory response. Mice inoculated with pre-immune serum plus Acinetobacter exhibited IL-8 concentrations that were not significantly different from uninfected mice (Table 3). IL-8 concentrations measured in plasma from mice inoculated with immune serum plus Acinetobacter showed concentrations significantly lower than those of uninoculated mice at a 1:50 dilution (Table 3). At the 1:500 and 1:5000 dilutions, there was no significant difference between IL-8 concentrations measured in uninfected, pre-immune or immune (Table 3).

TABLE 3

Plasma IL-8 concentrations (pg/ml) after immunoneutralization

| Treatment | Plasma IL-8 concentrations (pg/ml) | | |
|---|---|---|---|
| | UN | PI | I |
| 1/50 | 1867 ± 318 | 2100 ± 100 | 1300 ± 153 |
| 1/500 | NA | 2000 ± 152 | 1900 ± 306 |
| 1/5000 | NA | 2500 ± 362 | 2400 ± 208 |

NA: not applicable, NI: noninfected, PI: pre-immune, I: immune

B. Cell Populations after Immunoneutralization

Figure 12A:
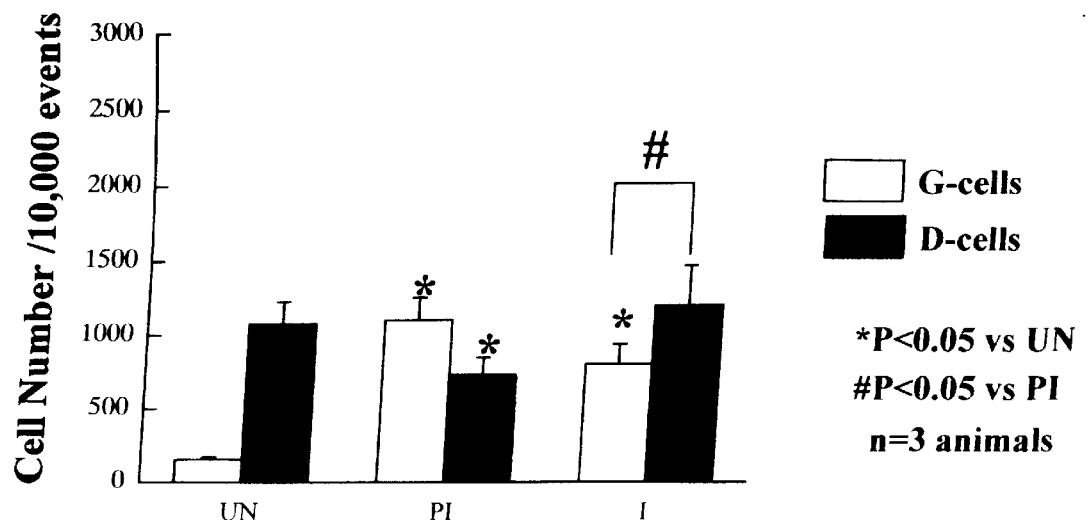
FIG. 12A, FIG. 12B and FIG. 12C. Quantified changes in the gastric epithelial cell population after immunoneutralization of Acinetobacter. The number of G- and D-cells was analyzed in gastric cell populations isolated from uninoculated (UN) mice and mice inoculated with 1:50 (FIG. 12A), 1:500 (FIG. 12B) and 1:5000 (FIG. 12C) dilutions of pre-immune (PI) and immune (I) serum.
Figure 12B:
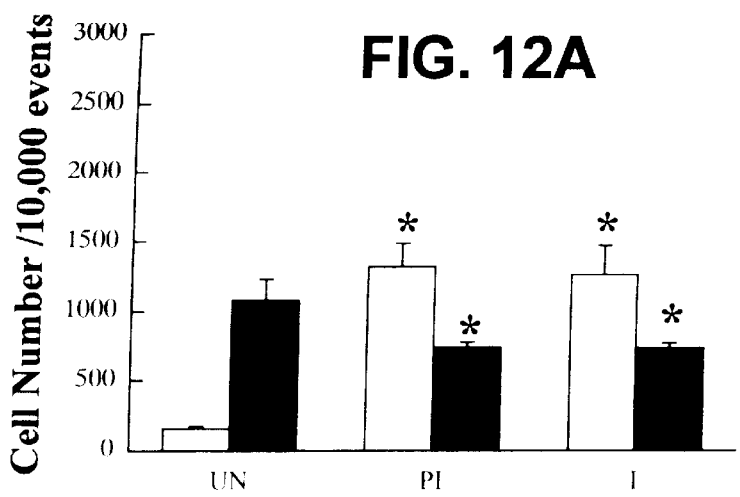
Figure 12C:
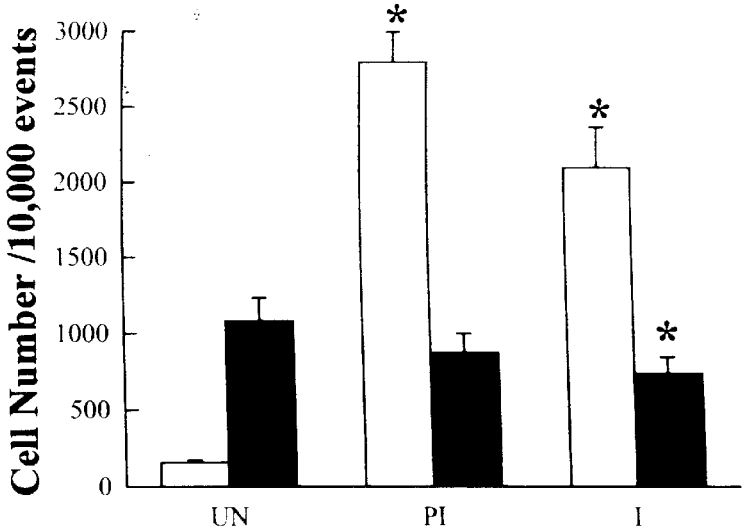

After immunoneutralization, there was a decrease in the number of G-cells with an observed increase in the D-cell population. At a 1:50 dilution of pre-immune serum plus Acinetobacter, there was a 5-fold increase in the number of G-cells compared to the uninoculated animals (FIG. 12A). Although there was a 4-fold increase in the number of G-cells in the immune animals compared to the uninoculated mice, these numbers were significantly lower in the animals receiving the mixture of Acinetobacter with the pre-immune sera (FIG. 12A). D-cell numbers were similar for both uninoculated and immune animals, while numbers were significantly lower in the pre-immune mice (FIG. 12A). At 1:500 and 1:5000 dilutions of pre-immune and immune serum, G-cell numbers were significantly greater, and D-cells lower, compared to uninoculated animals (FIG. 12B and FIG. 12C).

C. Plasma Gastrin Concentrations

Table 4 summarizes the plasma gastrin concentrations measured after immunoneutralization of the effects of Acinetobacter Omp-A on gastrin secretion. Mice inoculated with 1:50 dilution of pre-immune and immune serum plus Acinetobacter showed significantly greater plasma gastrin concentrations compared to the uninoculated animals (Table 4). At a 1:500 dilution, gastrin levels measured in plasma from the immune animals were significantly lower compared to the pre-immune animal (Table 4). At a 1:5000 dilution, there was no difference between pre-immune and immune animals with respect to plasma gastrin levels (Table 4).

TABLE 4

Changes in plasma gastrin concentrations (pmol/l) after immunoneutralization

| Treatment | Plasma gastrin concentrations (pmol/l) | | |
|---|---|---|---|
| | UN | PI | I |
| 1/50 | 34 ± 0.58 | 52 ± 1.53 | 83 ± 9.50 |
| 1/500 | NA | 158 ± 19.0 | 89 ± 10.1 |
| 1/5000 | NA | 170 ± 71.3 | 169 ± 45.0 |

NA: not applicable, NI: noninfected, PI: pre-immune, I: immune

D. Conclusions

Although there are some nonspecific effects from the preimmune sera at the lower concentration of antibody (1:50), particularly on the G cell population and less on the T cell populations and IL-8 levels, the 1:500 dilution demonstrated an inhibition of both the inflammatory parameters as well as the neuroendocrine changes with OmpA antiserum. Collectively, these studies show that neutralization of the OmpA of Acinetobacter blocks the immune and neuroendocrine, and perhaps also the histological, changes induced by this organism. These studies also show that immunoneutralizing OmpA antibodies, such as those raised against the extreme C-terminal domain of the OmpA protein, are useful therapeutic and diagnostic tools for patients infected with Acinetobacter and for treating and diagnosing the variety of associated diseases.

All of the compositions and methods disclosed and claimed herein can be made and executed without undue experimentation in light of the present disclosure. While the compositions and methods of this invention have been described in terms of certain preferred embodiments, it will be apparent to those of skill in the art that variations may be applied to the compositions and methods and in the steps or in the sequence of steps of the methods described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Alm, Ling, Moir et al., "Genomic-sequence comparison of two unrelated isolates of the human gastric pathogen *Helicobacter pylori*," *Nature*, 397:176–80, 1999.

*Antibodies: A Laboratory Manual*, Cold Spring Harbor Laboratory, 1988.

Bamford et al., "Lymphocytes in the human gastric mucosa during *Helicobacter pylori* have a T helper cell 1 phenotype," *Gastroenterology*, 114:482–92, 1998.

Barranco, Townsend Jr., Casartelli et al., "Establishment and characterization of an in vitro model system for human adenocarcinoma of the stomach," *Cancer Res.*, 43:1703–1709, 1983.

Bartsch et al., "Endogenously formed N-nitroso compounds and nitrosating agents in human cancer etiology," *Pharmacogenetics*, 2:272–7, 1992.

Beher et al, "Major heat-modifiable outer membrane protein in gram-negative bacteria: comparison with the OmpA protein of *Escherichia coli*," *J Bacteriol*, 143:906–913, 1980.

Behrmann et al., "Requirements for the translocation of elongation-arrested, ribosome-associated OmpA across the plasma membrane of *Escherichia coli*," *J. Biol. Chem.*, 273:13898–904, 1998.

Blaser and Parsonnet, "Parasitism by the 'slow' bacterium *Helicobacter pylori* leads to altered gastric homeostasis and neoplasia," *J. Clin. Invest.*, 94:4–8, 1994.

Bradford, "A rapid and sensitive method for the quantitation of microgram quantities of protein utilizing the principle of protein-dye binding," *Anal. Biochem.*, 72:248–254, 1976.

Brand and Stone, "Reciprocal regulation of antral gastrin and somatostatin gene expression by omeprazole-induced achlorhydria," *J. Clin. Invest.*, 82:1059–1066, 1988.

Brutlag et al., *CABIOS*, 6:237–245, 1990.

Campbell, In: *Monoclonal Antibody Technology, Laboratory Techniques in Biochemistry and Molecular Biology*, Vol. 13, Burden and Von Knippenberg, Eds. pp. 75–83, Amsterdam, Elseview, 1984.

Carrick et al., *Gut*, 30:790–797, 1989.

Chou and Fasman, "Prediction of Protein Conformation," *Biochemistry*, 13(2):222–245, 1974a.

Chou and Fasman, "Conformational Parameters for Amino Acids in Helical, P-Sheet, and Random Coil Regions Calculated from Proteins," *Biochemistry*, 13(2):211–222, 1974b.

Chou and Fasman, "Prediction of the Secondary Structure of Proteins from Their Amino Acid Sequence," *Adv. Enzymol. Relat. Areas Mol. Biol.*, 47:45–148, 1978a.

Chou and Fasman, "Empirical Predictions of Protein Conformation," *Ann. Rev. Biochem.*, 47:251–276, 1978b.

Chou and Fasman, "Prediction of β-Turns," *Biophys. J.*, 26:367–384, 1979.

Conteas et al., "Relationship of hormones and growth factors to colon cancer," *Gastroenterol. Clin. North Am.*, 17:761–772, 1988.

Cox et al., *J. Virol.* 67(9):5664–5667, 1993.

Crabtree, "Role of cytokines in pathogenesis of *Helicobacter pylori*-induced mucosal damage," *Dig. Dis. Sci.*, 43 (Supplement):46S–53S, 1998.

Craven et al., "Nosocomial pneumonia in the 1990s: update of epidemiology and risk factors," *Semin. Respir. Infect.*, 5:157–72, 1990.

*Current Protocols in Molecular Biology*, 1995.

D'Elios et al., "Impaired T-Cell Regulation of B-Cell Growth in *Helicobacter pylori*- Related Gastric Low-Grade MALT Lymphoma," *Gastroenterology*, 117:1105–1112, 1999.

Dixon et al., "Classification and grading of gastritis. The updated Sydney System. International Workshop on the Histopathology of Gastritis, Houston 1994," *Am. J. Surg. Pathol.*, 20:1161–81, 1996.

Dockray, "Topical review. Gastrin and gastric epithelial physiology," *J. Physiol. (Lond)*, 518:315–24, 1999.

Doig and Trust, "Identification of surface-exposed outer membrane antigens of *Helicobacter pylori*," *Infect. Immun.*, 62:4526–33, 1994.

Duffaud, "Signal peptidases recognize a structural feature at the cleavage site of secretory proteins," *J. Biol. Chem.*, 263:10224–8, 1988.

Elliott et al., "Bacteria rapidly colonize and modulate healing of gastric ulcers in rats," *Am. J. Physiol.*, 275:G425–32, 1998.

Exner et al., "Isolation and characterization of a family of porin proteins from *Helicobacter pylori*," *Infect. Immun.*, 63:1567–72, 1995.

Farinati et al., "Prevalence of *Helicobacter pylori* infection in patients with precancerous changes and gastric cancer," *Eur. J. Cancer Prev.*, 2:321–6, 1993.

Fetrow & Bryant, "New Programs for Potein Tertiary Structure Prediction," *BIOTECHNOLOGY*, 11:479–483, 1993.

Finley et al., "Expression of the gastrin gene in the normal human colon and colorectal adenocarcinoma," *Cancer Res.*, 53:2919–26, 1993.

Fong et al., "*Helicobacter pylori* infection in pernicious anemia: a prospective controlled study," *Gastroenterology*, 100:328–32, 1991.

Ford, Valle, Soroka, Merchant, "EGF receptor activation stimulates endogenous gastrin gene expression in canine G cells and human gastric cell cultures," *J. Clin. Invest.*, 99:2762–71, 1997.

Freifelder, "Translation I: The Information Problem," In Molecular Biology, Second ed. Jones and Bartlett, Portola Valley, Calif., D. Freifelder (ed.), 1983, p. 367–413.

Frohman, M. A., In: PCR™ Protocols: *A Guide To Methods And Applications*, Academic Press, N.Y., 1990.

Fynan et al., "DNA vaccines: Protective immunizations by parenteral, mucosal, and gene-gun inoculations," *Proc. Natl. Acad. Sci. USA*, 90:11478–11482, 1993.

Garrouste-Orgeas et al., "Oropharyngeal or gastric colonization and nosocomial pneumonia in adult intensive care unit patients. A prospective study based on genomic DNA analysis," *Am. J. Respir. Cri.t Care Med.*, 156:1647–55, 1997.

Gefter et al., *Somatic Cell Genet.* 3:231–236, 1977.

Ghiara et al., "Therapeutic intragastric vaccination against *Helicobacter pylori* in mice eradicates an otherwise chronic infection and confers protection against reinfection," *Infect. Immun.*, 65:4996–5002, 1997.

Goding, In: *Monoclonal Antibodies: Principles and Practice*, 2d ed., Orlando, Fla., Academic Press, pp. 60–61, 65–66, 71–74, 1986.

Graevenitz, "Acinetobacter, Alcaligenes, Moraxella, and other nonfermentating gram-negative bacteria," *In P. R. Murray (ed.), Manual of Clinical Microbiology. American Society for Microbiology, Washington, DC.*, p. 520–532, 1995.

Graham, "Antibiotic resistance in *Helicobacter pylori*: implications for therapy [In Process Citation]," *Gastroenterology*, 115:1272–7, 1998.

Graham et al., "Antral G-cell and D-cell numbers in *Helicobacter pylori* infection: Effect of *H. pylori* eradication," *Gastroenterology*, 104:1655–1660, 1993.

Hamlet, Thoreson, Nilsson, Svennerholm, Olbe, "Duodenal *Helicobacter pylori* infection differs in cagA genotype between asymptomatic subjects and patients with duodenal ulcers," *Gastroenterology*, 116:259–68, 1999.

Haruma et al., "Pernicious anemia and *Helicobacter pylori* infection in Japan: evaluation in a country with a high prevalence of infection," *Am, J. Gastroenterol*, 90:1107–10, 1995.

Helander et al., "Stereologic investigations of human gastric mucosa. II. Oxyntic mucosa from patients with Zollinger-Ellison syndrome," *Scand. J. Gastroenterol*, 27:875–83, 1992.

Houben and Stockbrugger, "Bacteria in the aetiopathogenesis of gastric cancer: a review," *Scand. J. Gastroenterol. Suppl.*, 212:13–8, 1995.

Hsiao et al., "Outer membrane protein CD of Branhamella catarrhalis: sequence conservation in strains recovered from the human respiratory tract," *Microb. Pathog.*, 19:215–25, 1995.

Jameson and Wolf, "The Antigenic Index: A Novel Algorithm for Predicting Antigenic Determinants," *Comput. Appl. Biosci.*, 4(1):181–186, 1988.

Jassel et al., ."The rise in circulating gastrin with age is due to increases in gastric autoimmunity and *Helicobacter pylori* infection," *Qjm.*, 92:373–7, 1999.

Johnson et al., "Peptide Turn Mimetics" in *Biotechnology and Pharmacy*, Pezzuto et al., Eds., Chapman and Hall, New York, 1993.

Jonkers et al., "*Helicobacter pylori* and non-*Helicobacter pylori* bacterial flora in gastric mucosal and tumour specimens of patients with primary gastric lymphoma," *Eur. J. Clin. Invest*, 27:885–92., 1997

Judd et al., "Autoimmune gastritis results in disruption of gastric epithelial cell development," *Am, J. Physiol.*, 277:G209-18, 1999.

Keates, Hitti, Upton, Kelly, "*Helicobacter pylori* infection activates NF-kB in gastric epithelial cells," *Gastroenterology*, 113:1099–1109, 1997.

Kennell et al., "Pore-forming ability of major outer membrane proteins from Wolinella recta ATCC 33238," *Infect. Immun.*, 60:380–4, 1992.

Khanolkar-Gaitonde,et al., "Isolation of bacteria other than *Helicobacter pylori* from stomachs of squirrel monkeys (Saimiri spp.) with gastritis [In Process Citation]," *Dig. Dis. Sci.*, 45:272–80, 2000.

Koh et al., "Gastrin deficiency results in altered gastric differentiation and decreased colonic proliferation in mice," *Gastro.*, 113:1015–1025, 1997.

Kohler and Milstein, *Nature*, 256:495497, 1975.

Kohler and Milstein, *Eur. J. Immunol.*, 6:511–519, 1976.

Komatsuzawa et al., "Cloning of the gene encoding the *Actinobacillus actinomycetemcomitans* serotype b OmpA-like outer membrane protein," *Infect. Immun.*, 67:942–5, 1999.

Komorowski and Caya, "Hyperplastic Gastropathy. Clincal correlation," *Am, J. Surg. Pathol.*, 15:577–585, 1991.

Kuipers, "Review article: exploring the link between *Helicobacter pylori* and gastric cancer," *Aliment. Pharmacol. Ther.*, 13 Suppl 1:3–11, 1999.

Kyte and Doolittle, "A simple method for displaying the hydropathic character of a protein". *J. Mol Biol.*, 157(1): 105–132, 1982.

Lane et al., "Rapid determination of 16S ribosomal RNA sequences for phylogenetic analyses," *Proc. Natl. Acad. Sci USA.*, 82:6955–9, 1985.

Larsson, "Developmental biology of gastrin and somatostatin cells in the antropyloric mucosa of the stomach," *Microsc. Res. Tech.*, 48:272–81, 2000.

Lawrence et al., "Molecular and evolutionary relationships among enteric bacteria," *J. Gen. Microbiol.*, 137:1911–21, 1991.

Lee, "Animal models of Helicobacter infection," *Mol. Med. Today*, 5:500–1, 1999.

Lee, O'Rourke, Ungria, Robertson, Daskalopoulos, Dixon, "A standardized mouse model of *Helicobacter pylori* infection: Introducing the Sydney Strain," *Gastroenterology*, 112:1386–1397, 1997.

Lehmann et al., "Mononuclear cells and cytokines stimulate gastrin release from canine antral 0 cells in primary culture," *Am, J. Physiol.*, 270:G783–8, 1996.

Lehy et al. "Histomorphological characteristics of gastric mucosa in patients with zollinger-ellison syndrome or autoimmune gastric atrophy: role of gastrin and atrophying gastritis," *Microsc. Res. Tech.*, 48:327–38, 2000.

Marchetti, Aricò, Burroni, Figura, Rappuoli, Ghiara, "Development of a mouse model of *Helicobacter pylori* infection that mimics human disease," *Science*, 267:1655–1658, 1995.

Marshall et al., "A conserved retinoic acid response element required for early expression of the homeobox gene Hoxb-1," *Nature*, 370:567–571, 1994.

Masamune et al., "*Helicobacter pylori*-dependent ceramide production may mediate increased interleukin 8 expression in human gastric cancer cell lines," *Gastroenterology*, 116:1330–41, 1999.

Mattapallil et al., "A predominant Th1 type of immune response is induced early during acute *Helicobacter pylori* infection in rhesus macaques," *Gastroenterology*, 118:307–15, 2000.

McCloy et al., "Pathophysiological effects of long-term acid suppression in man," Dig Dis. Sci, 40:96S-120S, 1995.

Mohammadi et al., "Helicobacter-specific cell-mediated immune responses display a predominant Th1 phenotype and promote a delayed-type hypersensitivity response in the stomachs of mice," *J. Immunol.*, 156:4729–38, 1996.

Moran, "Pathogenic properties of *Helicobacter pylori*," Scand *J. Gastroenterol Suppl.*, 215:22–31, 1996.

Moss, Legon, Bishop, Polak, Calam, "Effect of *Helicobacter pylori* on gastric somatostatin in duodenal ulcer disease," *Lancet*, 340:930–932, 1992.

Moss, Legon, Davies, Calam, "Cytokine gene expression in *Helicobacter pylori* associated antral gastritis," *Gut*, 35:1567–1570, 1994.

Mukaida et al., "Genomic sturcture of the human monocyte-derived neutrophil chemotactic factor IL-8," *J. Immunol.*, 143:1366–1371, 1989.

Murphy et al., "The major heat-modifiable outer membrane protein CD is highly conserved among strains of *Branhamella catarrhalis.*," *Mol. Microbiol.*, 10:87–97, 1993.

Murphy et al., "Analysis of antigenic structure and human immune response to outer membrane protein CD of *Moraxella catarrhalis*," *Infect. Immun.*, 67:4578–85, 1999.

Nakamura et al., In: *Enzyme Immunoassays: Heterogeneous and Homogeneous Systems*, Chapter 27.

Nguyen et al., "Chromosomal sequencing using a PCR-based biotin-capture method allowed isolation of the complete gene for the outer membrane protein A of *Klebsiella pneumoniae*," Gene, 210:93–101, 1998.

Nomura et al., "*Helicobacter pylori* infection and gastric carcinoma among Japanese Americans in Hawaii," *N. Engl. J. Med*, 325:1132–1136,1991.

Odum et al., "Gastrin and somatostatin in *Helicobacter pylori* infected antral mucosa," *Gut.*, 35:615–8, 1994.

Ofori-Darko et al., "An OmpA-like protein from Acinetobacter stimulates the gastrin and IL-8 promoters," *Infection and immunity*, 68:3657–3666, 2000.

Ohnishi et al., "Characterization of a heat modifiable protein, *Escherichia coli* outer membrane protein OmpA in binary surfactant system of sodium dodecyl sulfate and octylglucoside,"*Biochim. Biophys. Acta.*, 1375:101–9, 1998.

Ortiz et al., "Immunoblot detection of class-specific humoral immune response to outer membrane proteins isolated from Salmonella typhi in humans with typhoid fever," *J. Clin. Microbiol.,*" 27:1640–5, 1989.

PCR™ *Protocols: A Guide to Methods and Applications*, Academic Press, N.Y., 1990.

Peek et al., "Helicobacter pylori cagA+ strains and dissociation of gastric epithelial cell proliferation from apoptosis," *J. Natl. Cancer Inst.*, 89:863–8, 1997.

Pratap and Dikshit, "Effect of signal peptide changes on the extracellular processing of streptokinase from *Escherichia coli*: requirement for secondary structure at the cleavage junction," *Mol. Gen. Genet.*, 258:326–33, 1998.

Puohiniemi et al., "A strong antibody response to the periplasmic C-terminal domain of the OmpA protein of *Escherichia coli* is produced by immunization with purified OmpA or with whole *E. coli* or *Salmonella typhimurium* bacteria," *Infect. Immun.*, 58:1691–6, 1990.

Queiroz et al., "Effect of *Helicobacter pylori* eradication of G-cell and D-cell density in children," *Lancet.*, 343:1191–1193, 1994.

Rawling et al., "Roles of the carboxy-terminal half of *Pseudomonas aeruginosa* major outer membrane protein OprF in cell shape, growth in low-osmolarity medium, and peptidoglycan association," *J. Bacteriol.*, 180:3556–62, 1998.

Roth et al., "Cellular immnune responses are essential for the development of *Helicobacter felis*-associated gastric pathology," *J. Immunol*, 163:1490–7, 1999.

Safatle-Ribeiro et al., "Relationship between persistence of *Helicobacter pylori* and dysplasia, intestinal metaplasia, atrophy, inflammation, and cell proliferation following partial gastrectomy," *Dig. Dis. Sci.*, 44:243–52, 1999.

Sambrook, Fritsch, Maniatis, *Molecular Cloning: A Laboratory Manual*, 2nd Ed., Cold Spring Harbor Press, Cold Spring Harbor, N.Y., 1989.

Saunders et al., "Simple sequence repeats in the *Helicobacter pylori* genome," *Mol. Microbiol.*, 27:1091–8, 1998.

Seery, "Achlorhydria and gastric carcinogenesis," *Lancet.*, 338:1508–9, 1991.

Sharma et al., "Intragastric bacterial activity and nitrosation before, during, and after treatment with omeprazole," *Br. Med. J. (Clin. Res. Ed).*, 289:717–9, 1984.

Singh et al., "Gastrin gene expression is required for the proliferation and tumorigenicity of human colon cancer cells," *Cancer Res.*, 56:4111–4115, 1996.

Stockbruegger et al., "Pernicious anaemia, intragastric bacterial overgrowth, and possible consequences," *Scand. J. Gastroenterol*, 19:355–64, 1984.

Strober et al., "Reciprocal IFN-gamma and TGF-beta responses regulate the occurrence of mucosal inflammation," *Immunol. Today*, 18:61–4, 1997.

Sumii et al., "Expression of antral gastrin and somatostatin mRNA in *Helicobacter pylori*-infected subjects," *Am, J. Gastroenterol.*, 89:1515–1519, 1994.

Tang et al., *Nature*, 356:152–154, 1992.

Terres and Pajares, "An increased number of follicles containing activated CD69+ helper T cells and proliferating CD71+B cells are found in *H. pylori*-infected gastric mucosa," *Am. J. Gastroenterol*, 93:579–83, 1998.

Toh et al., "Mechanisms of disease," *New Eng. J. Med.*, 337:1441–1448, 1997.

Tomb, White, Kerlavage et al., "The complete genome sequence of the gastric pathogen *Helicobacter pylori*," Nature, 388:539–547, 1998.

Torres et al., "Stomach as a source of colonization of the respiratory tract during mechanical ventilation: association with ventilator-associated pneumonia." *Eur. Respir. J*, 9:1729–35, 1996.

Ulmer et al., "Heterologous Protection Against Influenza by Injection of DNA Encoding a Viral Protein," *Science*, 259:1745–1749, 1993.

Walsh and Grossman, "Gastrin," *N. Engl. J. Med.*, 292 pt 2:1377–1384, 1975.

Wang et al., *Proc. Natl. Acad. Sci. USA*, 90:4156–4160, 1993.

Wang et al., "Mice lacking secretory phospholipase A2 show altered apoptosis and differentiation with *Helicobacter felis* infection," *Gastroenterology*, 114:675–689, 1998.

Wang et al., "Synergistic interaction between hypergastrinemia and Helicobacter infection in a mouse model of gastric cancer," *Gastroenterology*, 118:36–47, 2000.

Weinberger et al., *Science*, 228:740–742, 1985.

Wexler et al., "The isolation and characterisation of a major outer-membrane protein from *Bacteroides distasonis*," *J. Med. Microbiol.*, 37:165–75, 1992

Whitton et al., *J. Virol.* 67:(1)348–352, 1993.

Wolf et al., "An Integrated Family of Amino Acid Sequence Analysis Programs," *Comput. Appl. Biosci.*, 4(1):187–191, 1988.

Yang et al., "The major outer membrane protein, CD, extracted from Moraxella (*Branhamella*) *catarrhalis* is a potential vaccine antigen that induces bactericidal antibodies," FEMS *Immunol. Med. Microbiol.*, 17:187–99, 1997.

Zavros et al., "Use of the Mediman Machine to quantify gastric epithelial cells for flow cytometry," *Dig. Dis. Sci., In Press*, 2000.

Zhang et al., *Helicobacter pylori* infection on the risk of stomach cancer and chronic atrophic gastritis," *Cancer Detect. Prev.*, 23:357–67, 1999.

What is claimed is:

1. A composition comprising at least a first isolated polypeptide that comprises an amino acid sequence that is at least about 90% identical to amino acids 22–349 of the amino acid sequence of SEQ ID NO:2, wherein said isolated polypeptide stimulates IL-8 expression.

2. A composition comprising at least a first antigenic peptide that consists of the amino acid sequence GSRTV-LAEQPVAQ (amino acids 337–349 of SEQ ID NO:2), DTQHNNNGND (amino acids 36–45 of SEQ ID NO:2), TGNYDSKVKP (amino acids 111–120 of SEQ ID NO:2) or YKYEFEGVPRGTRGNEEEG (amino acids 129–147 of SEQ ID NO:2).

3. The composition of claim 1, wherein said composition further comprises at least a first adjuvant.

4. A diagnostic kit, comprising a detection reagent in operative association with an isolated polypeptide comprising an amino acid sequence of at least about 90% identity to amino acids 22–349 of SEQ ID NO:2, wherein said isolated polypeptide stimulates IL-8 expression.

5. The diagnostic kit of claim 4, wherein said detection reagent is at least a first antibody that has immunospecificity for said polypeptide.

6. The diagnostic kit of claim 5, wherein said detection reagent is a detectable label that is operatively attached to said at least a first antibody.

7. The diagnostic kit of claim 5, wherein said detection reagent is a detectable label that is operatively attached to a second antibody that has immunospecificity for said at least a first antibody.

8. A composition comprising a pharmaceutically acceptable carrier or diluent and a therapeutically effective amount of at least a first isolated polypeptide that comprises an amino acid sequence that is at least about 90% identical to amino acids 22–349 of the amino acid sequence of SEQ ID NO:2, wherein said isolated polypeptide stimulates IL-8 expression.

9. An isolated polypeptide that consists of amino acids 22–349 of the amino acid sequence of SEQ ID NO:2.

10. The composition of claim 1, wherein said composition comprises at least a first isolated polypeptide that comprises an amino acid sequence that is at least 92% identical to amino acids 22–349 of the amino acid sequence of SEQ ID NO:2.

11. The composition of claim 10, wherein said composition comprises at least a first isolated polypeptide that comprises an amino acid sequence that is at least 95% identical to amino acids 22–349 of the amino acid sequence of SEQ ID NO:2.

12. The composition of claim 11, wherein said composition comprises at least a first isolated polypeptide that comprises an amino acid sequence that is at least 98% identical to amino acids 22–349 of the amino acid sequence of SEQ ID NO:2.

13. The composition of claim 12, wherein said composition comprises at least a first isolated polypeptide that comprises an amino acid sequence that is at least 99% identical to amino acids 22–349 of the amino acid sequence of SEQ ID NO:2.

14. The composition of claim 13, wherein said composition comprises at least a first isolated polypeptide that has the amino acid sequence of amino acids 22–349 of SEQ ID NO:2.

15. The composition of claim 14, wherein said composition comprises at least a first isolated polypeptide that has the amino acid sequence of SEQ ID NO:2.

16. The composition of claim 1, wherein said composition further comprises a pharmaceutically acceptable carrier or diluent.

17. The composition of claim 1, wherein said composition further comprises at least a first emulsifier.

18. The diagnostic kit of claim 4, wherein said detection reagent is a detectable label that is operatively attached to said polypeptide.

19. The composition of claim 8, wherein said composition comprises at least a first isolated polypeptide that comprises an amino acid sequence that is at least about 95% identical to amino acids 22–349 of the amino acid sequence of SEQ ID NO:2.

20. The composition of claim 19, wherein said composition comprises at least a first isolated polypeptide that has the amino acid sequence of amino acids 22–349 of SEQ ID NO:2.

21. The composition of claim 20, wherein said composition comprises at least a first isolated polypeptide that has the amino acid sequence of SEQ ID NO:2.

22. A composition comprising a pharmaceutically acceptable carrier or diluent and at least a first isolated peptide that consists of the amino acid sequence GSRTVLAEQPVAQ (amino acids 337–349 of SEQ ID NO:2), DTQHNNNGND (amino acids 36–45 of SEQ ID NO:2) TGNYDSKVKP (amino acids 111–120 of SEQ ID NO:2) or YKYEFEGVPRGTRGNEEEG (amino acids 129–147 of SEQ ID NO:2).

23. The composition of claim 8, wherein said composition further comprises at least a first adjuvant.

24. An isolated peptide fragment of the polypeptide of claim 9, wherein said isolated peptide fragment has a sequence of at least 8 contiguous amino acids from amino acids 22–349 of the amino acid sequence of SEQ ID NO:2.

25. The isolated peptide fragment of claim 24, wherein said isolated peptide fragment is at least 10 amino acids in length.

26. The isolated peptide fragment of claim 25, wherein said isolated peptide fragment is at least 12 amino acids in length.

27. The isolated peptide fragment of claim 26, wherein said isolated peptide fragment is at least 15 amino acids in length.

28. The isolated peptide fragment of claim 27, wherein said isolated peptide fragment is at least 20 amino acids in length.

29. The isolated peptide fragment of claim 28, wherein said isolated peptide fragment is at least 25 amino acids in length.

30. The isolated peptide fragment of claim 29, wherein said isolated peptide fragment is at least 30 amino acids in length.

31. The isolated peptide fragment of claim 30, wherein said isolated peptide fragment is at least 35 amino acids in length.

32. The isolated peptide fragment of claim 31, wherein said isolated peptide fragment is at least 50 amino acids in length.

33. A composition comprising a pharmaceutically acceptable carrier or diluent and a therapeutically effective amount of at least a first isolated polypeptide that consists of amino acids 22–349 of the amino acid sequence of SEQ ID NO:2.

34. The composition of claim 33, wherein said composition comprises an isolated peptide fragment from said at least a first isolated polypeptide, wherein said isolated peptide fragment has a sequence of at least 8 contiguous amino acids from amino acids 22–349 of the amino acid sequence of SEQ ID NO:2.

35. The composition of claim 34, wherein said composition comprises an isolated peptide fragment that is at least 20 amino acids in length.

36. The composition of claim 35, wherein said composition comprises an isolated peptide fragment that is at least 50 amino acids in length.

37. A composition comprising an isolated polypeptide that comprises an amino acid sequence that is at least 90% identical to amino acids 22–349 of the amino acid sequence of SEQ ID NO:2, wherein said isolated polypeptide stimulates IL-8 expression and cross-reacts with an antibody that binds to the Acinetobacter outer membrane protein A (OMP A) protein of SEQ ID NO:2.

38. A diagnostic kit, comprising a detection reagent in operative association with an isolated polypeptide comprising an amino acid sequence of at least 90% identity to amino acids 22–349 of SEQ ID NO:2, wherein said isolated polypeptide stimulates IL-8 expression and cross-reacts with an antibody that binds to the Acinetobacter outer membrane protein A (OMP A) protein of SEQ ID NO:2.

39. A composition comprising a pharmaceutically acceptable carrier or diluent and an isolated polypeptide that comprises an amino acid sequence that is at least 90% identical to amino acids 22–349 of the amino acid sequence of SEQ ID NO:2, wherein said isolated polypeptide stimulates IL-8 expression and cross-reacts with an antibody that binds to the Acinetobacter outer membrane protein A (OMP A) protein of SEQ ID NO:2.

40. A composition comprising an isolated peptide fragment of from 8 to about 50 amino acids in length that consists of an amino acid sequence that is identical to a contiguous g amino acid sequence of at least from 8 amino acids from amino acids 22–349 of amino acid sequence of SEQ ID NO:2.

41. A composition comprising an isolated antigenic peptide of from 8 to about 50 amino acids in length that consists of an amino acid sequence that is identical to a contiguous amino acid sequence of at least from 8 amino acids from amino acids 22–349 of the amino acid sequence of SEQ ID NO:2, wherein said isolated antigenic peptide cross-reacts with an antibody binds to the Acinetobacter outer membrane protein A (OMP A) protein of SEQ ID NO:2.

* * * * *

UNITED STATES PATENT AND TRADEMARK OFFICE
CERTIFICATE OF CORRECTION

PATENT NO. : 6,713,062 B1
DATED : March 30, 2004
INVENTOR(S) : Juanita L. Merchant It is certified that error appears in the above-identified patent and that said Letters Patent is hereby corrected as shown below:

<u>Title page,</u>
Item [57], ABSTRACT,
Line 3, delete "Acinetobacter" and insert -- *Acinetobacter* -- therefor.

<u>Column 92,</u>
Lines 12, 20 and 28, delete "Acinetobacter" and insert -- *Acinetobacte*r -- therefor.
Line 33, delete "contiguous g amino" and insert -- contiguous amino -- therefor.
Line 35, after "of" insert -- the --.
Line 43, delete "Acinetobacter" and insert -- *Acinetobacter* -- therefor.

Signed and Sealed this

Twenty-fifth Day of May, 2004

JON W. DUDAS
*Acting Director of the United States Patent and Trademark Office*

SEQUENCE LISTING

<160> NUMBER OF SEQ ID NOS: 6

<210> SEQ ID NO 1
<211> LENGTH: 1050
<212> TYPE: DNA
<213> ORGANISM: Acinetobacter sp.
<220> FEATURE:
<221> NAME/KEY: CDS
<222> LOCATION: (1)..(1047)

<400> SEQUENCE: 1

```
atg aaa atg agt cgt att gct tta gct atg ctt gta gct gca cct ttt      48
Met Lys Met Ser Arg Ile Ala Leu Ala Met Leu Val Ala Ala Pro Phe
  1               5                  10                  15
```

-continued

| | |
|---|---|
| gct gct gca aat gca ggc gta act gtt act ccg ttg atg ttg ggg tac<br>Ala Ala Ala Asn Ala Gly Val Thr Val Thr Pro Leu Met Leu Gly Tyr<br>                  20                      25                  30 | 96 |
| act ttt caa gat acc cag cat aac aat aac ggt aat gat ggc gaa ctt<br>Thr Phe Gln Asp Thr Gln His Asn Asn Asn Gly Asn Asp Gly Glu Leu<br>        35                      40                      45 | 144 |
| act agt agt cct gaa tta caa gac gat tta ttc gta ggt gct gct att<br>Thr Ser Ser Pro Glu Leu Gln Asp Asp Leu Phe Val Gly Ala Ala Ile<br>50                      55                      60 | 192 |
| ggt gtt gaa tta act cct tgg tta ggt ttt gaa gct gaa tat agc caa<br>Gly Val Glu Leu Thr Pro Trp Leu Gly Phe Glu Ala Glu Tyr Ser Gln<br>65                      70                    75                80 | 240 |
| gta aag ggc gat gtt gac ggt gct gct gaa ggt gca gaa tac aaa ggc<br>Val Lys Gly Asp Val Asp Gly Ala Ala Glu Gly Ala Glu Tyr Lys Gly<br>                  85                      90                      95 | 288 |
| caa aat att gca ggt aac ttc tac gca act tct gac gta ttt act ggt<br>Gln Asn Ile Ala Gly Asn Phe Tyr Ala Thr Ser Asp Val Phe Thr Gly<br>                  100                     105                110 | 336 |
| aac tat gac agc aaa gtg aag cca tat atg ctt cta ggt gcg ggt cac<br>Asn Tyr Asp Ser Lys Val Lys Pro Tyr Met Leu Leu Gly Ala Gly His<br>                115                     120                125 | 384 |
| tac aaa tac gaa ttt gaa ggt gtg cca cgc ggt act cgc ggt aat gaa<br>Tyr Lys Tyr Glu Phe Glu Gly Val Pro Arg Gly Thr Arg Gly Asn Glu<br>130                     135                     140 | 432 |
| gaa gaa ggt act cta ggt aat gct ggt gtg ggt gca ttc tgg cac atc<br>Glu Glu Gly Thr Leu Gly Asn Ala Gly Val Gly Ala Phe Trp His Ile<br>145                     150                     155                160 | 480 |
| aac gat gcc tta gcg cta cgt act gaa gct cgt ggt act tac cac ttt<br>Asn Asp Ala Leu Ala Leu Arg Thr Glu Ala Arg Gly Thr Tyr His Phe<br>                  165                     170                175 | 528 |
| gac gaa aaa ttc tgg aac tac aca gca tta gct ggt ctt aat gtt gtt<br>Asp Glu Lys Phe Trp Asn Tyr Thr Ala Leu Ala Gly Leu Asn Val Val<br>                180                     185                190 | 576 |
| cta ggt ggt cgt ctg aaa cca gct gct cca gta gtt gaa gtt gct cca<br>Leu Gly Gly Arg Leu Lys Pro Ala Ala Pro Val Val Glu Val Ala Pro<br>              195                     200                205 | 624 |
| gtt gag cct gta act cca gtt gct cca ccg cca caa gag ttg act gaa<br>Val Glu Pro Val Thr Pro Val Ala Pro Pro Pro Gln Glu Leu Thr Glu<br>210                     215                     220 | 672 |
| gac ctg aac atg gaa ctt cgt gtt ttt ttc gac act aac aaa agc aac<br>Asp Leu Asn Met Glu Leu Arg Val Phe Phe Asp Thr Asn Lys Ser Asn<br>225                     230                     235                240 | 720 |
| atc aaa gat caa tac aaa cca gaa atc gct aaa gtt gct gag aag cta<br>Ile Lys Asp Gln Tyr Lys Pro Glu Ile Ala Lys Val Ala Glu Lys Leu<br>                    245                     250                255 | 768 |
| gtt gaa tat cca aac gct act gct cgt atc gaa ggt cac act gac aac<br>Val Glu Tyr Pro Asn Ala Thr Ala Arg Ile Glu Gly His Thr Asp Asn<br>                260                     265                270 | 816 |
| act ggt cca cgt gca cta aac gaa cgt tta tct cta gca cgt gct aac<br>Thr Gly Pro Arg Ala Leu Asn Glu Arg Leu Ser Leu Ala Arg Ala Asn<br>              275                     280                285 | 864 |
| tct gtt aaa tct tcg ctt gta aat gaa tac aat gtt gat gca tct cgc<br>Ser Val Lys Ser Ser Leu Val Asn Glu Tyr Asn Val Asp Ala Ser Arg<br>        290                     295                     300 | 912 |
| ttg tct act caa ggt ttc gct tgg gat caa ccg att gct gac aac aac<br>Leu Ser Thr Gln Gly Phe Ala Trp Asp Gln Pro Ile Ala Asp Asn Asn<br>305                     310                     315                320 | 960 |
| act aaa gaa ggt cgt gct atg aac cgt cgt gta ttc gcg aca atc act<br>Thr Lys Glu Gly Arg Ala Met Asn Arg Arg Val Phe Ala Thr Ile Thr<br>                  325                     330                335 | 1008 |

```
ggt agc cgt act gtt tta gct gaa caa cca gtt gct caa taa              1050
Gly Ser Arg Thr Val Leu Ala Glu Gln Pro Val Ala Gln
        340                 345
```

<210> SEQ ID NO 2
<211> LENGTH: 349
<212> TYPE: PRT
<213> ORGANISM: Acinetobacter sp.

<400> SEQUENCE: 2

```
Met Lys Met Ser Arg Ile Ala Leu Ala Met Leu Val Ala Ala Pro Phe
 1               5                  10                  15

Ala Ala Ala Asn Ala Gly Val Thr Val Thr Pro Leu Met Leu Gly Tyr
            20                  25                  30

Thr Phe Gln Asp Thr Gln His Asn Asn Gly Asn Asp Gly Glu Leu
        35                  40                  45

Thr Ser Ser Pro Glu Leu Gln Asp Asp Leu Phe Val Gly Ala Ala Ile
50                  55                  60

Gly Val Glu Leu Thr Pro Trp Leu Gly Phe Glu Ala Glu Tyr Ser Gln
65                  70                  75                  80

Val Lys Gly Asp Val Asp Gly Ala Ala Glu Gly Ala Glu Tyr Lys Gly
                85                  90                  95

Gln Asn Ile Ala Gly Asn Phe Tyr Ala Thr Ser Asp Val Phe Thr Gly
            100                 105                 110

Asn Tyr Asp Ser Lys Val Lys Pro Tyr Met Leu Leu Gly Ala Gly His
        115                 120                 125

Tyr Lys Tyr Glu Phe Glu Gly Val Pro Arg Gly Thr Arg Gly Asn Glu
    130                 135                 140

Glu Glu Gly Thr Leu Gly Asn Ala Gly Val Gly Ala Phe Trp His Ile
145                 150                 155                 160

Asn Asp Ala Leu Ala Leu Arg Thr Glu Ala Arg Gly Thr Tyr His Phe
                165                 170                 175

Asp Glu Lys Phe Trp Asn Tyr Thr Ala Leu Ala Gly Leu Asn Val Val
            180                 185                 190

Leu Gly Gly Arg Leu Lys Pro Ala Ala Pro Val Val Glu Val Ala Pro
        195                 200                 205

Val Glu Pro Val Thr Pro Val Ala Pro Pro Gln Glu Leu Thr Glu
    210                 215                 220

Asp Leu Asn Met Glu Leu Arg Val Phe Phe Asp Thr Asn Lys Ser Asn
225                 230                 235                 240

Ile Lys Asp Gln Tyr Lys Pro Glu Ile Ala Lys Val Ala Glu Lys Leu
                245                 250                 255

Val Glu Tyr Pro Asn Ala Thr Ala Arg Ile Glu Gly His Thr Asp Asn
            260                 265                 270

Thr Gly Pro Arg Ala Leu Asn Glu Arg Leu Ser Leu Ala Arg Ala Asn
        275                 280                 285

Ser Val Lys Ser Ser Leu Val Asn Glu Tyr Asn Val Asp Ala Ser Arg
    290                 295                 300

Leu Ser Thr Gln Gly Phe Ala Trp Asp Gln Pro Ile Ala Asp Asn Asn
305                 310                 315                 320

Thr Lys Glu Gly Arg Ala Met Asn Arg Val Phe Ala Thr Ile Thr
                325                 330                 335

Gly Ser Arg Thr Val Leu Ala Glu Gln Pro Val Ala Gln
            340                 345
```

```
<210> SEQ ID NO 3
<211> LENGTH: 36
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

<400> SEQUENCE: 3
cgcggatcca tggcctattg cgggcttgag cttgaa                              36

<210> SEQ ID NO 4
<211> LENGTH: 39
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

<400> SEQUENCE: 4
cgcggatccg gcgtaactgt tactccgttg atgttgggg                           39

<210> SEQ ID NO 5
<211> LENGTH: 36
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

<400> SEQUENCE: 5
ctcgaattct tgagcaactg gttgttcagc taaaac                              36

<210> SEQ ID NO 6
<211> LENGTH: 1701
<212> TYPE: DNA
<213> ORGANISM: Acinetobacter sp.

<400> SEQUENCE: 6
tggggaaagg ggatgtgctg caaggcgatt aagttgggta acgccaggtt ttcccagtca    60
cgacgttgta aaacgacgcc cagtgaattg taatacgact cactataggg cgaattgggt   120
accggccccc cttcgagttc gacggtatcg ataagcttga tatcgaatta actcaacaat   180
agtgaatgct cttgttattt ttttatacat agagttacct gatttatata ttatttttat   240
gaggaatatg ttattaatta tgcgtttttt atgctttgtg gagccgagta atcagtcctt   300
acttaagttt caagaaagtg attaaaaaat aattggcaat caccataggg tattcagaat   360
aaaaaattga gtaaaaagtt accgaattac aacggaaatt gtaagtaatt ttgtcaataa   420
tttacttgat taaattaatc aagcacttgg aaaaataata aagtgtttgt atgatgccat   480
gtgaatagct taagaataaa actggggtaa taaaaagcct atctcaggat ggcctattgc   540
gggcttgagc ttgaacaaca atttttatct ctggaggata aatccatgaa aatgagtcgt   600
attgctttag ctatgcttgt agctgcacct tttgctgctg caaatgcagg cgtaactgtt   660
actccgttga tgttggggta cttttcaa gatacccagc ataacaataa cggtaatgat   720
ggcgaactta ctagtagtcc tgaattacaa gacgatttat tcgtaggtgc tgctattggt   780
gttgaattaa ctccttggtt aggttttgaa gctgaatata gccaagtaaa gggcgatgtt   840
gacggtgctg ctgaaggtgc agaatacaaa ggccaaaata ttgcaggtaa cttctacgca   900
acttctgacg tatttactgg taactatgac agcaaagtga agccatatat gcttctaggt   960
gcgggtcact acaaatacga atttgaaggt gtgccacgcg gtactcgcgg taatgaagaa  1020
```

```
gaaggtactc taggtaatgc tggtgtgggt gcattctggc acatcaacga tgccttagcg    1080
ctacgtactg aagctcgtgg tacttaccac tttgacgaaa aattctggaa ctacacagca    1140
ttagctggtc ttaatgttgt tctaggtggt cgtctgaaac cagctgctcc agtagttgaa    1200
gttgctccag ttgagcctgt aactccagtt gctccaccgc cacaagagtt gactgaagac    1260
ctgaacatgg aacttcgtgt tttttttcgac actaacaaaa gcaacatcaa agatcaatac    1320
aaaccagaaa tcgctaaagt tgctgagaag ctagttgaat atccaaacgc tactgctcgt    1380
atcgaaggtc acactgacaa cactggtcca cgtgcactaa acgaacgttt atctctagca    1440
cgtgctaact ctgttaaatc ttcgcttgta aatgaataca atgttgatgc atctcgcttg    1500
tctactcaag gtttcgcttg ggatcaaccg attgctgaca acaacactaa agaaggtcgt    1560
gctatgaacc gtcgtgtatt cgcgacaatc actggtagcc gtactgtttt agctgaacaa    1620
ccagttgctc aataattcat tattgaacac tcattaaaag gcagctcttc gacctgcttt    1680
tttagtctgt atttgactac c                                              1701
```